United States Patent
Shimoda

(10) Patent No.: US 9,433,482 B2
(45) Date of Patent: Sep. 6, 2016

(54) HUMAN BODY IMPLANT STRUCTURE, METHOD OF ASSEMBLING THE STRUCTURE AND METHOD OF DISASSEMBLING THE STRUCTURE

(75) Inventor: Tsunehisa Shimoda, Fukuoka (JP)

(73) Assignee: Arthro Co., Ltd., Fukuoka (JP)

( * ) Notice: Subject to any disclaimer, the term of this patent is extended or adjusted under 35 U.S.C. 154(b) by 1024 days.

(21) Appl. No.: 12/872,547

(22) Filed: Aug. 31, 2010

(65) Prior Publication Data

US 2011/0053114 A1   Mar. 3, 2011

(30) Foreign Application Priority Data

Sep. 2, 2009  (JP) .................. 2009-203110
Apr. 30, 2010  (JP) .................. 2010-104971

(51) Int. Cl.
*A61C 8/00*  (2006.01)
*A61C 7/36*  (2006.01)
*A61F 2/14*  (2006.01)
*A61F 2/18*  (2006.01)

(52) U.S. Cl.
CPC .............. *A61C 8/005* (2013.01); *A61C 7/36* (2013.01); *A61C 8/0001* (2013.01); *A61C 8/0089* (2013.01); *A61C 8/0096* (2013.01); *A61C 8/0098* (2013.01); *A61C 8/006* (2013.01); *A61C 8/0068* (2013.01); *A61F 2/14* (2013.01); *A61F 2/18* (2013.01)

(58) Field of Classification Search
CPC .......... A61C 7/36; A61C 8/00; A61C 8/005; A61C 8/0068; A61C 8/0089; A61C 8/0096; A61C 8/0098; A61F 2/14; A61F 2/18; A61F 2/4684; A61F 2240/007; A63H 3/38; A61H 3/48; B23B 31/00; B23B 31/023; B23B 31/1238; B23B 31/1246; B23B 31/16045
USPC .................. 433/172–176, 201.1; 623/10, 4.2
See application file for complete search history.

(56) References Cited

U.S. PATENT DOCUMENTS

| | | | | | |
|---|---|---|---|---|---|
| 4,416,629 | A | * | 11/1983 | Mozsary et al. | 433/174 |
| 4,756,689 | A | * | 7/1988 | Lundgren et al. | 433/173 |
| 4,772,204 | A | * | 9/1988 | Soderberg | 433/174 |
| 4,790,753 | A | * | 12/1988 | Fradera | 433/174 |
| 4,850,870 | A | * | 7/1989 | Lazzara et al. | 433/174 |
| 5,006,069 | A | * | 4/1991 | Lazzara et al. | 433/173 |
| 5,040,983 | A | * | 8/1991 | Binon | 433/173 |

(Continued)

FOREIGN PATENT DOCUMENTS

JP          7-275266       10/1995
WO      WO 9952466 A1 *  10/1999

*Primary Examiner* — Cris L Rodriguez
*Assistant Examiner* — Mirayda A Aponte
(74) *Attorney, Agent, or Firm* — Norris McLaughlin & Marcus, P.A.

(57) ABSTRACT

A human body implant structure includes: a support anchor which is embedded into a bone body; a support base which is placed on and fixed to an upper portion of the support anchor; and a lost-part compensation part which is mounted on an upper portion of the support base, wherein the support anchor and the support base are configured to be detachably fitted to each other by way of the taper fitting structure where the support anchor and the support base are brought into close contact with each other, and a stepped portion which is formed of an upper surface of the support anchor is formed on a boundary between a female threaded hole which is vertically formed in the support base and a vertical hole formed in the upper surface of the support anchor.

9 Claims, 37 Drawing Sheets

(56) References Cited

U.S. PATENT DOCUMENTS

| | | | |
|---|---|---|---|
| 5,069,622 A * | 12/1991 | Rangert et al. | 433/173 |
| 5,073,111 A * | 12/1991 | Daftary | 433/173 |
| 5,104,318 A * | 4/1992 | Piche et al. | 433/174 |
| 5,116,225 A * | 5/1992 | Riera | 433/173 |
| 5,145,371 A * | 9/1992 | Jorneus | 433/173 |
| 5,376,004 A * | 12/1994 | Mena | 433/173 |
| 5,433,606 A * | 7/1995 | Niznick et al. | 433/173 |
| 5,435,723 A * | 7/1995 | O'Brien | 433/174 |
| 5,468,150 A * | 11/1995 | Brammann | 433/173 |
| 5,662,474 A * | 9/1997 | Jorneus et al. | 433/172 |
| 5,863,200 A * | 1/1999 | Hamada et al. | 433/173 |
| 5,882,200 A * | 3/1999 | Sutter et al. | 433/173 |
| 6,168,436 B1 * | 1/2001 | O'Brien | 433/173 |
| 6,244,867 B1 * | 6/2001 | Aravena et al. | 433/172 |
| 6,419,492 B1 * | 7/2002 | Schroering | 433/173 |
| 7,090,495 B1 * | 8/2006 | Rosen | 433/174 |
| 2002/0123022 A1 * | 9/2002 | Pilla et al. | 433/173 |
| 2004/0063069 A1 * | 4/2004 | Lombardi | 433/173 |
| 2008/0057473 A1 * | 3/2008 | Rosen | 433/173 |
| 2008/0057477 A1 * | 3/2008 | Rosen | 433/174 |
| 2008/0274440 A1 * | 11/2008 | Smith et al. | 433/174 |
| 2009/0117520 A1 * | 5/2009 | Kikuchi | 433/174 |

* cited by examiner

HUMAN BODY IMPLANT STRUCTURE, METHOD OF ASSEMBLING THE STRUCTURE AND METHOD OF DISASSEMBLING THE STRUCTURE

CROSS-REFERENCE TO RELATED APPLICATIONS

This application is based on and claims the benefit of priority from Japanese Patent Application No. 2009-203110 filed on Sep. 2, 2009 and Japanese Patent Application No. 2010-104971 filed on Apr. 30, 2010, the entire contents of which are incorporated herein by reference.

BACKGROUND

1. Field

The present invention relates to the human body implant structure such as a dental implant, a method of assembling the human body implant structure, and a method of disassembling the human body implant structure for disassembling the implant structure which is once assembled for repair and inspection.

2. Description of the Related Art

To consider a case where a part of a human body is lost due to an accident, a disease or the like, there has been known a technique which compensates for such a lost part with a lost-part compensation part such as an artificial tooth, an artificial eye or an artificial ear, for example.

In such a case, to mount the lost-part compensation part on the human body, there has been adopted a method where a support anchor is implanted in a bone body in the vicinity of the lost part, a support base for mounting the lost-part compensation part is mounted on the support anchor thus mounting the lost-part compensation part on the support base.

The explanation will be made hereinafter by taking the dental implant structure of an artificial tooth as a specific example of these lost-part compensation parts as an example.

That is, conventionally, the dental implant structure used for a case where a single tooth per se is lost is assembled in order that an artificial dental root called fixture is embedded in a jaw bone such that the artificial dental root is integrally formed with the jaw bone along with the curing of the bone, a support base called abutment is mounted upright in a gingiva for supporting the artificial tooth on the artificial dental root, and a dental crown which is capped over the artificial tooth is placed on and fixed to the support base using an adhesive agent, a screw or the like. For example, JP-7-275266 (patent document 1) discloses the implant structure where an abutment is threadedly engaged with a dental implant which constitutes a fixture.

The specific constitution of the dental implant structure described in documents including the above-mentioned patent document is shown in FIG. 56 and FIG. 57. FIG. 56 shows the dental implant structure 101 where a dental crown is fixed to a support body using an adhesive A agent. An abutment 103 which is mounted upright in a gingiva is threadedly engaged with a fixture 102 embedded in a jaw bone B, and a dental crown 104 formed by casting is adhered to the abutment 103 using an adhesive agent 105 such as cement. On the other hand, FIG. 57 shows the dental implant structure 111 where a dental crown is fixed to a support base using a screw. An abutment 113 which is mounted upright in a gingiva A is threadedly engaged with a fixture 112 embedded in a jaw bone B, and a dental crown 114 formed by casting is threadedly engaged with the abutment 113. That is, in the above-mentioned both dental implant structures, the fixture and the abutment are threadedly engaged with each other, the dental crown is formed by casting in conformity with an outer shape of the abutment, and an upper portion of the dental crown is placed on and fixed to the abutment using the adhesive agent, the screw or the like.

Further, in case of bridging denture which is formed by bridging a plurality of artificial teeth, support bases made of metal or the like for a plurality of bridged artificial teeth respectively are prepared by grinding using a machine such that the plurality of artificial teeth can maintain parallelism, and upper portions of the support bases are covered with dentals crowns which constitute bridging denture by way of dental-use cement or screws.

SUMMARY OF THE INVENTION

However, the conventional dental implant structure is, as described above, configured such that the dental crown which is capped over with the artificial tooth is placed on and fixed to the support base called the abutment using the adhesive agent such as cement or the screw.

In the repair of the dental implant structure where the parts are adhered to each other using the adhesive agent such as cement, once the dental crown is fixed to the support base, the removal of the dental crown is difficult so that it is necessary to repair the dental implant structure by breaking and removing the dental crown for every abutment which constitutes the support base for the dental crown. That is, when it is necessary to repair or inspect the dental implant structure because of the lapse of duration due to the use of the dental implant structure for long years or because of some accident, it is difficult to repair or inspect the dental implant structure by removing the constitutional member such as the dental crown, the support base or the dental root individually, and it is necessary to break the constitutional members, to remove the whole or parts of the dental implant structure, and manufacture the new dental implant structure. Such an operation increases a physical burden imposed on a patient, and is disadvantageous in view of time and cost for repair. Further, there may be a case where cement or metal of a cast product is dissolved due to saliva, and this dissolving of metal becomes a cause of damaging a health of human body.

On the other hand, in case of the repair of the dental implant structure where the parts are jointed to each other using the screw, inadvertent slackening of the screw may occur or a complicated precision forming operation becomes necessary and hence, this dental implant structure cannot also overcome a cause of damaging a health of human body due to dissolving of metal from the cast product.

Further, both repair modes have drawbacks including a drawback where a floating phenomenon occurs at the time of mounting the dental crown so that a floating portion becomes unhygienic. Still further, both repair modes also have a drawback that an artificial tooth base is removed due to shortage of a holding force generated by the screw or the screw which fixes the support base is broken.

The above-mentioned explanation of the dental implant structure is also applicable to a technique for mounting a lost-part compensation part such as an artificial eye or an artificial ear besides the artificial tooth.

The present invention has been made under such circumstances, and it is an object of the present invention to provide a human body implant structure such as a dental implant, a method of assembling the human body implant structure, and a method of disassembling the human body implant structure for disassembling the assembled implant structure for repair and inspection which can overcome the above-mentioned drawbacks.

(1) According to one aspect of the present invention, there is provided a human body implant structure including: a support anchor which is embedded into a bone body; a support base which is placed on and fixed to an upper portion of the support anchor; and a lost-part compensation part which is mounted on an upper portion of the support base, wherein the support anchor and the support base are configured to be detachably fitted to each other by way of the taper fitting structure where the support anchor and the support base are brought into close contact with each other, and a stepped portion which is formed of an upper surface of the support anchor is formed on a boundary between a female threaded hole which is vertically formed in the support base and a vertical hole formed in the upper surface of the support anchor.

(2) In the human body implant structure having the constitution (1), the bone body is a jaw bone, the support anchor is constituted of the combination of a fixture, and an abutment which is configured to be placed on and fixed to an upper portion of the fixture and to place and fix an artificial tooth which constitutes the lost-part compensation part onto an upper portion thereof, the support base is constituted of an artificial tooth base, the lost-part compensation part is constituted of the artificial tooth, the human body implant structure is constituted of a dental implant structure, and the abutment and the artificial tooth base are configured to be detachably fitted to each other by way of the taper fitting structure where the abutment and the artificial tooth base are brought into close contact with each other, and a stepped portion which is formed of an upper surface of the abutment is formed on a boundary between a female threaded hole which is vertically formed in the artificial tooth base and a male screw penetration hole which is vertically formed in the abutment.

(3) In the human body implant structure having the constitution (2), the fixture which is embedded into the jaw bone and the abutment which is configured to place and fix the artificial tooth onto the upper portion thereof are integrally connected to each other by way of a male screw rod whose upper portion has a shape which conforms with a shape of the male screw penetration hole which is formed in the support base in a penetrating manner.

(4) In the human body implant structure having the constitution (3), the male screw penetration hole which is formed in the abutment in a penetrating manner is formed in an expanded manner with a diameter thereof gradually increased upwardly.

(5) According to another aspect of the present invention, there is provided a human body implant assembling method including the steps of:

i) embedding a fixture for placing and fixing an abutment onto an upper portion thereof into a jaw bone;

ii) continuously fixing the abutment on the fixture in such a manner that the abutment which is configured to place and fix an artificial tooth onto an upper portion thereof is placed on the upper portion of the fixture and, thereafter, a male screw rod is inserted into a female threaded hole and a male screw penetration hole which are formed in the abutment and the fixture respectively in a corresponding manner, and the male screw rod is threadedly engaged with the female threaded hole formed in the fixture using a male screw fastening jig which is prepared separately;

iii) fitting an artificial tooth base onto a peripheral surface of the abutment in a close contact manner in such a manner that the artificial tooth base is detachably placed on the upper portion of the abutment by way of the taper fitting structure, an artificial tooth base fastening screw jig which is prepared separately is threadedly engaged with a female threaded hole and is threadedly advanced while maintaining a contact of a distal end of the screw jig with an upper end of the male screw rod disposed below the screw jig;

iv) covering a tooth arranged portion including the artificial tooth base with a molding resin for taking a mold for a tooth and a teeth arranged portion including the artificial tooth base;

v) separating the abutment and the artificial tooth base from each other by making use of a pressure contact reaction force which is generated by bringing a distal end surface of a separation male screw jig which is prepared separately into pressure contact with a stepped portion of the abutment due to threaded engagement of the separation male screw jig with a female threaded hole formed in the artificial tooth base from above the molding resin thus leaving the abutment in the inside of an oral cavity;

vi) fitting a dummy temporarily holding anchor in such a manner that the molding resin which includes the artificial tooth base separated from the abutment is taken out from the inside of an oral cavity and is reversed, and into a tapered fitting hole which is formed in the artificial tooth base and is opened on a surface of the molding resin, the dummy temporarily holding anchor having a distal end portion thereof formed into a shape corresponding to the fitting hole is fitted by way of the taper fitting structure;

vii) flowing a molding material such as plaster into a recessed portion of a surface of the molding resin so as to embed the temporarily holding anchor in a state where the dummy temporarily holding anchor is fitted and mounted upright in the tapered fitting hole formed in the artificial tooth base by way of the taper fitting structure;

viii) completing a teeth arrangement model in the oral cavity made of the molding material such as plaster by removing the molding material which is hardened together with the temporarily holding anchor from the surface recessed portion of the molding resin while leaving the artificial tooth base in the inside of the molding resin after hardening the molding material;

ix) fitting the artificial tooth base into the anchor in such a manner that a separately prepared artificial tooth base is fitted and placed onto a tapered head of the temporarily holding anchor which is exposed at an implant corresponding portion of the teeth arrangement model by way of taper fitting structure;

x) capping an artificial tooth over the artificial tooth base while adjusting the tooth arranged model around the artificial tooth base;

xi) removing the artificial tooth base by separating the artificial tooth base from the temporarily holding anchor by making use of a pressure contact reaction force generated by bringing a distal end surface into pressure contact with an upper end surface of the temporarily holding anchor by threadedly engaging a separation male screw jig which is prepared separately from a start end of a female threaded hole formed in the artificial tooth base;

xii) fitting the removed artificial tooth base onto the abutment which is mounted in the inside of the oral cavity of a patient by way of the taper fitting structure, and threadedly engaging an artificial tooth base fastening screw jig which is prepared separately with a female threaded hole and further threadedly advancing the artificial tooth base fastening screw while maintaining a contact of the a distal end of the artificial tooth base fastening screw jig with an upper end surface of the male screw rod disposed below the artificial tooth base fastening screw jig thus fitting the peripheral surface of the abutment into the fitting hole formed in the artificial tooth base in a close contact manner; and xiii) closing the female threaded hole formed in a center portion of the artificial tooth base.

(6) According to another aspect of the present invention, there is provided a method of disassembling the human body implant structure having the above-mentioned constitution (1) or (2), wherein the upper male screw which is threadedly engaged with the female threaded hole vertically formed in the artificial tooth base is threadedly disengaged from an upper-end opening portion of the female threaded hole and is removed and, thereafter, a separation male screw jig which is constituted of a male screw and is prepared separately is threadedly engaged with the female threaded hole from which the male screw is removed until a lower end surface of the separation male screw jig is brought into contact with a stepped portion positioned at a lowermost end of the female threaded hole and, thereafter, the separation male screw jig is further threadedly engaged with the female threaded hole so as to separate and remove the artificial tooth base from the abutment by making use of a reaction force of the artificial tooth base against the abutment.

(7) In the human body implant structure, the method of assembling the human body implant structure and the method of disassembling the human body implant structure having any one of the constitutions (2) to (6), the fixture and the abutment are formed into the integral structure.

(8) In the human body implant structure having any one of the constitutions (2) to (4), an engaging portion with which a wire used in orthodontic is engaged is provided to the artificial tooth base instead of the artificial tooth which constitutes a lost-part compensation part.

(9) In the human body implant structure having any one of the constitution (1), the lost-part compensation part is one selected from a group consisting of an artificial eye, an artificial ear and an artificial nose.

According to the above-mentioned one aspect of the present invention, the support anchor and the support base are configured to be detachably fitted to each other in a close contact manner by way of a taper fitting structure where the support anchor and the support base are brought into close contact with each other, and a stepped portion which is formed of an upper surface of the support anchor is formed on a boundary between a vertical female threaded hole formed in the support base and the vertical male screw penetration hole formed in the upper surface of the support anchor. Accordingly, with the use of a support base fastening screw jig, the support anchor and the support base are engaged with each other by way of the taper fitting structure so that the fitting engagement and the separation of both members can be surely performed. An assembling operation of the implant can be performed within a short time. The repair and the inspection of the human body implant structure after assembling can be easily performed. Accordingly, medical psychological burden imposed on a patient can be reduced as much as possible. Further, the adhesion using a screw or cement is not used and hence, a complicate operation is unnecessary whereby the fitting connection operation or the removal operation of the abutment and the artificial tooth base can be performed with a simple operation. In this manner, since the fitting engagement of the support anchor and the support base is performed by way of the taper fitting structure using the support base fastening screw jig which is prepared separately, the adhesion using cement or the engagement using the screw becomes unnecessary so that various drawbacks on dental care attributed to the adhesion using cement and the engagement using the screw can be obviated.

Further, the stepped portion is formed on the boundary between the respective threaded holes and hence, in performing the fitting engagement of the support anchor and the support base by way of the taper fitting structure using an artificial tooth base fastening screw jig, a fastening effect obtained by the artificial tooth base fastening screw jig can be surely and easily increased by making use of the stepped portion. Further, the support base can be easily removed from the support anchor by making use of a fastening reaction force which acts on the stepped portion.

According to the inventions having the above-mentioned constitutions (2) to (4), the male screw penetration hole formed in the abutment in a penetrating manner is formed in an expanded manner with a diameter thereof gradually increased upwardly and, further, the fixture embedded into the jaw bone and the abutment which is configured to place and fix the artificial tooth onto the upper portion thereof are integrally connected with each other by way of the male screw rod whose upper half portion conforms with the male screw penetration hole which is formed in the support base in a penetrating manner. Accordingly, when both members are connected with each other by the male screw rod, it is possible to prevent the abutment from being easily removed from the fixture due to the above-mentioned expanded shape thus surely connecting and fixing these members with each other. Further, when necessary, the fastening force between the fixture and the abutment can be further increased due to the male screw rod by a simple operation so that the implant assembling operation can be performed accurately within a short time at a low cost irrelevant to skill.

According to the invention having the constitution (5), in step iii), the peripheral surface of the abutment is fitted into the fitting hole formed in the artificial tooth base in a close contact manner in such a manner that the artificial tooth base is detachably placed on the upper portion of the abutment by way of the taper fitting structure, the artificial tooth base fastening screw jig which is prepared separately is threadedly engaged with the female threaded hole and is threadedly advanced while maintaining a contact of a distal end of the screw jig with an upper end surface of the male screw rod disposed below the screw jig. Accordingly, it is possible to easily connect the artificial tooth base to the abutment without using the adhesive agent such as cement.

In step v), the abutment and the artificial tooth base are separated from each other. In step vi), the molding resin which includes the artificial tooth base separated from the abutment is taken out from the inside of an oral cavity and is reversed, and the dummy temporarily holding anchor is fitted into the tapered fitting hole which is formed in the artificial tooth base and is opened on a surface of the molding resin. Accordingly, the succeeding preparation of forming the model using the molding material can be easily performed.

In step vii) and step viii), the molding material such as plaster is made to flow into the recessed portion of the surface of the molding resin and, after the molding material is hardened, the molding material which is hardened is removed from the surface recessed portion of the molding resin together with the temporarily holding anchor while leaving the artificial tooth base in the inside of the molding resin thus completing the teeth arrangement model made of the molding material such as plaster in the oral cavity. In step ix), the artificial tooth base is fitted onto the anchor in such a manner that the separately prepared artificial tooth base is fitted and placed onto the tapered head of the temporarily holding anchor which is exposed at the implant corresponding portion of the teeth arrangement model by way of the taper fitting structure. Accordingly, the artificial tooth base which is finally mounted in the inside of the oral cavity can be produced by taking a balance between the artificial tooth base and the neighboring teeth and the arrangement of other teeth of the model into consideration.

In step x), the artificial tooth is capped over the artificial tooth base while adjusting the balance between the artificial tooth and the teeth arranging model around the artificial tooth base, and in step xi), the artificial tooth base is removed by separating the artificial tooth base from the temporarily holding anchor by making use of a pressure contact reaction force generated by bringing a distal end surface into pressure contact with an upper surface of the temporarily holding anchor by threadedly engaging a separation male screw jig which is prepared separately from one end of a female threaded hole formed in the artificial tooth base. Accordingly, it is possible to obtain the artificial tooth base which can be accurately fitted onto the actual abutment in the oral cavity.

In step xii), the removed artificial tooth base is fitted onto the abutment which is mounted in the inside of the oral cavity of a patient by way of the taper fitting structure and, subsequently, the peripheral surface of the abutment is fitted into the fitting hole formed in the artificial tooth base in a close contact manner by threadedly engaging the artificial tooth base fastening screw jig which is separately prepared in the female threaded hole while bringing the distal end of the screw jig into contact with the upper end surface of the male screw rod below the screw jig. Accordingly, it is possible to assemble the safe artificial tooth base surely and easily without using an adhesive agent such as cement.

In step xiii), by closing the female threaded hole formed in a center portion of the artificial tooth base, the intrusion of a foreign material into the female threaded hole can be prevented. Further, slackening of the joining between the fixture and the abutment can be prevented.

In this manner, by constituting the dental implant structure using the respective steps having the constitution (4) as described above, the artificial tooth base and the abutment can be easily mounted and removed so that even a novice who is not an expert in implant assembling can surely perform the implant assembling operation and, at the same time, a medical psychological burden imposed on a patient can be reduced as much as possible.

According to the invention having the constitution (6), the upper male screw which is threadedly engaged with the female threaded hole vertically formed in the artificial tooth base is threadedly disengaged from an upper-end opening portion of the female threaded hole and is removed and, thereafter, a separation male screw jig which is constituted of a male screw and is prepared separately is threadedly engaged with the female threaded hole from which the male screw is removed until a lower end surface of the separation male screw jig is brought into pressure contact with a stepped portion positioned at a lowermost end of the female threaded hole and, thereafter, the separation male screw jig is further threadedly engaged with the female threaded hole so as to separate and remove the artificial tooth base from the abutment by making use of a reaction force of the artificial tooth base against the abutment. Accordingly, the artificial tooth base can be easily removed from the abutment and hence, the repair of the implant can be easily performed thus making the method of disassembling the human body implant structure advantageous also from viewpoints of operability and cost.

According to the invention having the constitution (9), the fixture and the abutment are formed into the integral structure and hence, the present invention can provide the implant structure which has the simple and reliable structure, the assembling method which can easily assemble the implant structure, and the disassembling method which can easily disassemble the implant structure.

According to the invention having the constitution (10), the artificial tooth base can be used for engaging the wire used in orthodontic and hence, the accurate orthodontic can be performed by surely engaging the wire with the artificial tooth base.

According to the invention having the constitution (11), when the lost-part compensation part is one selected from a group consisting of an artificial eye, an artificial ear and an artificial nose, it is possible to surely mount such an artificial eye or the like on a bone body present in the vicinity of a lost part without falling the artificial eye or the like.

DESCRIPTION OF THE PREFERRED EMBODIMENTS

An embodiment of the present invention is explained in detail in conjunction with drawings.

Figure 1:
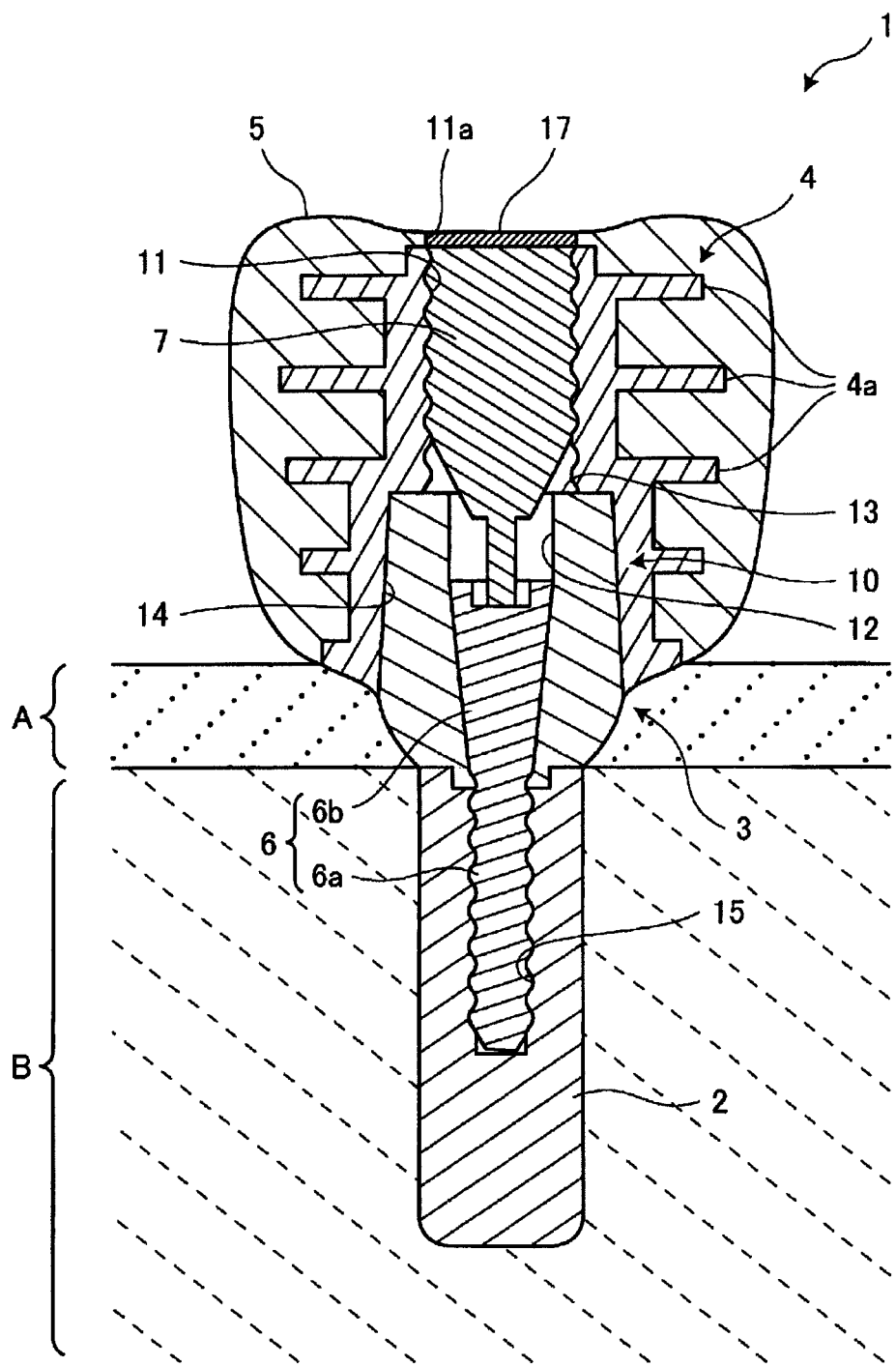
FIG. 1 is an explanatory view showing the dental implant structure of an embodiment.
Figure 53:
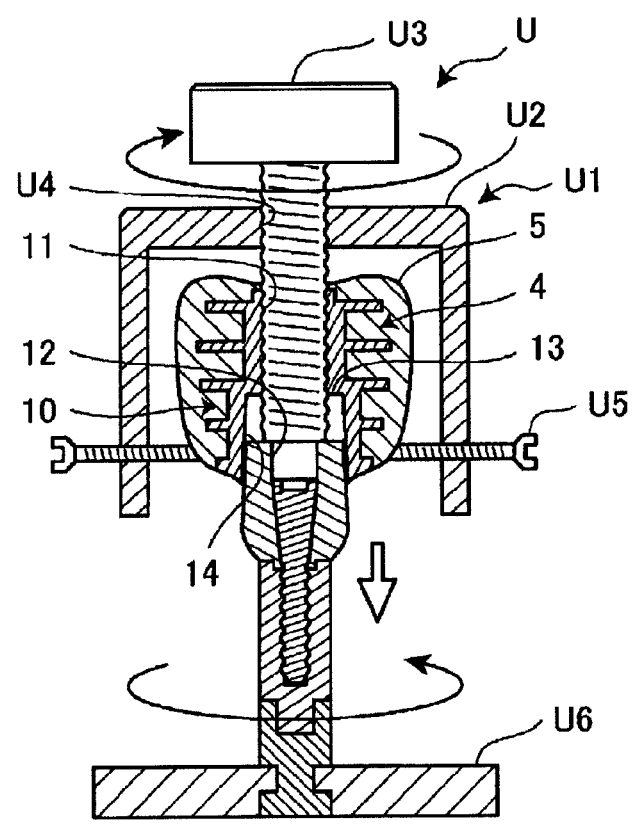
FIG. 53 is an explanatory view showing the steps of the manner of using the artificial tooth base removing jig.

The dental implant structure, a method of assembling the dental implant structure, and a method of disassembling the dental implant structure according to the embodiment of the present invention are constituted as follows as shown in FIG. 1 to FIG. 53.

I [Dental Implant Structure]

Figure 2:
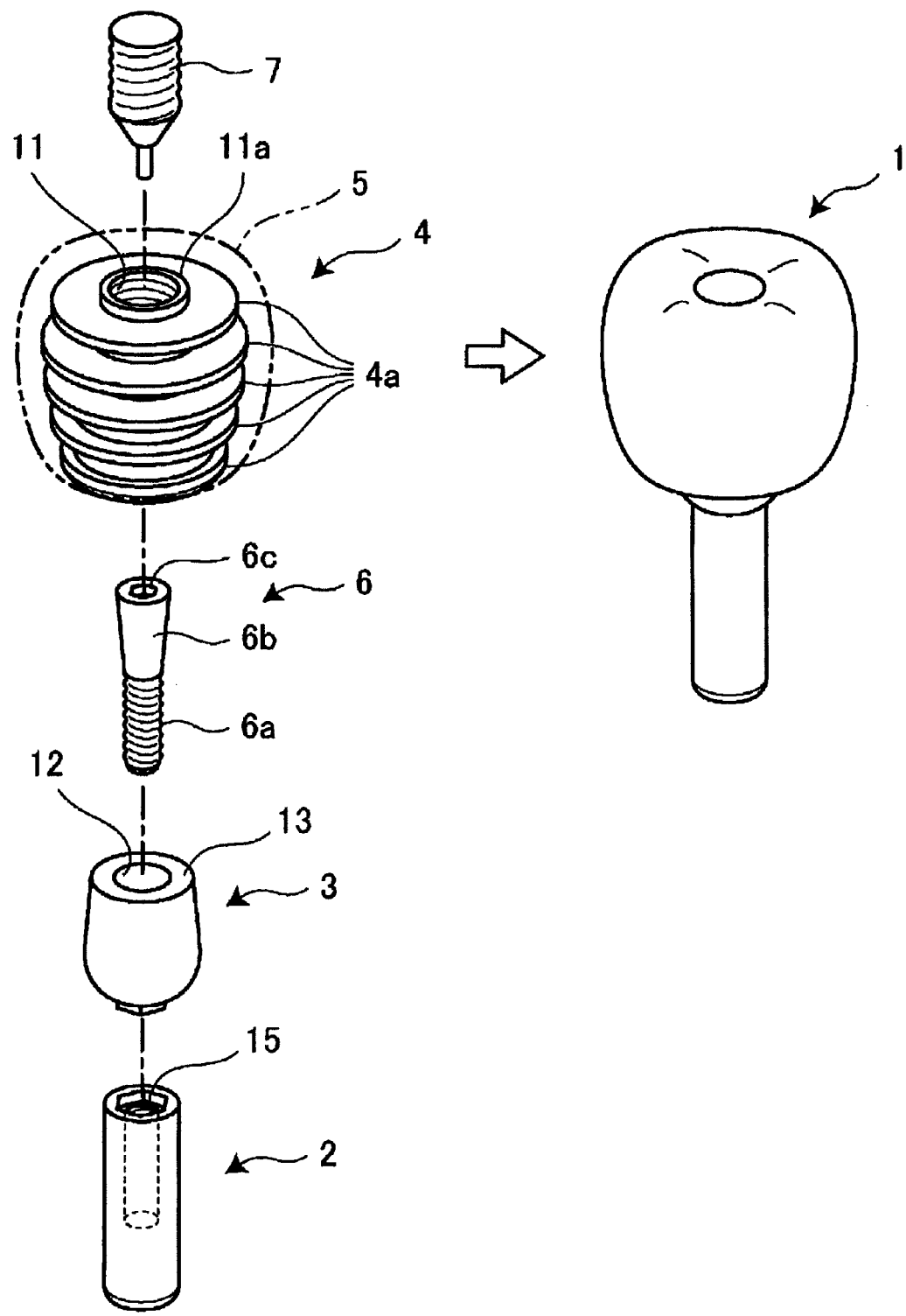
FIG. 2 is an exploded perspective view showing the dental implant structure of the embodiment.

As shown in FIG. 1 and FIG. 2, the dental implant structure 1 of this embodiment is constituted of a fixture 2 which is embedded into a jaw bone B, an abutment 3 which is placed on and fixed to an upper portion of the fixture 2, an artificial tooth base 4 which is placed on and fixed to an upper portion of the abutment 3, and an artificial tooth 5 which is mounted on the artificial tooth base 4.

In addition, an outer peripheral surface of the abutment 3 and an inner peripheral surface of a fitting hole 14 formed in the artificial tooth base 4 are respectively formed into tapered surfaces which correspond to each other so that the abutment 3 and the artificial tooth base 4 are brought into close contact with each other. In this manner, both the abutment 3 and the artificial tooth base 4 are configured to be detachably fitted to each other by way of the taper fitting structure 10. Further, a female threaded hole 11 which is vertically formed in the artificial tooth base 4 has a larger diameter than a male screw penetration hole 12 which is vertically formed in the abutment 3 as a vertical hole thus forming a stepped portion 13 constituted of an upper surface of the abutment 3 on a boundary between the female threaded hole 11 and the male screw penetration hole 12 which are communicated with each other.

Further, the male screw penetration hole 12 formed in the abutment 3 in a penetrating manner is tapered in an expanded manner such that a diameter of the hole 12 is gradually increased upwardly.

Further, the fixture 2 which is embedded in the jaw bone B and the abutment 3 which is configured to place and mount the artificial tooth 5 on the upper portion thereof are contiguously connected to each other as an integral body by way of a male screw rod 6. An upper half portion of the male screw rod 6 has an upwardly enlarged tapered shape which conforms with a shape of the tapered male screw penetration hole 12 formed in the abutment 3 in a penetrating manner. Here, a hexagonal recessed portion is formed on a top portion of the fixture 2 which constitutes one part of the integral body, and a hexagonal projecting portion is formed on a lower portion of the abutment 3 which constitutes the other part of the integral body. The projecting portion of the abutment 3 is detachably fitted into the recessed portion of the fixture 2.

As shown in FIG. 1 and FIG. 2, the abutment 3 is formed into a substantially bowl shape, and the male screw penetration hole 12 is formed in an upper surface of the abutment 3 which constitutes the stepped portion 13. However, the abutment 3 is not limited to such a constitution and various modifications can be adopted.

Figure 3:
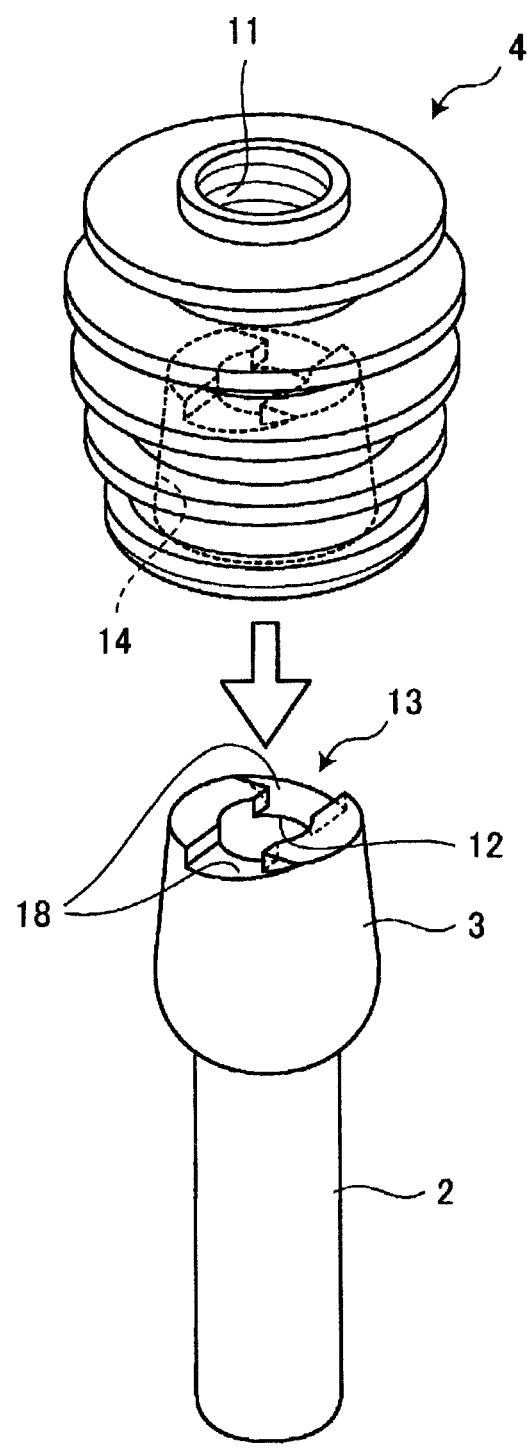
FIG. 3 is an exploded perspective view showing a modification of an abutment and an artificial tooth base.
Figure 4:
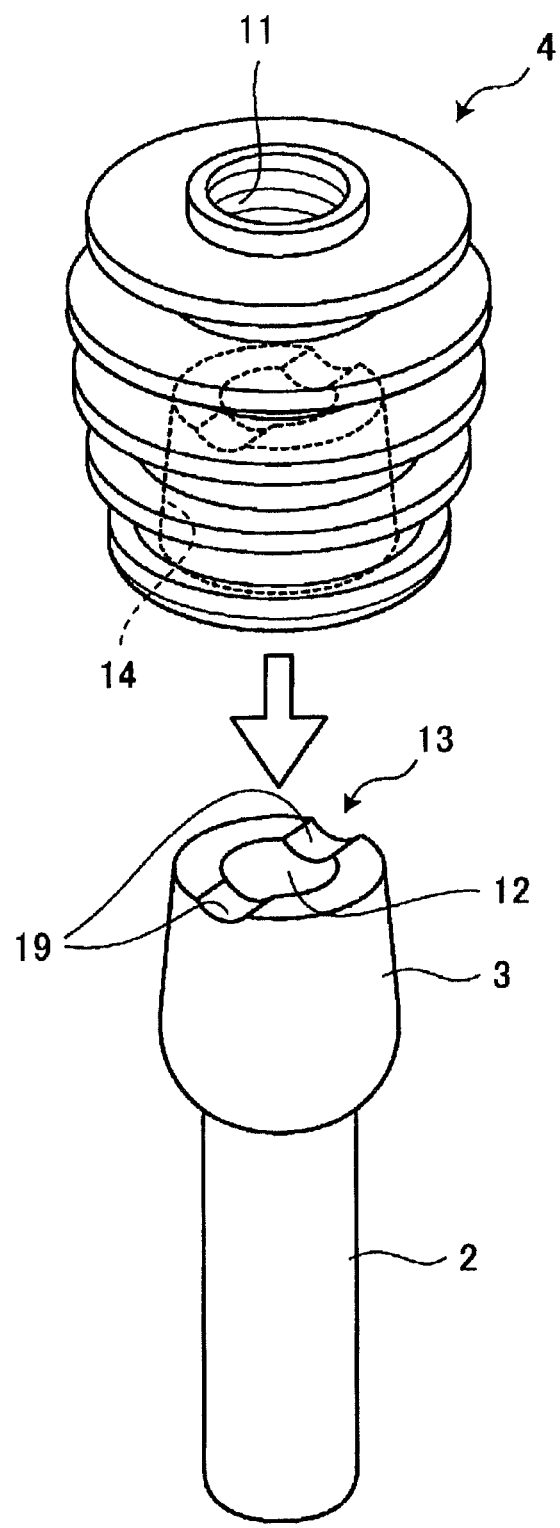
FIG. 4 is an exploded perspective view showing a modification of an abutment and an artificial tooth base.

A modification of the dental implant structure is explained in conjunction with FIG. 3 and FIG. 4. The modification of the dental implant structure shown in FIG. 3 and FIG. 4 differs from the above-mentioned dental implant structure with respect to a shape of the stepped portion 13 which is formed of the upper surface of the abutment 3.

That is, as shown in FIG. 3, on the stepped portion 13 of the abutment 3, in addition to the male screw penetration hole 12 formed in a center portion of the upper portion of the abutment 3, groves 18 are formed by cutting away portions of a periphery of the upper surface in a tapered manner in cross section. Further, a fitting hole 14 formed in the artificial tooth base 4 has a shape symmetrical with a shape of the stepped portion 13.

By forming the stepped portion 13 into such a shape, when the artificial tooth base 4 is fitted on the abutment 3 due to the threaded engagement, it is possible to position the artificial tooth base 4 in a state where a front surface and a rear surface of the artificial tooth base 4 are distinguished from each other.

Next, as shown in FIG. 4, on the stepped portion 13 of the abutment 3, in addition to the male screw penetration hole 12 formed in a center portion of the upper portion of the abutment 3, recessed portions 19 are formed by cutting away portions of a periphery of the upper surface in a semicircular columnar shape. Further, a fitting hole 14 formed in the artificial tooth base 4 has a shape symmetrical with a shape of the stepped portion 13.

By forming the stepped portion 13 into such a shape, when the artificial tooth base 4 is fitted on the abutment 3, it is possible to position the artificial tooth base 4 in a state where a front surface and a rear surface of the artificial tooth base 4 are distinguished from each other.

In this embodiment, the stepped portion 13 is constituted such that the female threaded hole 11 formed in the artificial tooth base 4 has the larger diameter than the male screw penetration hole 12 formed in the abutment 3. However, the stepped portion 13 may be formed such that both the female threaded hole 11 and the male screw penetration hole 12 have the substantially same diameter. For example, the male screw penetration hole 12 having a perfect circular shape as viewed in a plan view and having a straight shape in cross section is slightly formed into an approximately elliptical shape as viewed in a plan view by caulking an upper-surface opening portion of the abutment 3. Further, a diameter of the female threaded hole 11 formed in the artificial tooth base 4 is set substantially equal to a diameter of a long-axis corresponding portion of the upper-surface opening portion having a substantially elliptical circular shape in the male screw penetration hole 12. Due to such a constitution, it is possible to form a stepped portion 13 constituted of an upper surface of the abutment 3 on a boundary between the female threaded hole 11 and the male screw penetration hole 12 which are communicated with each other. Accordingly, also in this case, in removing the artificial tooth base 4 from the abutment 3, the artificial tooth base 4 can be removed from the abutment 3 by bringing a flat portion Q3 of a separation male screw jig Q into contact with the stepped portion of the abutment 3.

Here, a length of the male screw rod 6 may be set shorter than the length of the male screw rod 6 described in the above-mentioned example so as to allow the removal of the male screw rod 6 from the fixture 2 by making use of a stroke between an upper end of the male screw rod 6 and the upper surface opening portion having a substantially elliptical-shaped opening in a threadedly engaged state.

Figure 5:
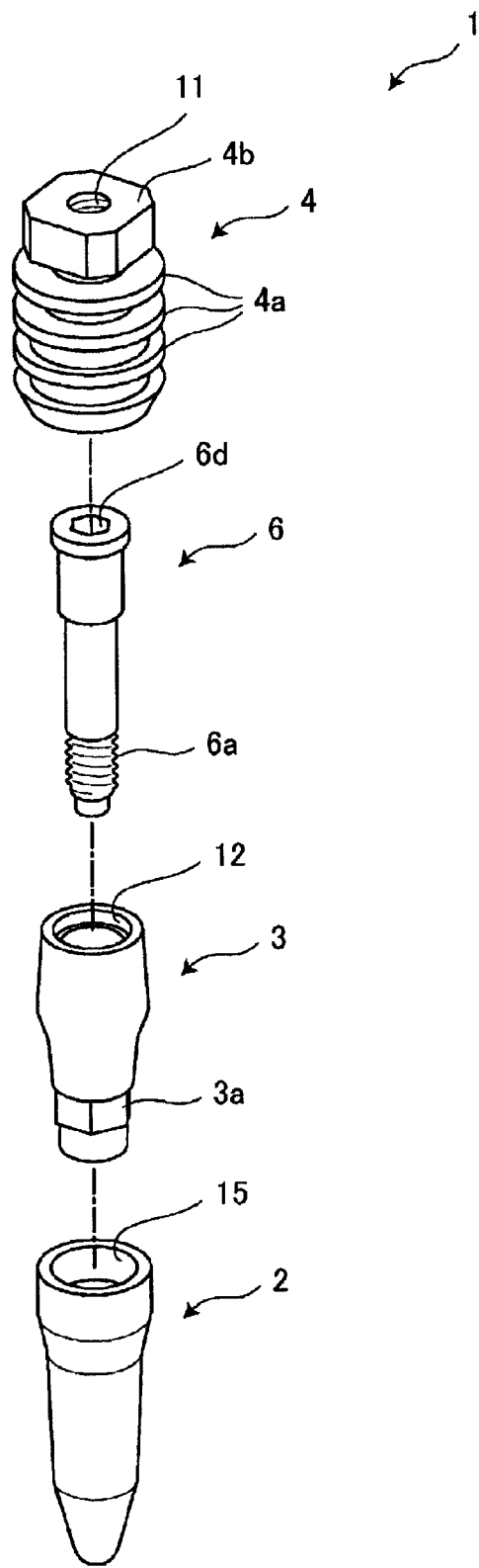
FIG. 5 is an exploded perspective view showing a modification of the dental implant structure of the embodiment.
Figure 6:
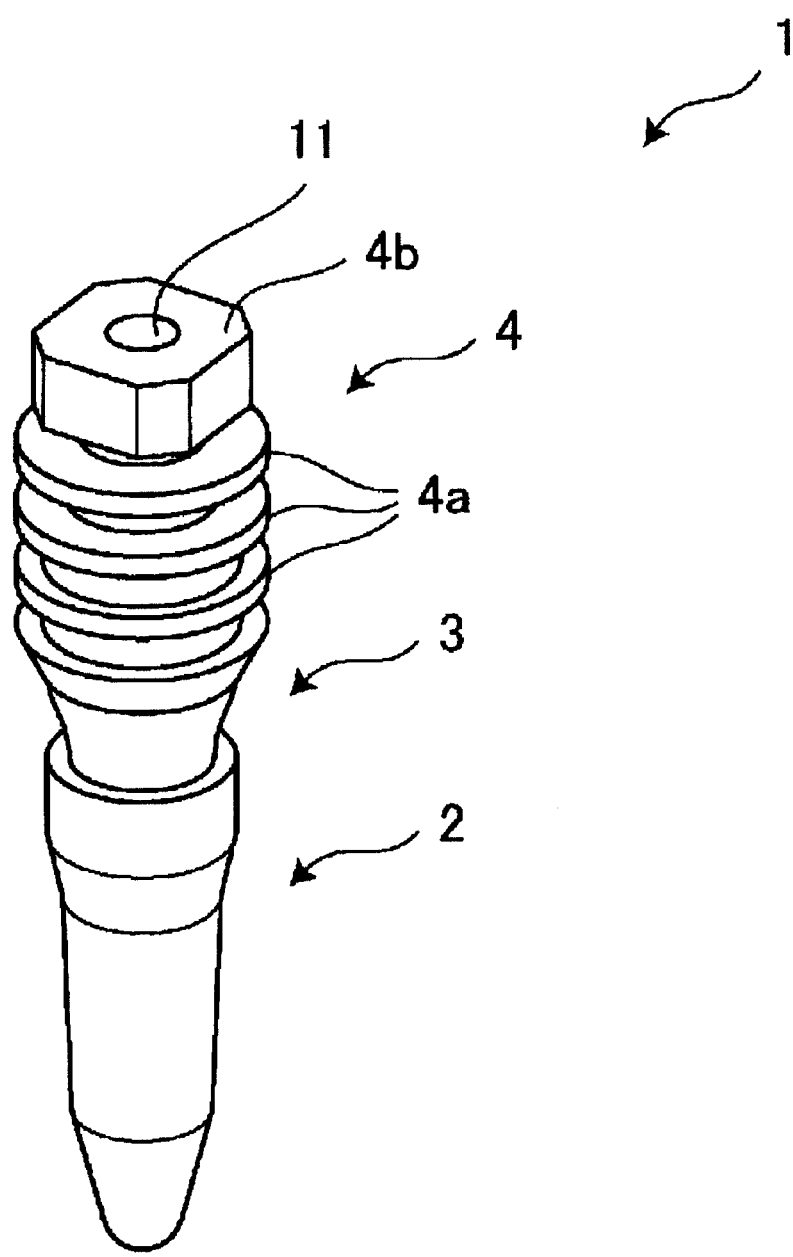
FIG. 6 is an explanatory view showing a modification of the dental implant structure of the embodiment.
Figure 7:
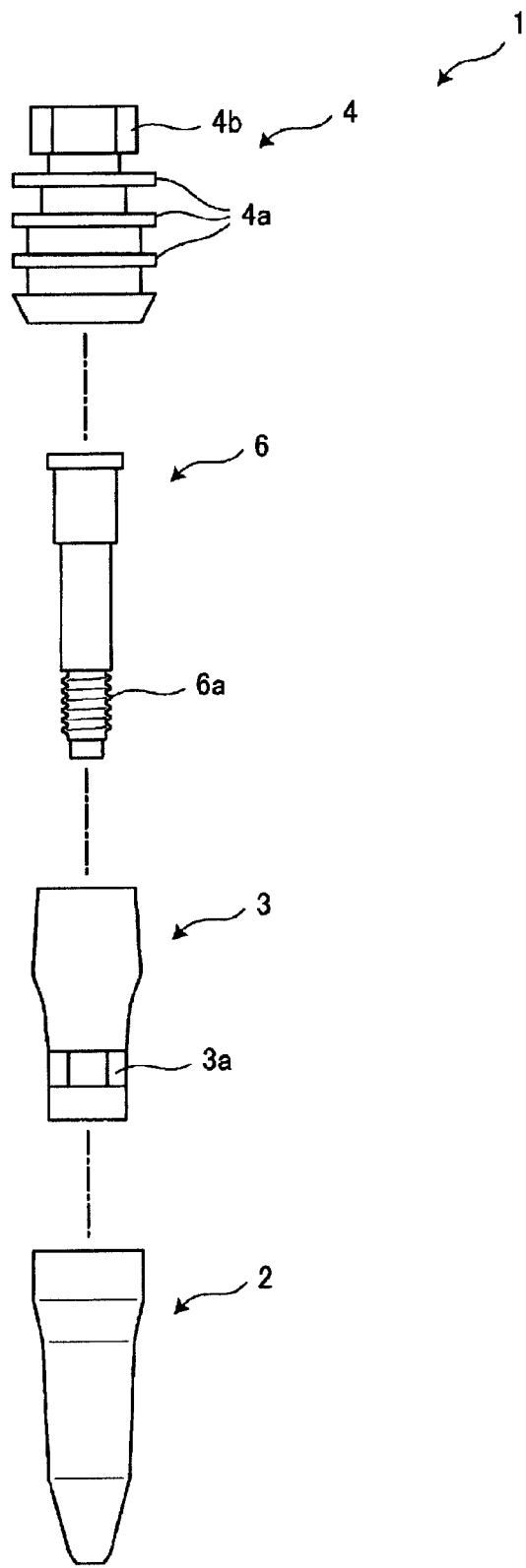
FIG. 7 is an exploded front view showing a modification of the dental implant structure of the embodiment.
Figure 8:
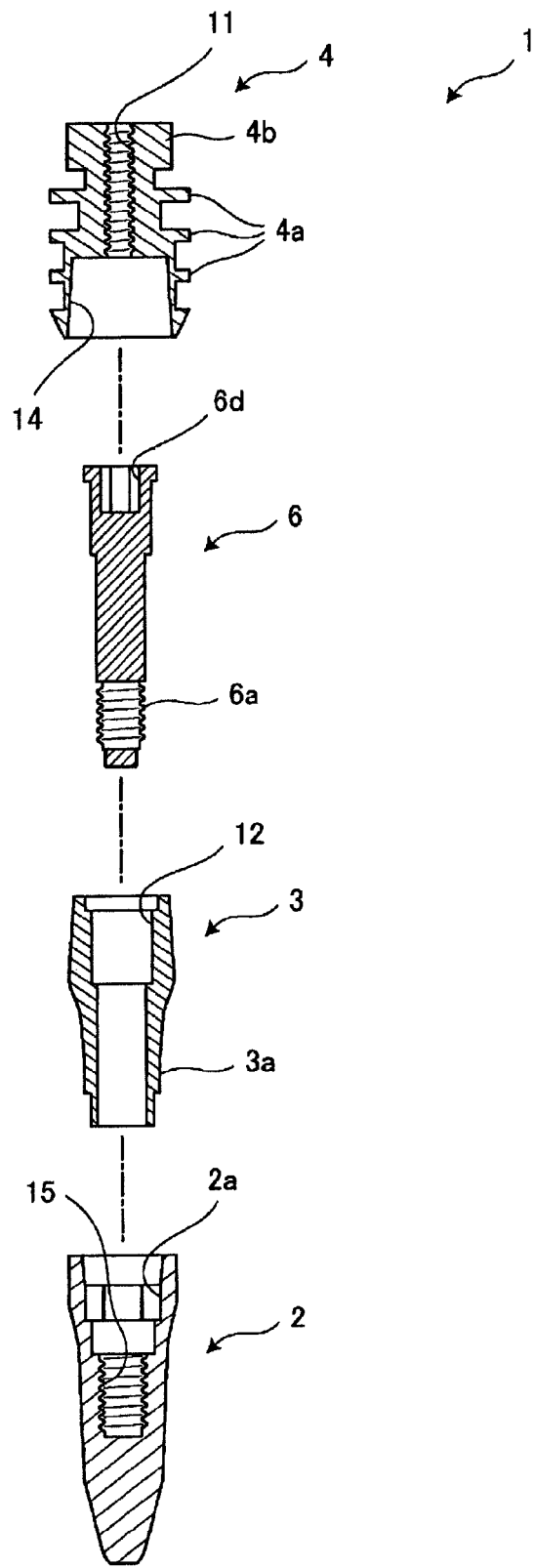
FIG. 8 is an exploded cross-sectional view showing a modification of the dental implant structure of the embodiment.
Figure 9:
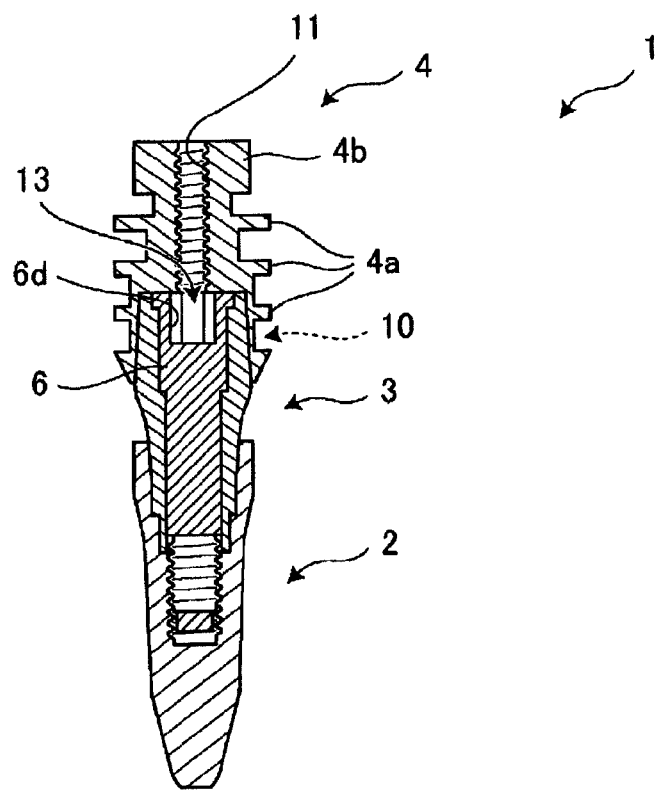
FIG. 9 is a cross-sectional view showing a modification of the dental implant structure of the embodiment.
Figure 10:
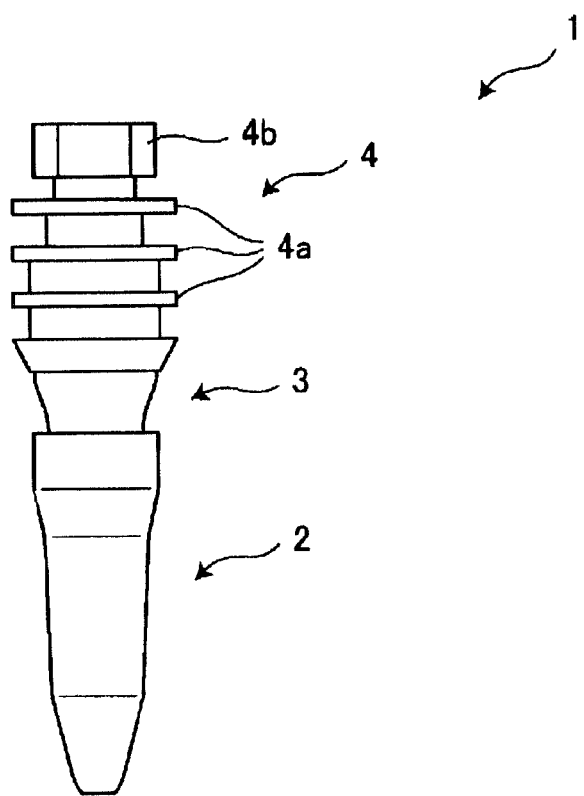
FIG. 10 is a front view showing a modification of the dental implant structure of the embodiment.

Further, a modification of the dental implant structure is explained in conjunction with FIG. 5 to FIG. 10. The constitutional parts identical with the parts of the above-mentioned dental implant structure are given same symbols and their repeated explanation is omitted. FIG. 5 is an exploded perspective view showing the modification of the dental implant structure according to this embodiment. FIG. 6 is an explanatory view showing the modification of the dental implant structure according to this embodiment. FIG. 7 is an exploded front view showing the modification of the dental implant structure according to this embodiment. FIG. 8 is an exploded cross-sectional view showing the modification of the dental implant structure according to this embodiment. FIG. 9 is a cross-sectional view showing the modification of the dental implant structure according to this embodiment. FIG. 10 is a front view showing the modification of the dental implant structure according to this embodiment.

As shown in FIG. 5 to FIG. 10, the dental implant structure 1 is constituted of a fixture 2 which is embedded into a jaw bone, an abutment 3 which is placed on and fixed to an upper portion of the fixture 2, an artificial tooth base 4 which is placed on and fixed to an upper portion of the abutment 3, and an artificial tooth 5 which is mounted on the artificial tooth base 4.

In addition, an outer peripheral surface of the abutment 3 and an inner peripheral surface of a fitting hole 14 formed in the artificial tooth base 4 (see FIG. 8) are respectively formed into tapered surfaces which correspond to each other so that the abutment 3 and the artificial tooth base 4 are brought into close contact with each other. In this manner, both the abutment 3 and the artificial tooth base 4 are configured to be detachably fitted to each other by way of the taper fitting structure 10. Further, a female threaded hole 11 which is vertically formed in the artificial tooth base 4 has a smaller diameter than a male screw penetration hole 12 which is vertically formed in the abutment 3 thus forming a stepped portion 13 constituted of an upper surface of the abutment 3 and a hexagonal hole 6*d* formed in a male screw rod 6 on a boundary between the female threaded hole 11 and the male screw penetration hole 12 which are communicated with each other.

The male screw rod 6 has a shape which is formed by integrally joining columns whose diameters differ from each other and are gradually increased upwardly. That is, a male threaded portion 6*a* which is threadedly engaged with a female threaded hole 15 formed in the fixture 2 is formed on a lower portion of the male screw rod 6, a middle portion of the male screw rod 6 is formed into a columnar shape whose diameter is gradually increased upwardly, and an upper portion of the male screw rod 6 is formed into a disc shape having a largest diameter. A hexagonal threaded hole 6*d* is formed in a center portion of the upper portion of the male screw rod 6.

Further, the fixture 2 which is embedded in the jaw bone B and the abutment 3 which is configured to place and mount the artificial tooth 5 on the upper portion thereof are contiguously connected to each other as an integral body by way of a male screw rod 6. A hexagonal recessed portion 2a is formed in the inside of the fixture 2 which constitutes one part of the integral body, and a hexagonal projecting portion 3a is formed on a lower portion of the abutment 3 which constitutes the other part of the integral body. The projecting portion 3a of the abutment 3 is detachably fitted into the recessed portion 2a of the fixture 2.

An octagonal head portion 4b is formed on an upper portion of the artificial tooth base 4, and a plurality of ring-shaped engaging projections 4a are formed on a lower portion of the artificial tooth base 4. In a state where the fixture 2, the abutment 3, the male screw rod 6 and the artificial tooth base 4 are embedded in the jaw bone B as an integral body, by mounting a wrench on the head portion 4b of the artificial tooth base 4 and by rotating the wrench, the fixture 2 can be further embedded in the jaw bone B thus enabling the fine adjustment of an embedding depth of the fixture 2.

Figure 11:
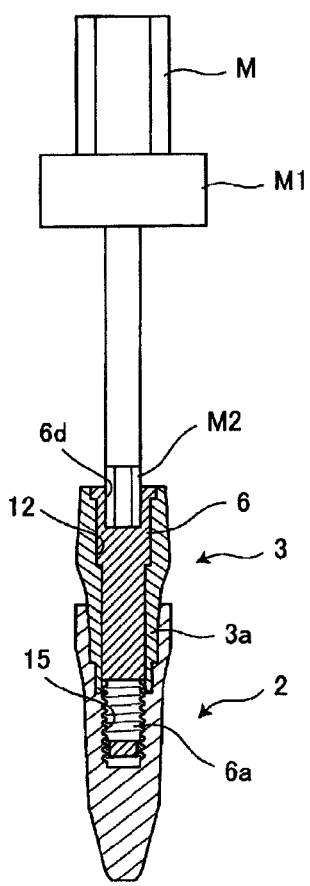
FIG. 11 is an explanatory view showing the steps of the manner of using a male screw fastening jig.

As shown in FIG. 11, in mounting the abutment 3 on the fixture 2, the abutment 3 is mounted in the female threaded hole 15 formed in the fixture 2, the male screw rod 6 is inserted through the male screw penetration hole 12 formed in the abutment 3, and a male threaded portion 6a of the male screw rod 6 is threadedly engaged with the female threaded hole 15 formed in the fixture 2. Here, by fitting the male screw fastening jig M which is prepared separately in the hexagonal hole 6d which constitutes a portion of the stepped portion formed on the male screw rod upper end surface 6c of the male screw rod 6 and by rotating the male screw fastening jig M, the abutment 3 is integrally mounted on the fixture 2.

Here, the male screw fastening jig M is configured such that a driver distal end portion M2 has a hexagonal shape and is detachably fitted in the hexagonal hole 6d formed in the male screw rod 6, and a grip handle portion M1 is formed on a proximal end side of the male screw fastening jig M.

Figure 12:
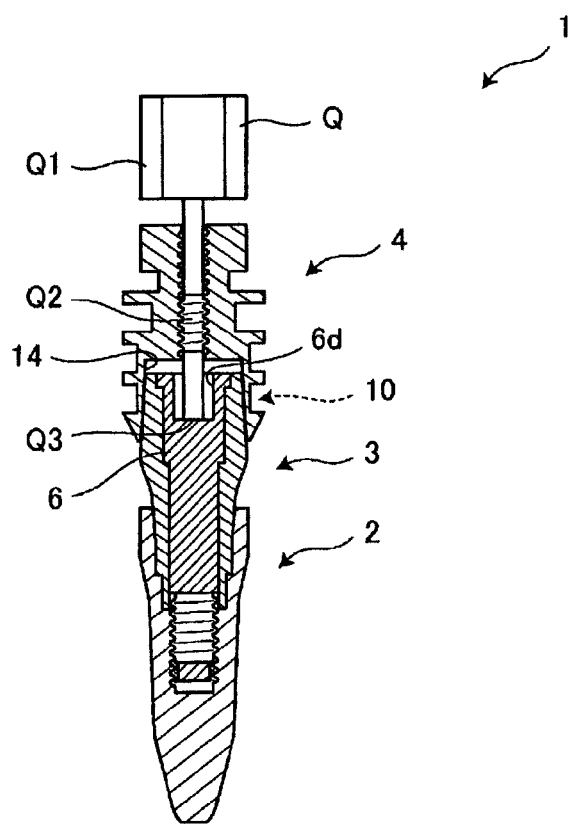
FIG. 12 is an explanatory view showing the steps of the manner of using of an artificial tooth base removing jig.

As shown in FIG. 12, in releasing a taper fitting state between the abutment 3 and the artificial tooth base 4, the separation male screw jig Q is threadedly engaged with and is advanced through the female threaded hole 11 formed in the upper portion of the artificial tooth base 5 so that a distal end of the separation male screw jig Q reaches the bottom surface of the hexagonal hole 6d formed in the male screw rod 6 which constitutes a portion of the stepped portion. When the separation male screw jig Q is further threadedly inserted into the female threaded hole 11, the artificial tooth base 4 is separated from the abutment 3. Here, a gap is formed by the abutment 3, the upper end surface of the male screw rod 6 and the fitting hole 14 formed in the artificial tooth base 4. Due to a removal force generated by such an operation, the abutment 3 and the artificial tooth base 4 which are engaged with each other in taper fitting can be easily detached from each other.

Here, in the above-mentioned dental implant structure, the abutment 3 and the fixture 2 are constituted as separate bodies from each other and are integrally connected with each other using the male screw rod 6. However, it is not always necessary to constitute these parts as separate bodies, and may be formed of an integral body preliminarily.

The explanation is made hereinafter with respect to an embodiment of the dental implant structure for denture or orthodontics where the integral structure formed of the above-mentioned abutment 3 and fixture 2 is used as a support anchor, the support anchor is embedded into a jaw bone, and an artificial tooth base for denture or orthodontics is placed on and fixed to an upper portion of the support anchor.

[Dental Implant Structure for Denture]

The dental implant structure for denture is explained in conjunction with FIG. 13 to FIG. 18. Here, the dental implant structure for denture described hereinafter is also applicable to the above-mentioned dental implant structure and the dental implant structure for a crowned and bridged artificial tooth.

Figure 13:
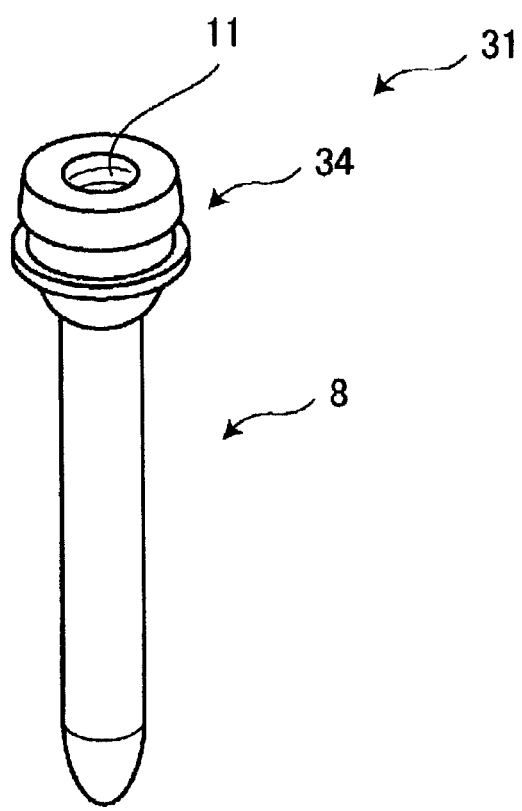
FIG. 13 is an explanatory view showing the dental implant structure for denture.
Figure 14:
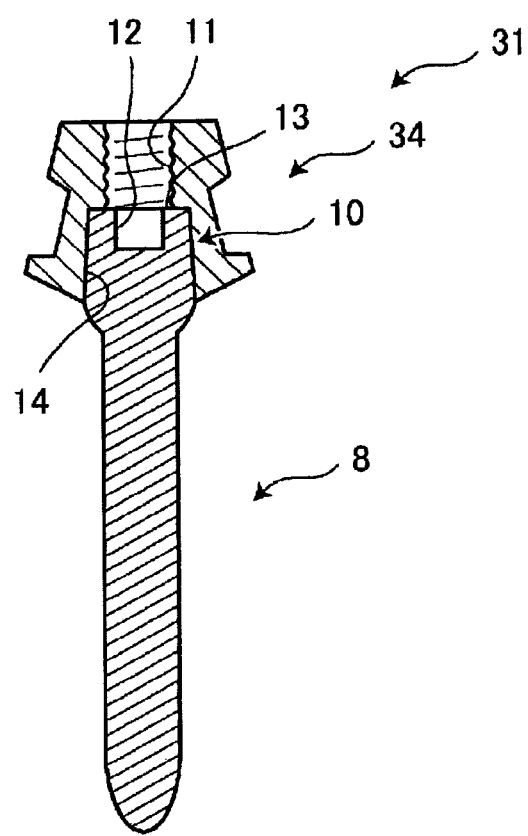
FIG. 14 is a cross-sectional view showing the dental implant structure for denture.

As shown in FIG. 13 and FIG. 14, the dental implant structure 13 for denture is configured such that a support anchor 8 is embedded into a jaw bone B, and an artificial tooth base 34 for denture is placed on and fixed to an upper portion of the support anchor 8.

Further, an upper outer peripheral surface of the support anchor 8 and an inner peripheral surface of a fitting hole 14 formed in an artificial tooth base 34 are respectively formed into tapered surfaces which correspond to each other so that the support anchor 8 and the artificial tooth base 34 for denture are brought into close contact with each other. That is, both the support anchor 8 and the artificial tooth base 34 for denture are configured to be detachably fitted to each other by way of the taper fitting structure 10. Further, a female threaded hole 11 which is vertically formed in the artificial tooth base 34 has a larger diameter than a male screw penetration hole 12 which is vertically formed in the support anchor 8 as a vertical hole thus forming a stepped portion 13 constituted of an upper surface of the support anchor 8 on a boundary between the female threaded hole 11 and the male screw penetration hole 12 which are communicated with each other.

An upper portion of the support anchor 8 is formed into a substantially bowl shape and a lower portion of the support anchor 8 is formed into a screw shape, and the male screw penetration hole 12 is formed in a center portion of the upper surface of the support anchor 8 which constitutes the stepped portion 13.

The artificial tooth base 34 for denture has an outer shape which is formed by stacking rings having different diameters from below to above. A lower portion of the artificial tooth base 34 has an outer shape thereof formed into a ring shape with a large diameter, and a fitting hole is formed in a center portion of a bottom portion of the lower portion. Further, a middle portion which is contiguously connected to the lower portion has an outer shape thereof formed into a ring shape with a small diameter. An upper portion which is contiguously connected to the middle portion has an outer shape thereof formed into a ring shape with a middle diameter, and the male threaded hole 11 is formed in a center portion of the upper surface of the upper portion.

Figure 15:
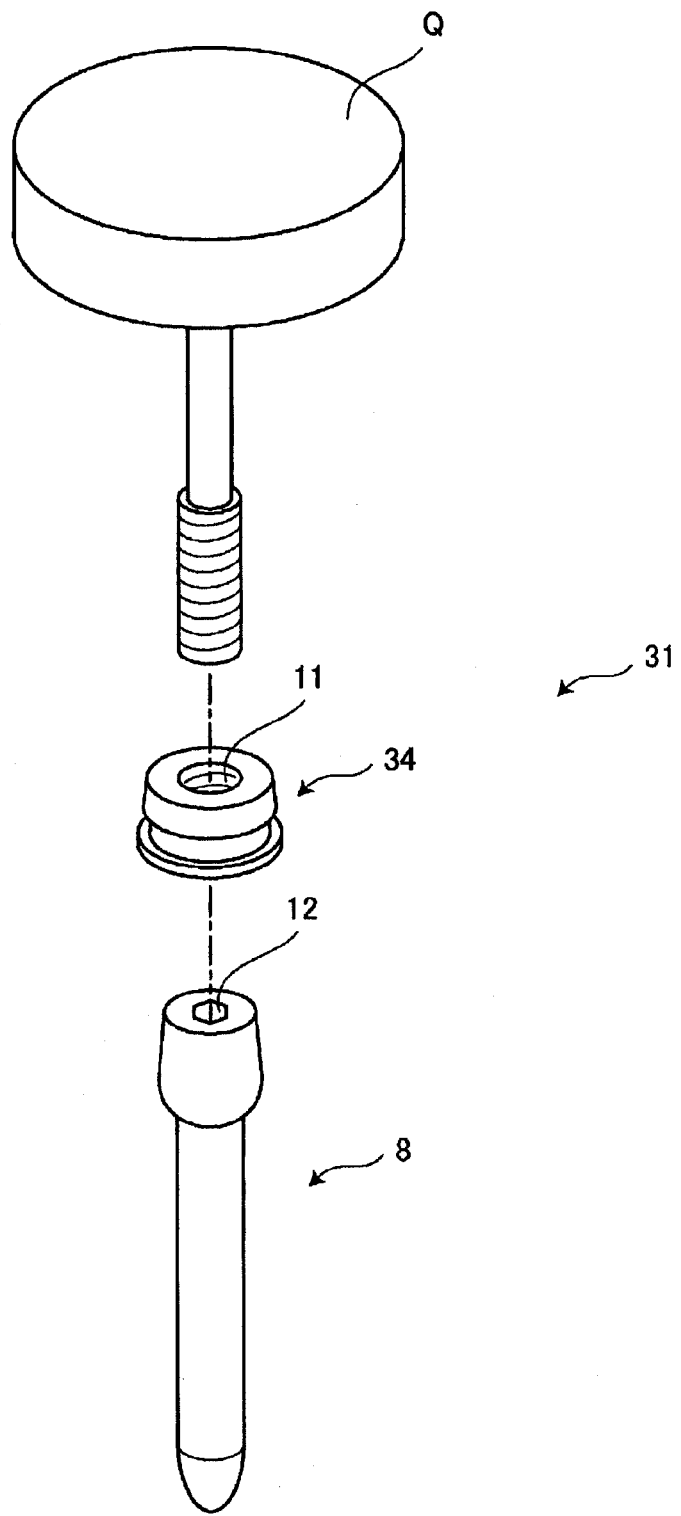
FIG. 15 is an exploded perspective view showing the dental implant structure for denture.

As shown in FIG. 15, to separate the artificial tooth base 34 for denture and the support anchor 8 which are engaged with each other in taper fitting temporarily from each other, a separation male screw jig Q which is prepared separately is used. That is, the separation male screw jig Q is threadedly engaged with the female threaded hole 11 formed in the artificial tooth base 34 through a start end of the female threaded hole 11, a distal end surface of the separation male screw jig Q is brought into pressure contact with the stepped portion 13 of the support anchor 8 and, with further rotation of the separation male screw jig Q, the support anchor 8 and the artificial tooth base 34 are separated from each other by making use of a pressure contact reaction force.

Figure 16:
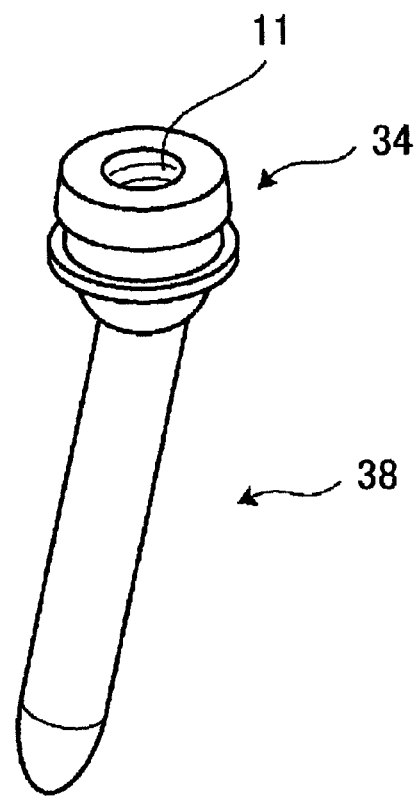
FIG. 16 is an explanatory view showing the dental implant structure for denture.
Figure 17:
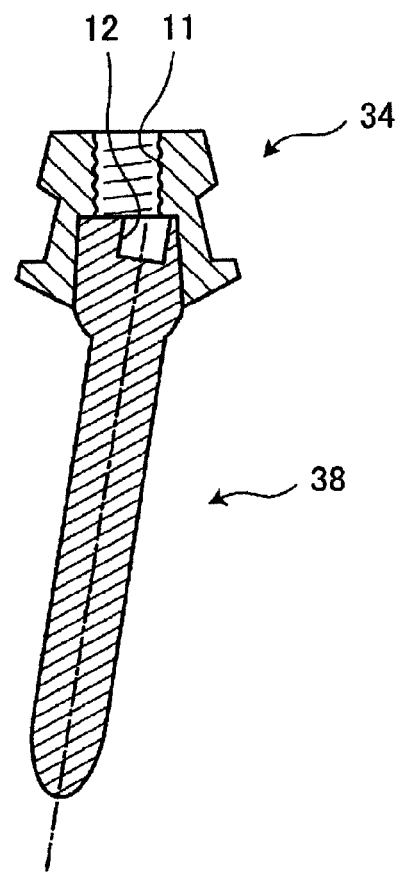
FIG. 17 is a cross-sectional view showing the dental implant structure for denture.

A support anchor 38 shown in FIG. 16 and FIG. 17 is used when it is necessary to embed the support anchor 38 obliquely with respect to a jaw bone B. An anchor portion of the support anchor 38 is connected to an upper portion of the support anchor 38 such that the anchor portion extends obliquely with respect to the upper portion. Further, a male screw penetration hole 12 is formed in an upper surface of the support anchor 38 such that an axis of the male screw penetration hole 12 is aligned with an axis of the anchor portion. Due to such a constitution, even when the support anchor 38 is embedded in a jaw bone obliquely, an upper surface of the upper portion of the support anchor 38 is held in a horizontal state.

Figure 18:
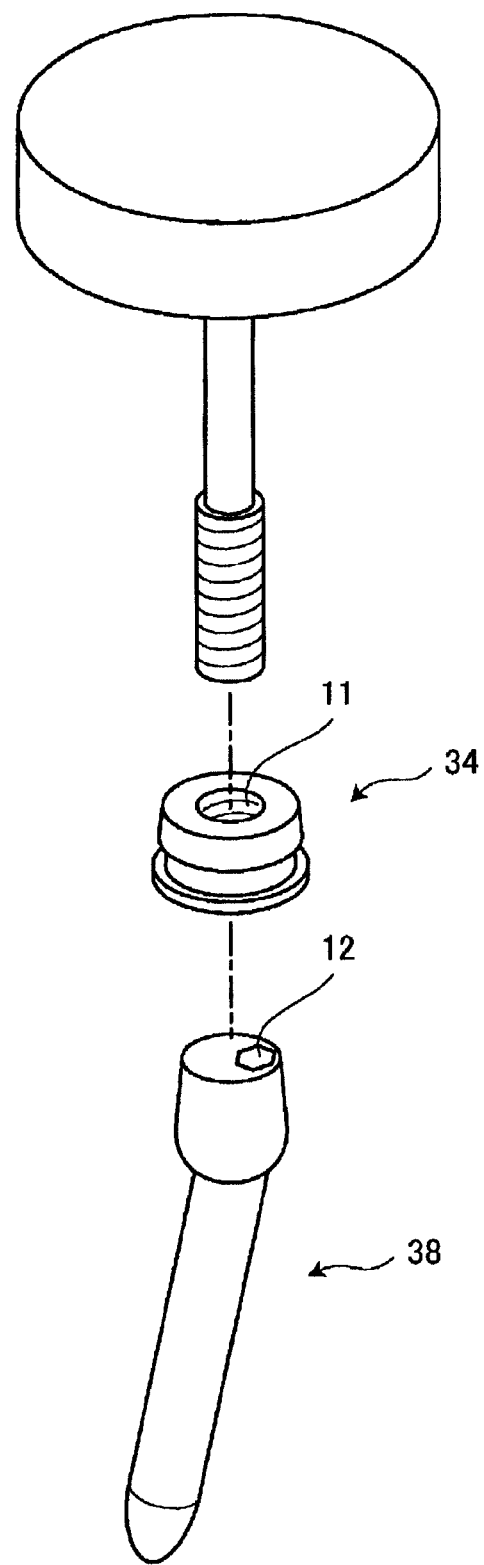
FIG. 18 is an exploded perspective view showing the dental implant structure for denture.

As shown in FIG. 18, to separate the support anchor 38 and the artificial tooth base 34 for denture which are engaged with each other in taper fitting once from each other, a separation male screw jig Q which is prepared separately is used. That is, the separation male screw jig Q is threadedly engaged with the female threaded hole 11 formed in the artificial tooth base 34 through a start end of the female threaded hole 11, a distal end surface of the separation male screw jig Q is brought into pressure contact with the stepped portion 13 of the support anchor 38 and, with further rotation of the separation male screw jig Q, the support anchor 38 and the artificial tooth base 34 are separated from each other by making use of a pressure contact reaction force.

Figure 54:
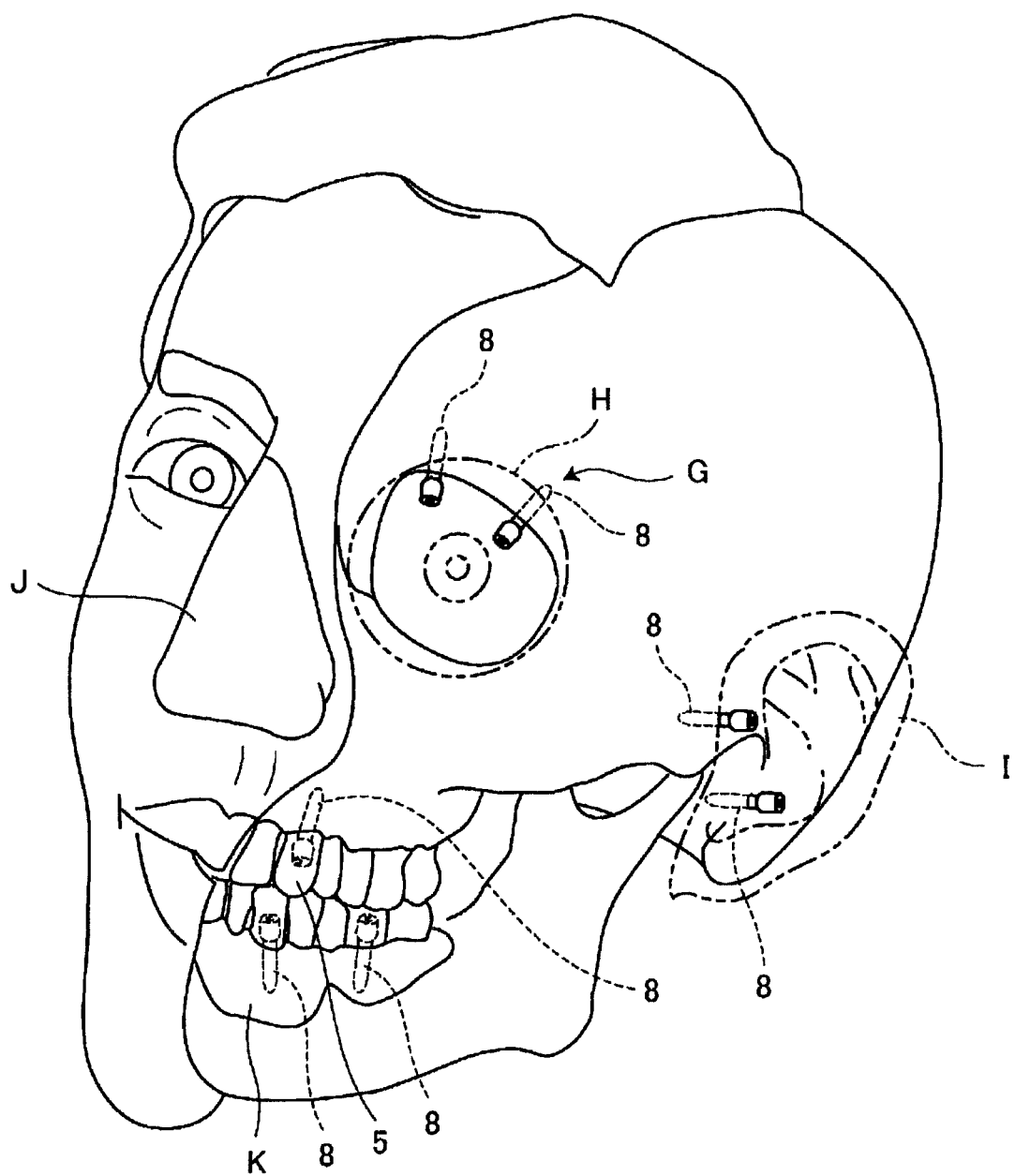
FIG. 54 is a perspective view showing a using state of the human-body implant structure.

By installing the above-mentioned dental implant structure 31 for denture in the inside of an oral cavity D of a patient, he can use a denture K within a short period (see FIG. 54).

[Modification of Dental Implant Structure for Denture]

Figure 19:
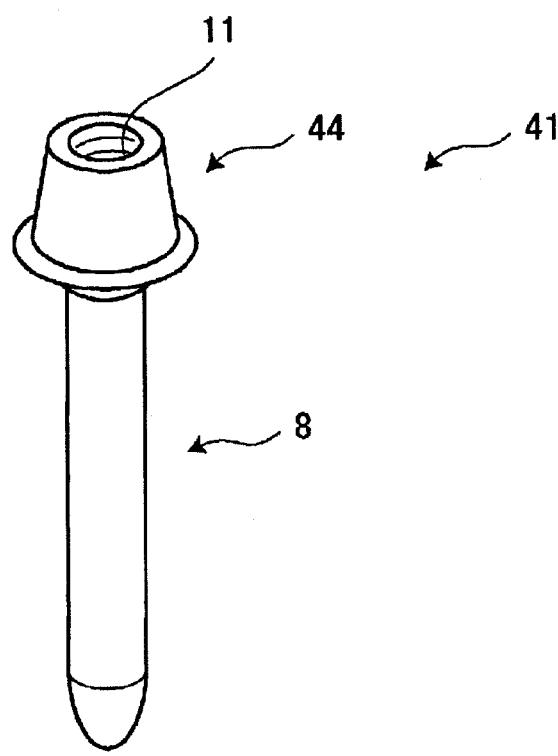
FIG. 19 is an explanatory view showing a modification of the dental implant structure for denture.
Figure 20:
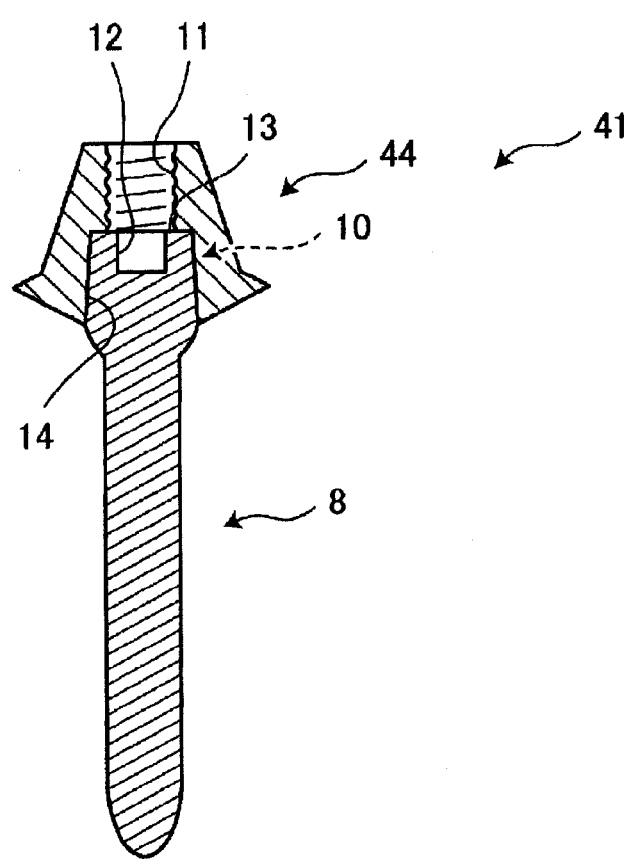
FIG. 20 is a cross-sectional view showing a modification of the dental implant structure for denture.
Figure 21:
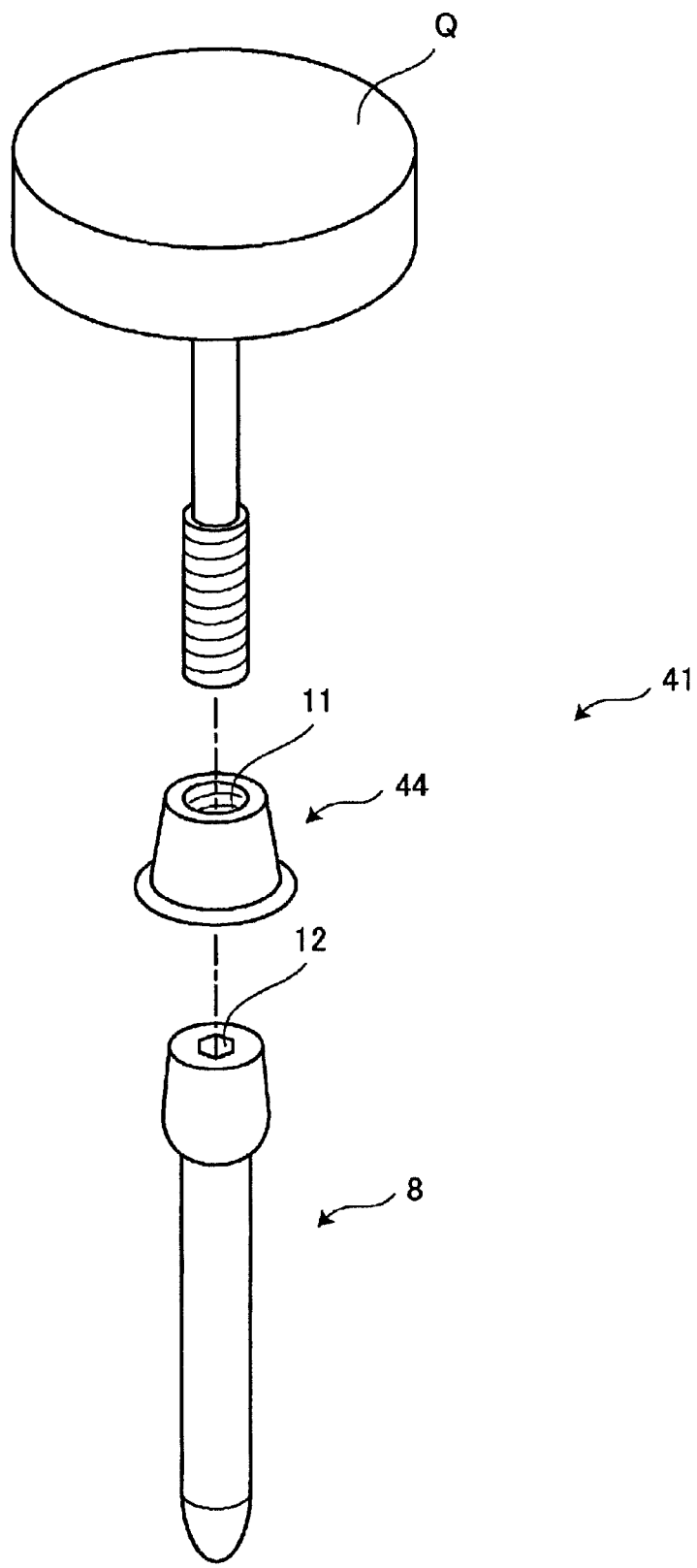
FIG. 21 is an exploded perspective view showing a modification of the dental implant structure for denture.

A modification of the dental implant structure for denture is explained in conjunction with FIG. 19 to FIG. 21. The modification of the dental implant structure for denture differs from the above-mentioned dental implant structure 31 for denture in an outer shape of the artificial tooth base 34 for denture.

As shown in FIG. 19 and FIG. 20, the outer shape of an artificial tooth base 44 for denture has an upper portion thereof formed into a frustoconical shape and has a lower portion thereof formed into a laterally extending oblong diamond shape in cross section.

By installing the above-mentioned dental implant structure 41 for denture in the inside of an oral cavity of a patient, he can start using a denture within a short period.

As shown in FIG. 21, to separate the support anchor 8 and the artificial tooth base 44 for denture which are engaged with each other in taper fitting once from each other, a separation male screw jig Q which is prepared separately is used. That is, the separation male screw jig Q is threadedly engaged with the female threaded hole 11 formed in the artificial tooth base 44 through a start end of the female threaded hole 11, a distal end surface of the separation male screw jig Q is brought into pressure contact with the stepped portion 13 of the support anchor 8, and with the further rotation of the separation male screw jig Q, the support anchor 8 and the artificial tooth base 44 are separated from each other by making use of a pressure contact reaction force.

The above-mentioned artificial tooth base 44 for denture has been explained on a premise that the artificial tooth base 44 is used for denture. However, the artificial tooth base 44 may be also used as a base for capping a crown on an artificial tooth for a single tooth.

[Dental Implant Structure for Orthodontic]

Figure 22:
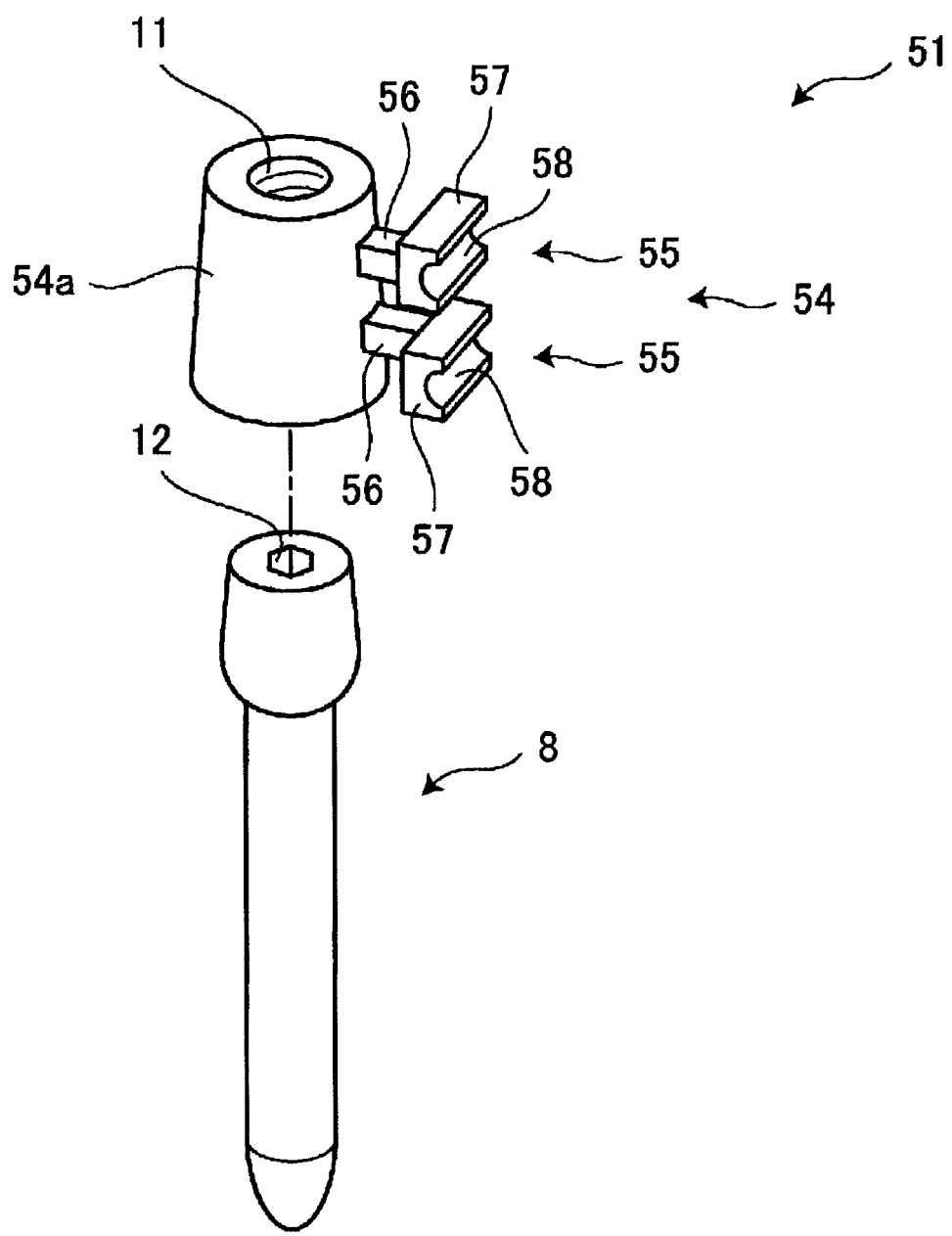
FIG. 22 is an exploded perspective view showing the dental implant structure for an orthodontic.
Figure 23:
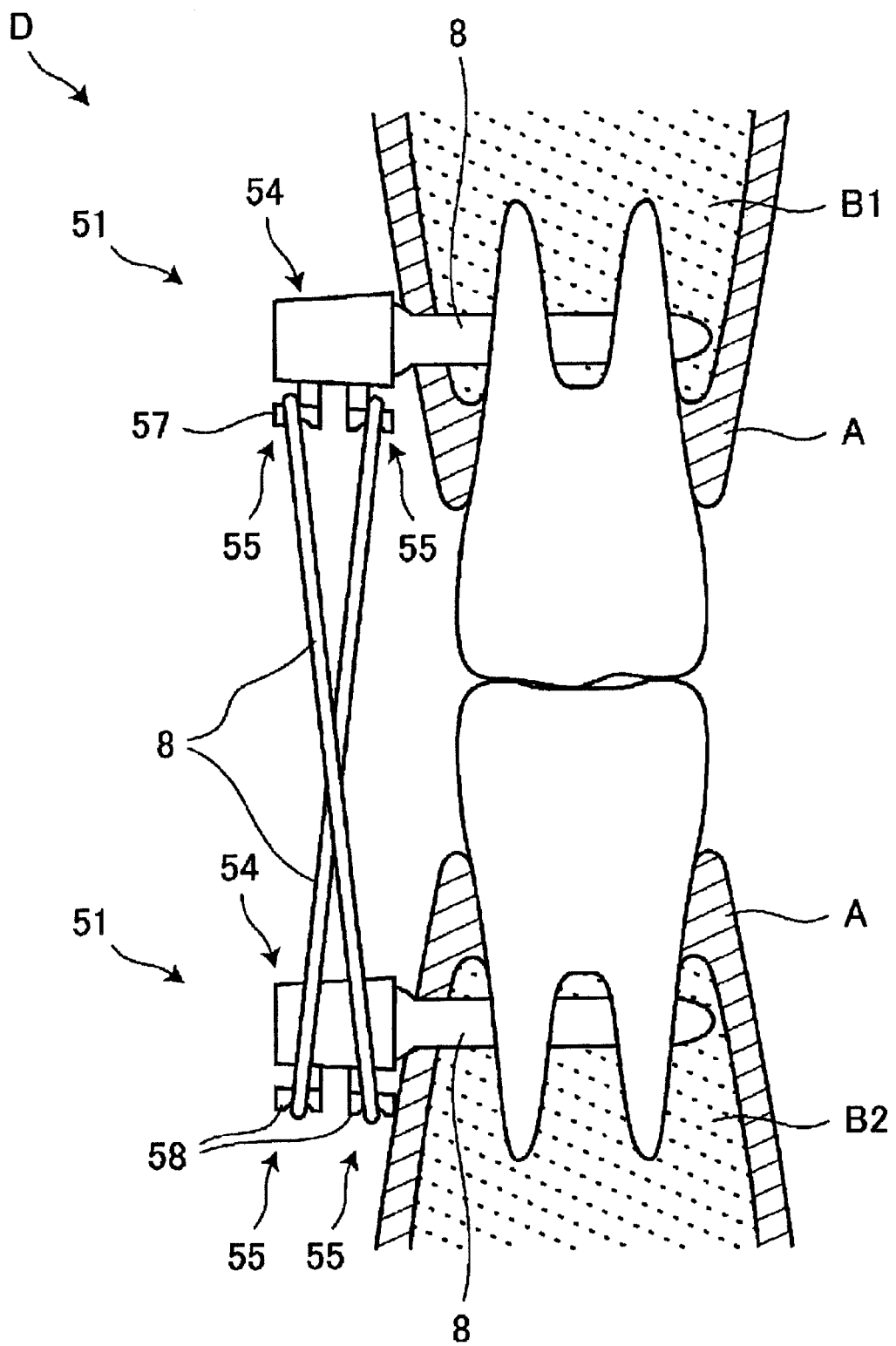
FIG. 23 is an explanatory view showing a using state of the dental implant structure for an orthodontic.

The dental implant structure for orthodontic is explained in conjunction with FIG. 22 and FIG. 23.

The dental implant structure 51 for orthodontic is configured such that support anchors 8 are embedded in upper and lower jaw bones B respectively and an artificial tooth base 54 for orthodontic is placed on and fixed to upper portions of the support anchors 8 respectively.

The artificial tooth base 54 for orthodontic is formed in a frustoconical shape, and wire engaging portions 55, 55 to be engaged with a dental wire 9 are arranged in parallel to each other in a projecting manner on an outer peripheral portion of the artificial tooth base 54. That is, each wire engaging portion 55 is formed in an L shape as viewed in a side view, and is constituted of a leg portion 56 which stands upright on an outer peripheral portion 54a and an engaging portion 57 which is formed on a distal end of the leg portion 56 and has a concave surface 58 which is formed by cutting away one surface of a rectangular shape.

As shown in FIG. 23, the support anchors 8, 8 are respectively embedded in the upper jaw bone B1 and the lower jaw bone B2 in an oral cavity D of a patient, the artificial tooth bases 54, 54 for orthodontic are engaged with upper portions of the support anchors 8, 8 by taper fitting, the dental wire 9 is extended between both artificial tooth bases 54, 54 so as to fix the upper and lower jaw bones B1, B2. That is, the dental wire 9 is engaged with a rear portion of the engaging portion 57 of the artificial tooth base 54 on the upper jaw side, is extended to the lower jaw bone B2, and is engaged with the concave surface 58 of the engaging portion 57 of the artificial tooth base 54 on the lower jaw side thus fixing the upper and lower jaw bones. By providing the wire engaging portions 55 having such structure, the dental wire 9 can be easily engaged in various modes thus shortening a time for mounting the dental implant structure 51 for orthodontic.

[Modification 1 of Dental Implant Structure for Orthodontic]

Figure 24:
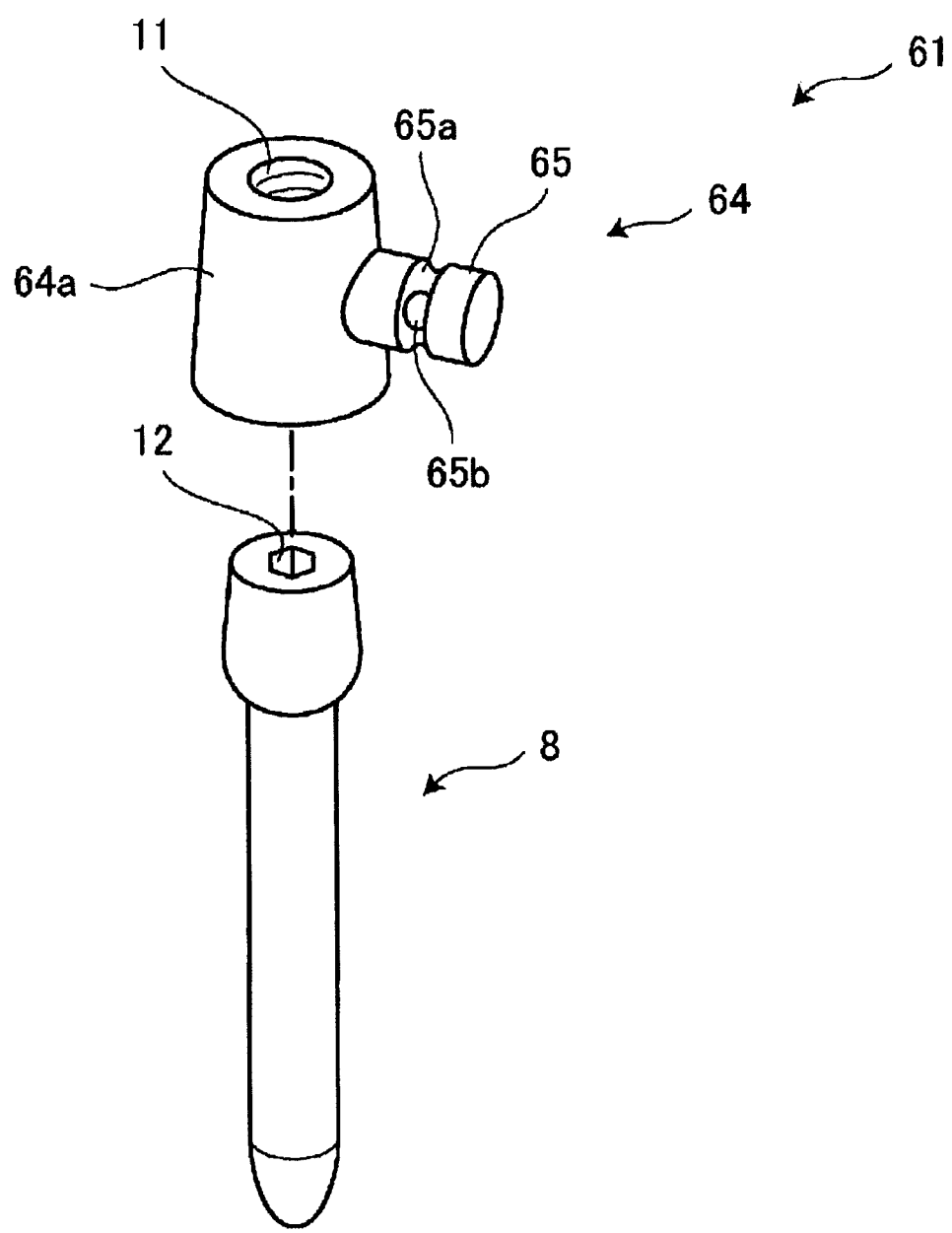
FIG. 24 is an exploded perspective view showing a modification 1 of the dental implant structure for an orthodontic.
Figure 25:
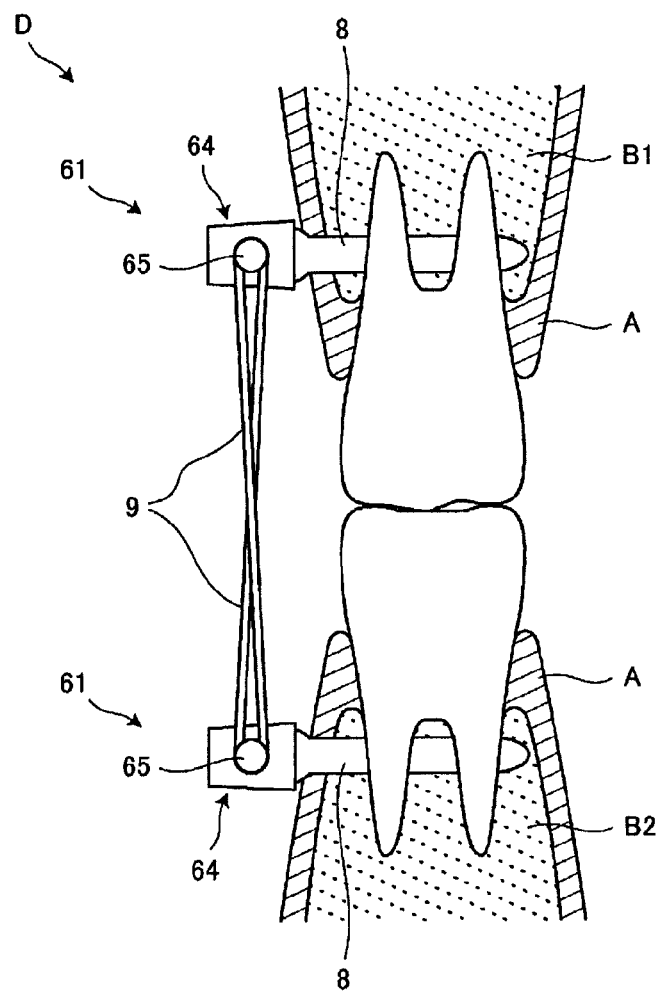
FIG. 25 is an explanatory view showing a using state of the modification 1 of the dental implant structure for an orthodontic.

The modification 1 of the dental implant structure for orthodontic is explained in conjunction with FIG. 24 and FIG. 25.

The modification 1 of the dental implant structure for orthodontic differs from the above-mentioned dental implant structure 51 for orthodontic in an outer shape of the artificial tooth base 54 for orthodontic.

An artificial tooth base 64 for orthodontic is formed in a frustoconical shape, and a columnar wire engaging portion 65 to be engaged with a dental wire 9 is arranged in a projecting manner on an outer peripheral portion 64a of the artificial tooth base 64. An engaging groove 65a is formed on a peripheral surface of the wire engaging portion 65, and a through hole 65b is formed in the engaging groove 65a.

As shown in FIG. 25, the support anchors 8, 8 are respectively embedded in the upper jaw bone B1 and the lower jaw bone B2 in an oral cavity D of a patient, the artificial tooth bases 64, 64 for orthodontic are engaged with upper portions of the support anchors 8, 8 in taper fitting, the dental wire 9 is extended between the columnar wire engaging portions 65, 65 of both artificial tooth bases 64, 64 so as to fix the upper and lower jaw bones B1, B2. That is, while the dental wire 9 is used in a mode where the dental wire 9 is engaged with the engaging groove 65a formed on the wire engaging portion 65, the dental wire 9 may be used in a mode where the dental wire 9 penetrates the through hole 65b so as to fix the upper and lower jaw bones. By providing the wire engaging portions 65 having such structure, the dental wire 9 can be easily engaged.

[Modification 2 of Dental Implant Structure for Orthodontic]

Figure 26:
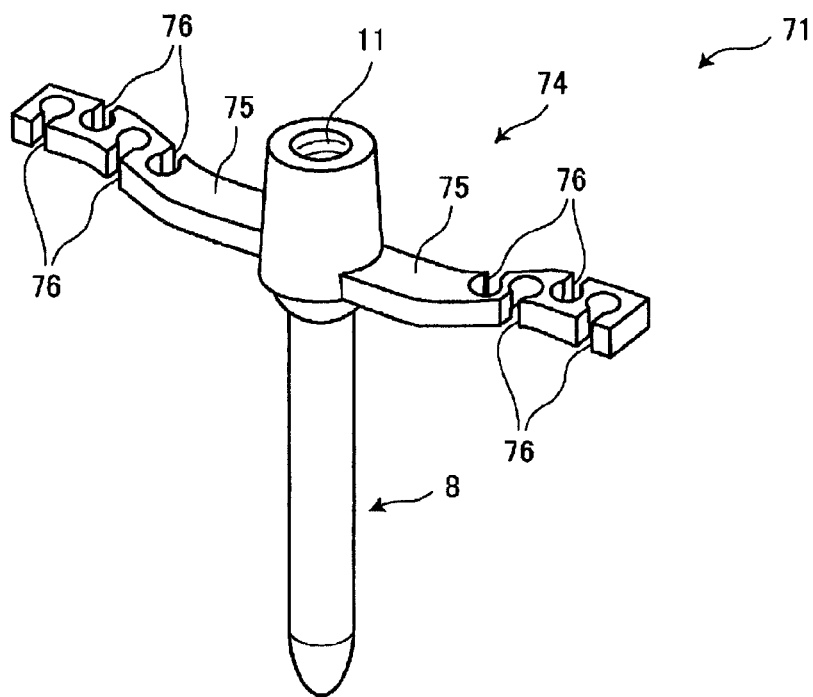
FIG. 26 is an exploded perspective view showing a modification 2 of the dental implant structure for an orthodontic.
Figure 27:
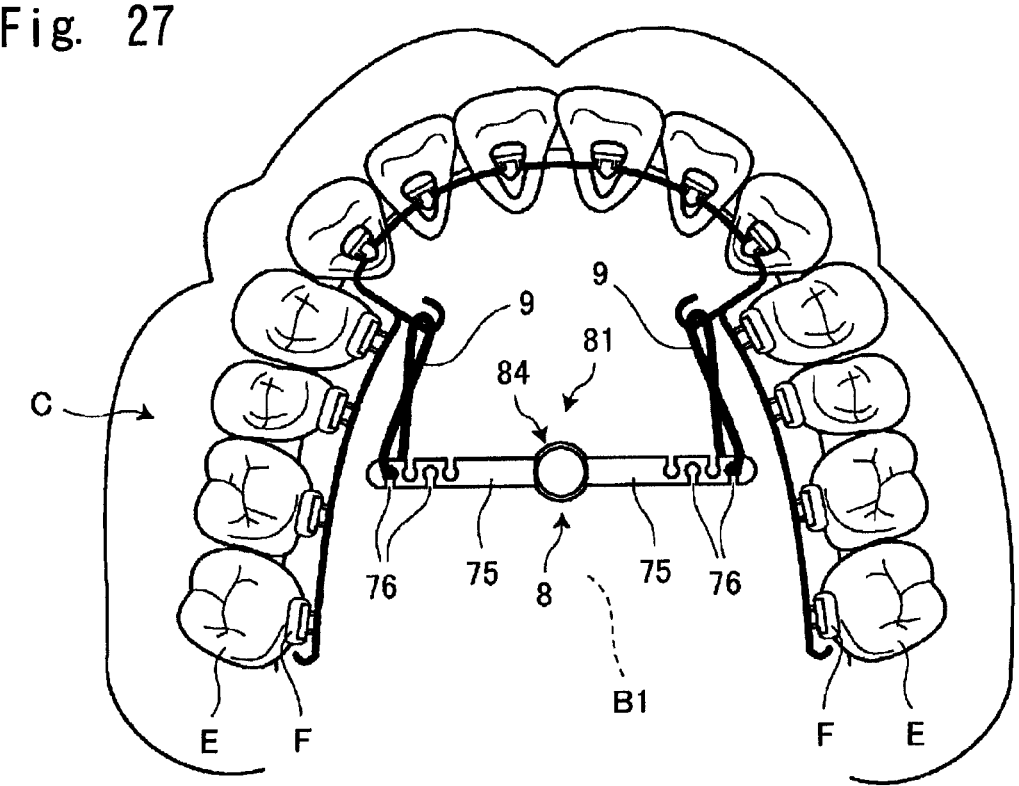
FIG. 27 is an explanatory view showing a using state of the modification 2 of the dental implant structure for an orthodontic.

The modification 2 of the dental implant structure for orthodontic is explained in conjunction with FIG. 26 and FIG. 27.

As shown in FIG. 26, the dental implant structure 71 for orthodontic is configured such that a support anchor 8 is embedded in an upper jaw bone B1, and an artificial tooth base 74 for orthodontic having two arm portions 75, 75 is placed on and fixed to an upper portion of the support anchor 8.

The artificial tooth base 74 for orthodontic has a frusto-conical shape, and the arm portions 75, 75 with which a dental wire 9 is engaged are arranged on an outer peripheral portion 74a in the lateral direction. That is, a plurality of concave engaging portions 76, 76, 76, 76 are formed on both side portions of each arm portion 75 in the longitudinal direction.

As shown in FIG. 27, a bracket F is adhered to each tooth E on an upper jaw side, while a support anchor 8 is embedded in a center portion of the upper jaw bone, and an artificial tooth base 74 for orthodontic is placed on an upper portion of the support anchor 8. The dental wire 9 is mounted on the engaging portions 76, 76 of the left and right arm portions 75, 75 of the artificial tooth base 74 and the respective brackets F, . . . , F. Accordingly, each tooth E is pulled toward the dental implant structure 71 for orthodontic by way of the dental wire 9 and hence, an orthodontic operation of the teeth arrangement on the upper jaw can be performed.

The plurality of engaging portions 76, . . . , 76 are formed in the left and right arm portions 75, 75 from a distal end side to a proximal end side. However, for example, when only the engaging portion 76 on the proximal end side of the arm portion 75 is used, the dental implant structure 71 for orthodontic may be used by cutting away the arm portion 75 at a position in the vicinity of the third engaging portion 76 counted from the distal end side of the arm portion 75.

[Modification 3 of Dental Implant Structure for Orthodontic]

Figure 28:
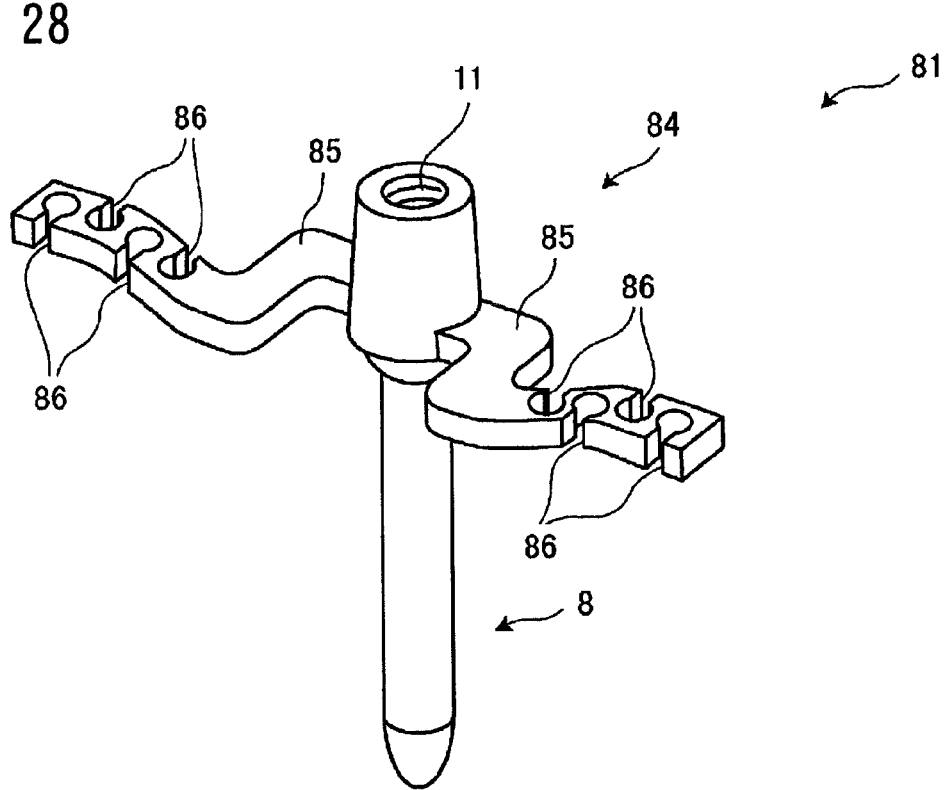
FIG. 28 is an exploded perspective view showing a modification 3 of the dental implant structure for an orthodontic.
Figure 29:
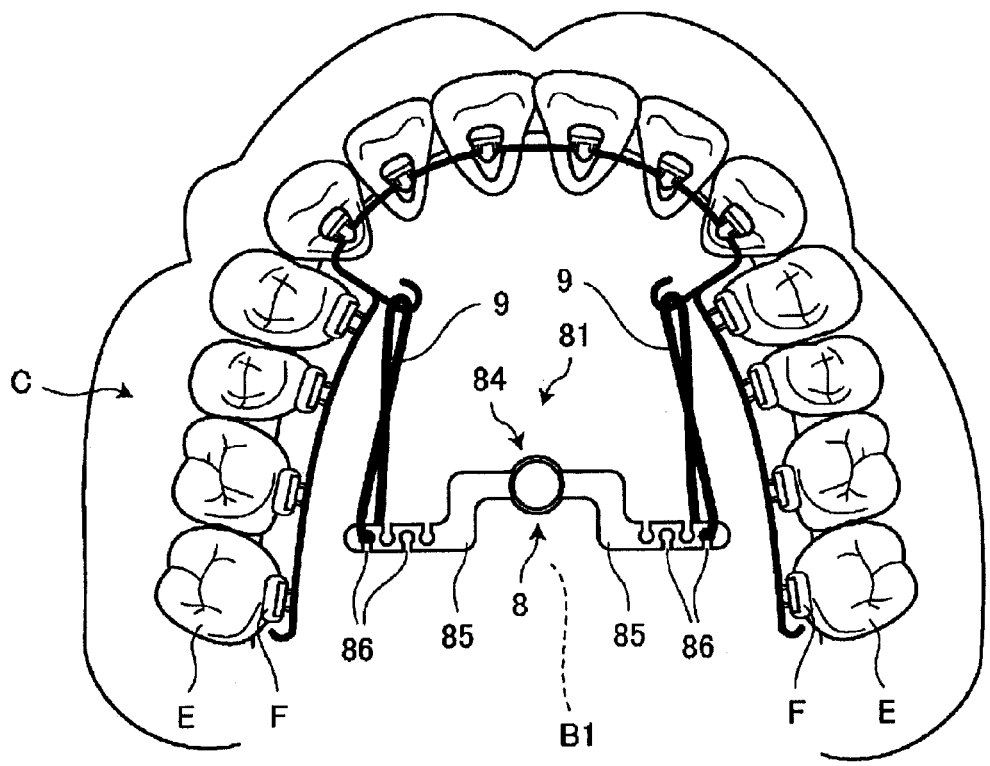
FIG. 29 is an explanatory view showing a using state of the modification 3 of the dental implant structure for an orthodontic.

The modification 3 of the dental implant structure for orthodontic is explained in conjunction with FIG. 28 and FIG. 29.

As shown in FIG. 28, dental implant structure 81 for orthodontic is configured such that a support anchor 8 is embedded in an upper jaw bone B1, and an artificial tooth base 84 for orthodontic having two arm portions 85, 85 is placed on and fixed to an upper portion of the support anchor 8.

The artificial tooth base 84 for orthodontic has a frusto-conical shape, and the arm portions 85, 85 with which a dental wire 9 is engaged are arranged on an outer peripheral portion 84a in the lateral direction. That is, one arm portion 85 (the right arm portion 85) is formed in an approximately Z-shape as viewed in a plan view, and the other arm portion 85 (the left arm portion 85) is formed in an approximately reverse Z-shape as viewed in a plan view). A plurality of concave engaging portions 86, 86, 86, 86 are formed on both side portions of each arm portion 85 in the longitudinal direction.

As shown in FIG. 29, a bracket F is adhered to each tooth E on an upper jaw side, while the support anchor 8 is embedded in a center portion of the upper jaw, and the artificial tooth base 84 for orthodontic is placed on an upper portion of the support anchor 8. The dental wire 9 is mounted on the engaging portions 86, 86 of the left and right arm portions 85, 55 of the artificial tooth base 84 and the respective brackets F, F. Accordingly, each tooth E is pulled toward the dental implant structure for orthodontic by way of the dental wire 9 and hence, an orthodontic operation of the teeth arrangement on the upper jaw can be performed. By forming the left and right arm portions 85, 85 into the above-mentioned shape, it is possible to position the respective engaging portions 86, 86 on a pharynx portion side by the dental implant structure 81 for orthodontic shown in FIG. 28.

The plurality of engaging portions 86, . . . , 86 are formed in the left and right arm portions 85, 85 from a distal end side to a proximal end side. However, for example, when only the engaging portion 86 on the proximal end side of the arm portion 85 is used, the dental implant structure 81 for orthodontic may be used by cutting away the arm portion 85 at a position in the vicinity of the third engaging portion 86 counted from the distal end side of the arm 85.

II [Method of Assembling Dental Implant Structure]

As shown in FIG. 30 to FIG. 43, the method of assembling dental implant structure is constituted of the following respective steps i) to xiii).

In this embodiment, a mode in which one tooth is lost and an implant is applied to a jaw bone B is firstly explained. Then, the bridge implant structure and the method of assembling the bridge implant structure are explained. Thereafter, the method of disassembling both implant structures is explained.

Figure 30:
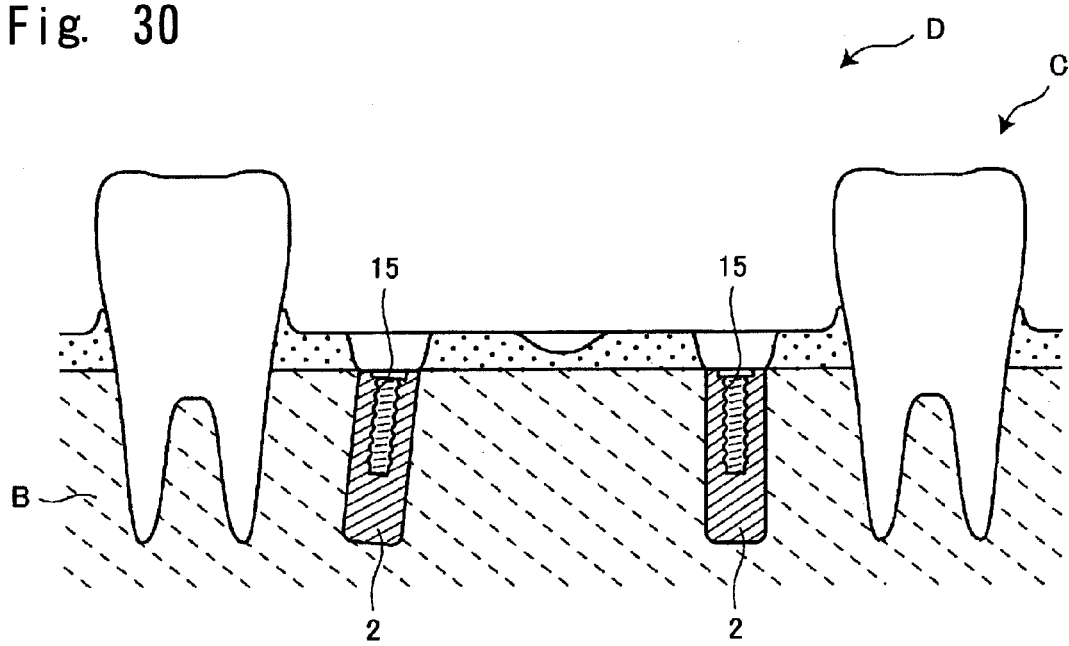
FIG. 30 is a step view showing an assembling method of the dental implant structure of the embodiment.

That is, in step i) which is a fixture mounting step, as shown in FIG. 30, the fixtures 2 for placing and fixing the abutment 3 onto the upper portions thereof are embedded in the jaw bone B.

Figure 31:
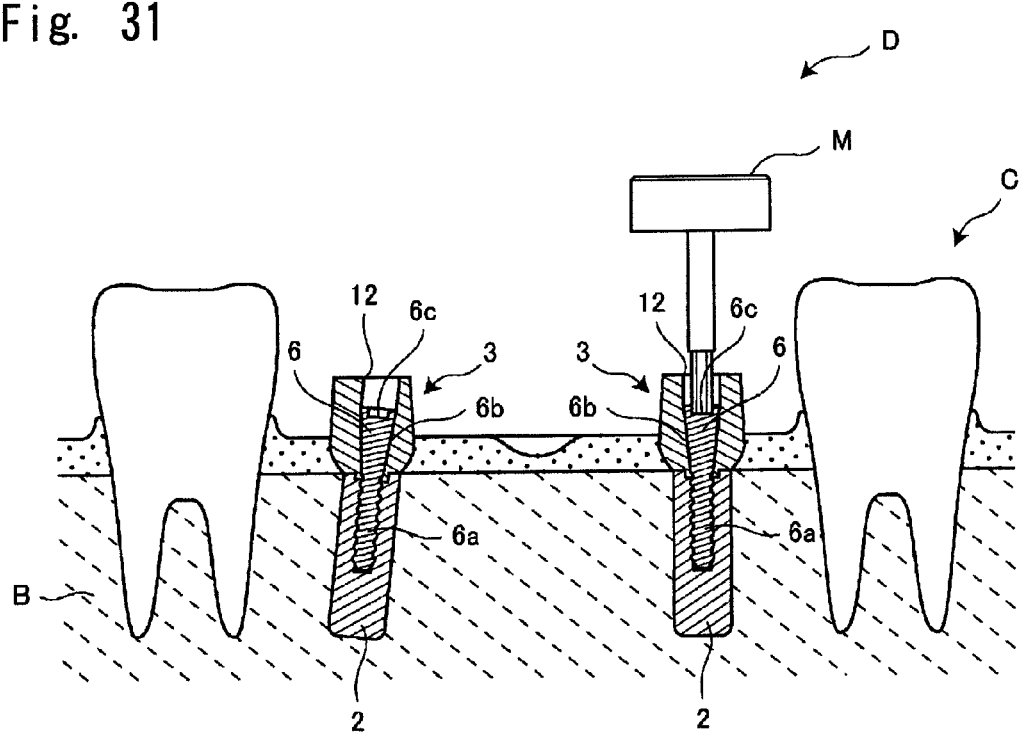
FIG. 31 is a step view showing the assembling method of the dental implant structure of the embodiment.

As shown in FIG. 31, in step ii) which is an abutment connecting step, the abutment 3 which is configured to place and fix the artificial tooth 5 onto the upper portion thereof is placed on the upper portion of the fixture 2. Thereafter, the male screw rod 6 is inserted into the female threaded hole 15 and the male screw penetration hole 12 which are formed in the abutment 3 and the fixture 2 respectively in a corresponding manner. The male screw rod 6 is threadedly engaged with the female threaded hole 15 formed in the fixture 2 using a male screw fastening jig M which is prepared separately thus connecting the abutment 3 to the fixture 2 to each other.

In such a state, the male threaded portion 6a which constitutes a lower portion of the male screw rod 6 is threadedly engaged with the fixture 2, and the tapered portion 6b which constitutes an upper portion of the male screw rod 6 is engaged with the upwardly expanding male screw penetration hole 12 formed in the abutment 3 in taper fitting. Accordingly, it is possible to prevent the removal of the abutment 3 in the upward direction due to such taper fitting.

Figure 32:
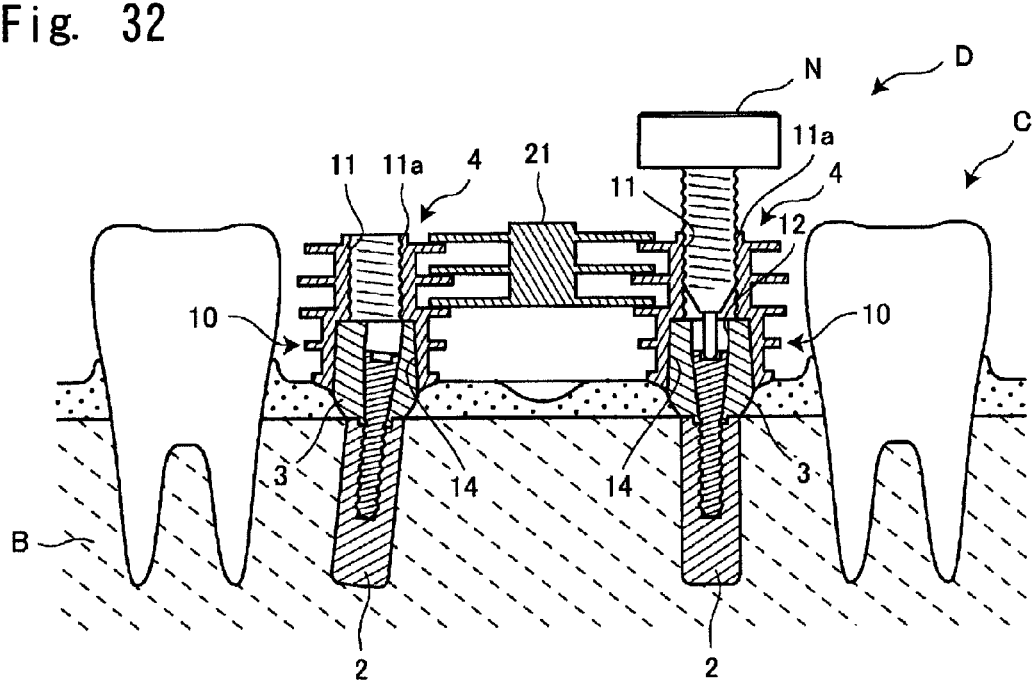
FIG. 32 is a step view showing the assembling method of the dental implant structure of the embodiment.

In step iii) which is an artificial tooth base fitting step, as shown in FIG. 32, the artificial tooth base 4 is detachably placed on the upper portion of the abutment 3 by way of the taper fitting structure 10, an artificial tooth base fastening screw jig N which is prepared separately is threadedly engaged with the female threaded hole 11 and is threadedly advanced until a distal end of the screw jig N is brought into contact with an upper end surface 6c of the male screw rod 6 disposed below the screw jig N so that the artificial tooth base 4 is fitted onto a peripheral surface of the abutment 3 in a close contact manner by way of the fitting hole 14 formed in the artificial tooth base 4.

Figure 33:
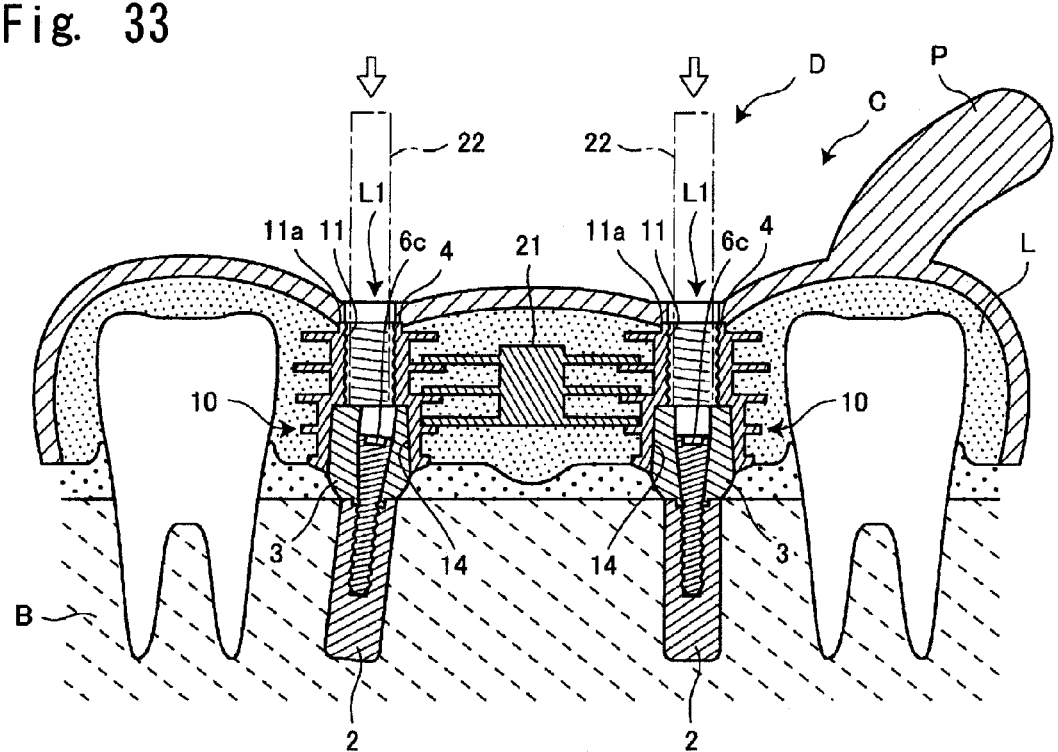
FIG. 33 is a step view showing the assembling method of the dental implant structure of the embodiment.

In step iv) which is a molding covering step, as shown in FIG. 33, a teeth arrangement portion C including the artificial tooth base 4 is covered with a molding resin L for taking a mold for the teeth arrangement portion C including the artificial tooth base 4. Here, before covering the teeth arrangement portion C with the molding resin L, an elongated screw rod 22 is threadedly engaged with the female threaded hole 11 formed in the artificial tooth base 4, and the screw rod 22 is removed from the artificial tooth base 4 after the molding covering step is finished.

In the drawing, symbol P indicates a molding container for holding the molding resin L.

Figure 34:
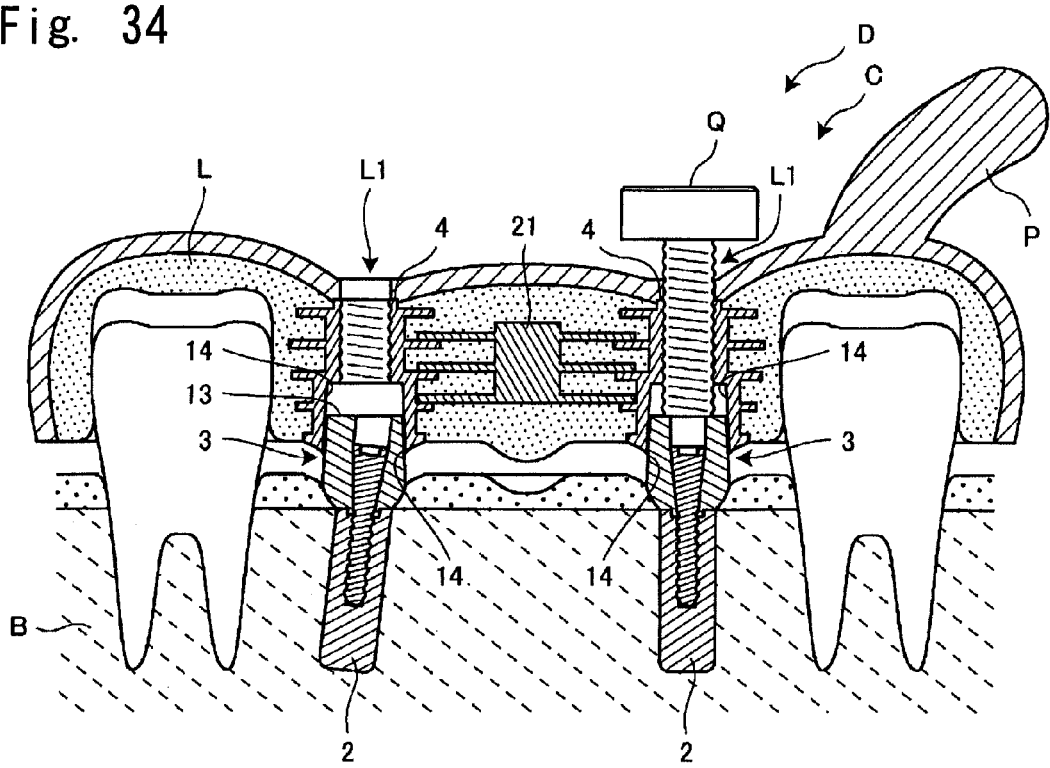
FIG. 34 is a step view showing the assembling method of the dental implant structure of the embodiment.

In step v) which is an artificial tooth base separation step, as shown in FIG. 34, a separation male screw jig Q which is prepared separately is threadedly engaged with the female threaded hole formed in the artificial tooth base 4 from above the molding resin L through a start end of the female threaded hole so as to bring a distal end surface of the separation male screw jig Q into pressure contact with the stepped portion 13 of the abutment 3, and due to the further rotation of the separation male screw jig Q, the abutment 3 and the artificial tooth base 4 are separated from each other by making use of a pressure contact reaction force which is generated when the distal end surface is brought into contact with the stepped portion of the abutment 3, and the abutment 3 remains in the inside of the oral cavity D.

An opening hole L1 is formed in the molding resin L so as to expose the opening end 11a of the female threaded hole 11 formed in the artificial teeth base 4.

Figure 35:
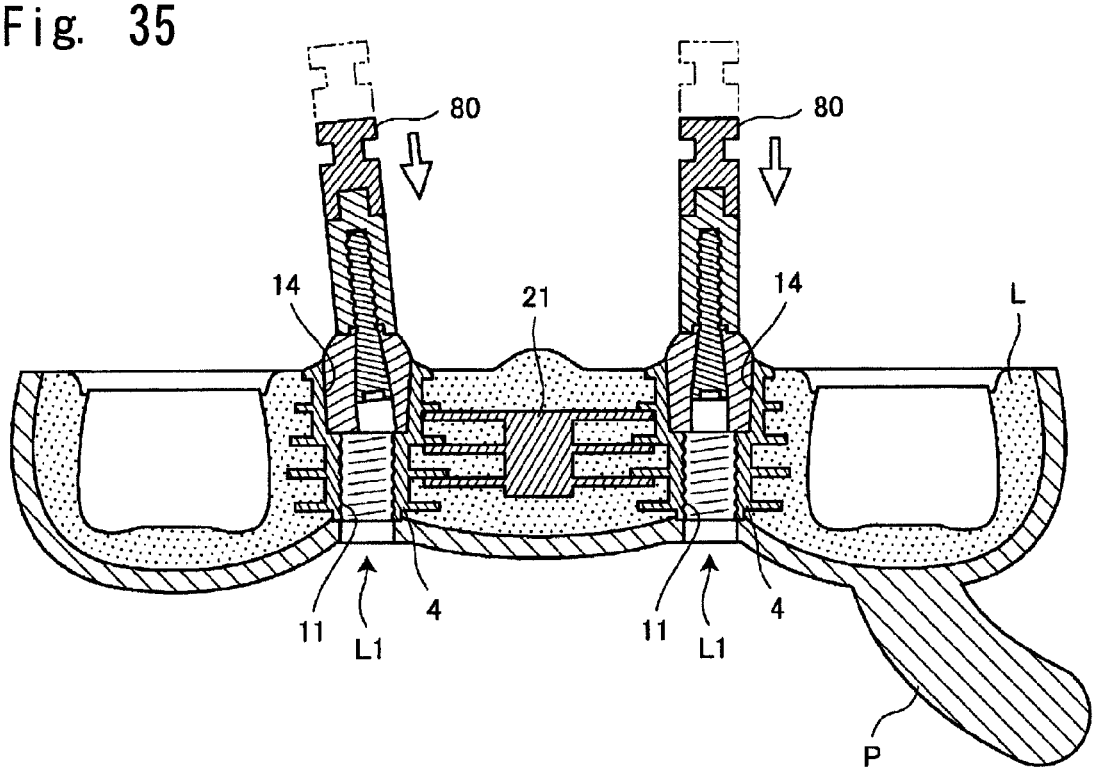
FIG. 35 is a step view showing the assembling method of the dental implant structure of the embodiment.

In step vi) which is an anchor temporarily holding step, as shown in FIG. 35, the molding resin L which includes the artificial tooth base 4 separated from the abutment 3 is taken out from the inside of the oral cavity D and is reversed. Into a tapered fitting hole 14 which is formed in the artificial tooth base 4 and is opened on a surface of the molding resin L, a dummy temporarily holding anchor 80 having a shape corresponding to the fitting hole 14 is fitted. A distal end of the dummy temporarily holding anchor 80 has a shape corresponding to a shape of the tapered fitting hole 14 formed in the artificial tooth base 4, that is, the same shape as the taper fitting structure 10 of the abutment 3 remaining in the inside of the oral cavity D of the patient. Here, the dummy temporarily holding anchor 80 has the structure where a dummy fixture and a dummy abutment are connected to each other by way of a dummy male screw rod. However, the dummy temporarily holding anchor 80 is not limited to such structure, and may have the structure where the dummy fixture and the dummy abutment are formed by integral molding.

Figure 36:
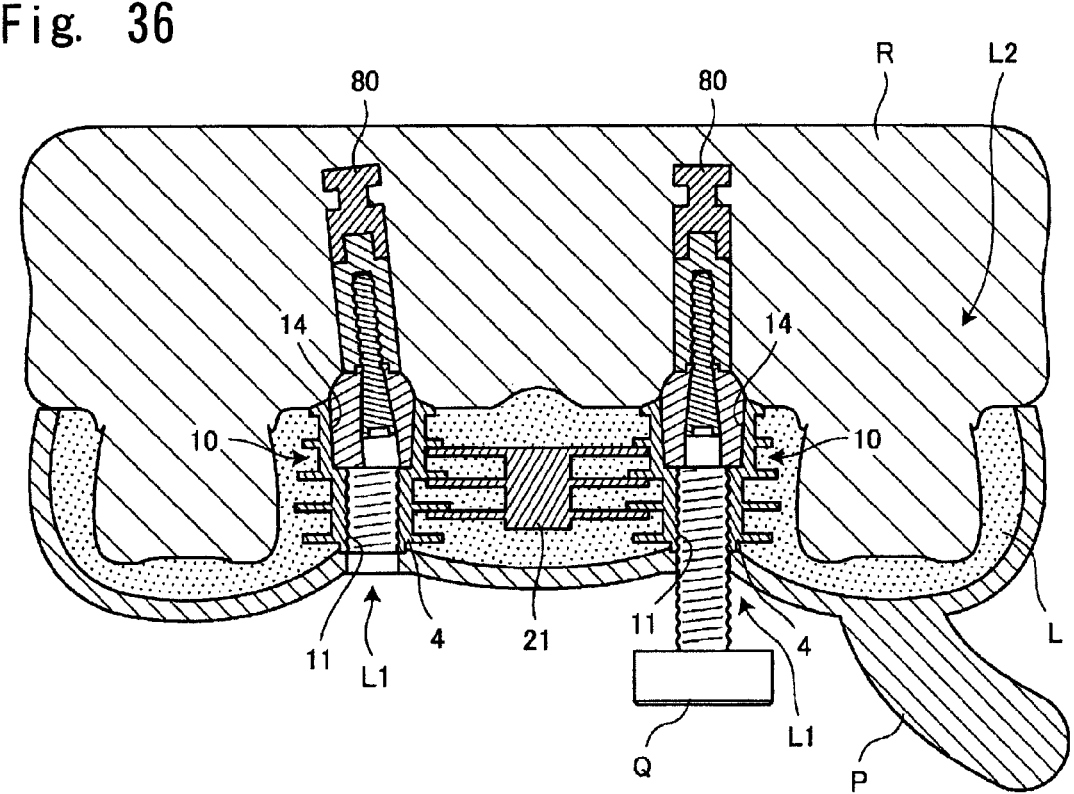
FIG. 36 is a step view showing the assembling method of the dental implant structure of the embodiment.

In step vii) which is a molding material in-flow step, as shown in FIG. 36, a molding material R such as plaster is made to flow into a recessed portion L2 formed on a surface of the molding resin L so as to embed the dummy temporarily holding anchor 80 by way of the taper fitting structure 10 in a state where the dummy temporarily holding anchor 80 is fitted and mounted upright in the tapered fitting hole 14 formed in the artificial tooth base 4.

In making the molding material R flow into the recessed portion L2, it is possible to take not only a mold of implanted portions but also a mold of the teeth and other peripheral portions.

Figure 37:
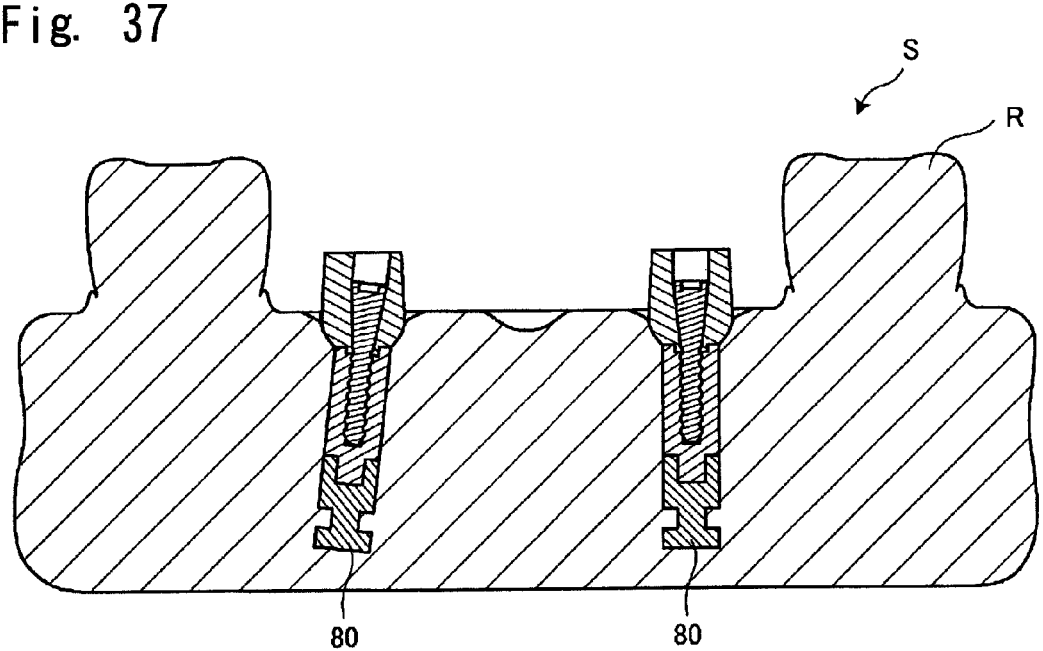
FIG. 37 is a step view showing the assembling method of the dental implant structure of the embodiment.

In step viii) which is a model preparation step, as shown in FIG. 37, after the molding material R is hardened, the molding material which is hardened is removed together with the temporarily holding anchor 80 from the surface recessed portion of the molding resin L while leaving the artificial tooth base 4 in the inside of the molding resin L thus completing a teeth arrangement model S made of the molding material such as plaster in the oral cavity D. Although the model is prepared using an artificial tooth base which is newly produced by casting on the abutment conventionally, according to this embodiment, the model can be prepared by using the existing artificial tooth base 4 and hence, it is possible to form the teeth arrangement model S with more precision and with substantially no allowance.

In removing the artificial tooth base 4 which is left in the inside of the molding resin L from the temporarily holding anchor 80, it is possible to remove the artificial tooth base 4 by making use of a maximum reaction force with the use of the separation male screw jig Q prepared separately (see FIG. 16).

Figure 38:
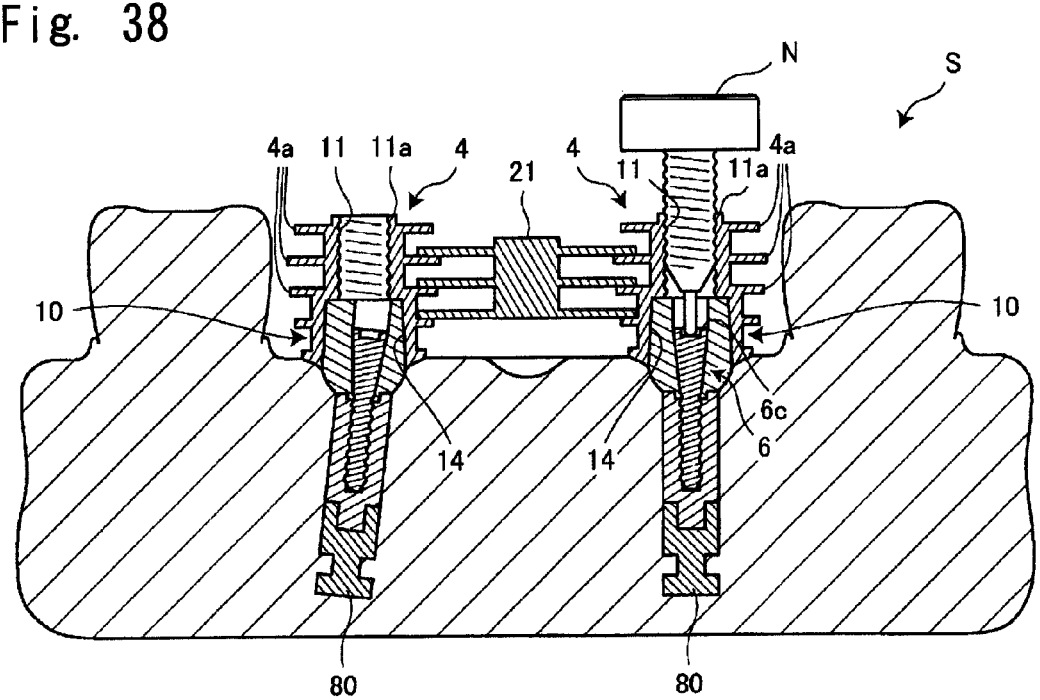
FIG. 38 is a step view showing the assembling method of the dental implant structure of the embodiment.

In step ix) which is an artificial tooth base fitting step for fitting and placing the artificial tooth base 4 onto the anchor 80, as shown in FIG. 38, a separately prepared artificial tooth base 4 is fitted and placed onto a tapered head of the temporarily holding anchor 80 which is exposed at an implant corresponding portion of the teeth arrangement model by way of the taper fitting structure 10.

In fitting the separately prepared artificial tooth base 4 onto the dummy temporarily holding anchor 80, a separately prepared artificial tooth base fastening screw jig N may be used.

Figure 39:
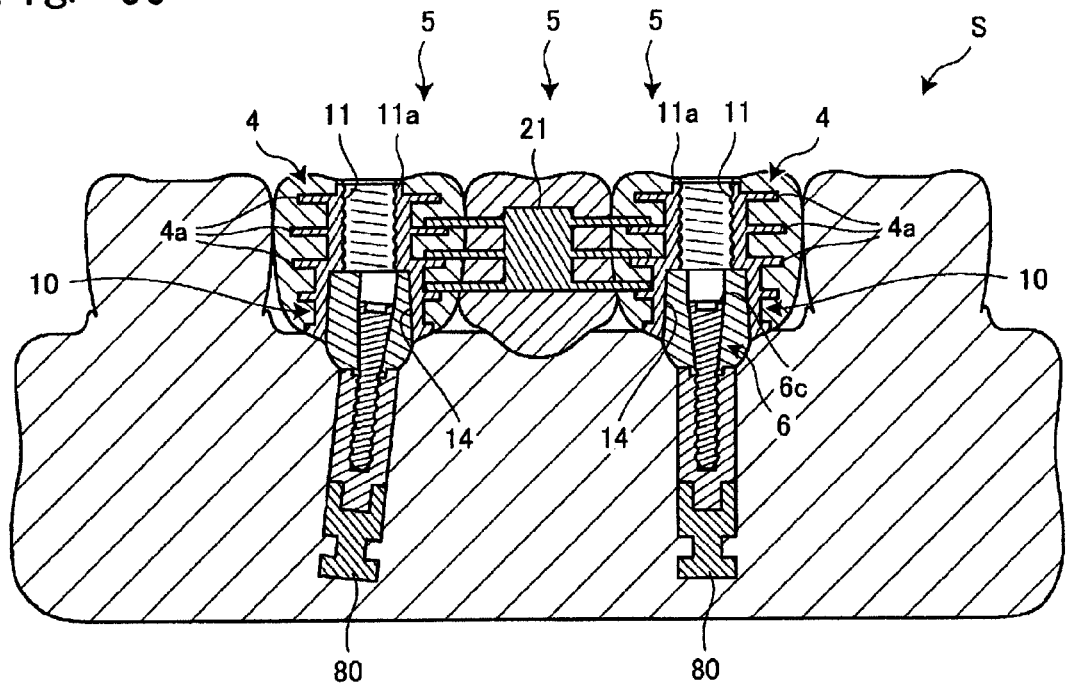
FIG. 39 is a step view showing the assembling method of the dental implant structure of the embodiment.

In step x) which is a tooth capping step, as shown in FIG. 39, an artificial tooth 5 is capped over the artificial tooth base 4 while adjusting the balance between the artificial tooth base and the tooth and the teeth arranging model S around the artificial tooth base 4.

Figure 40:
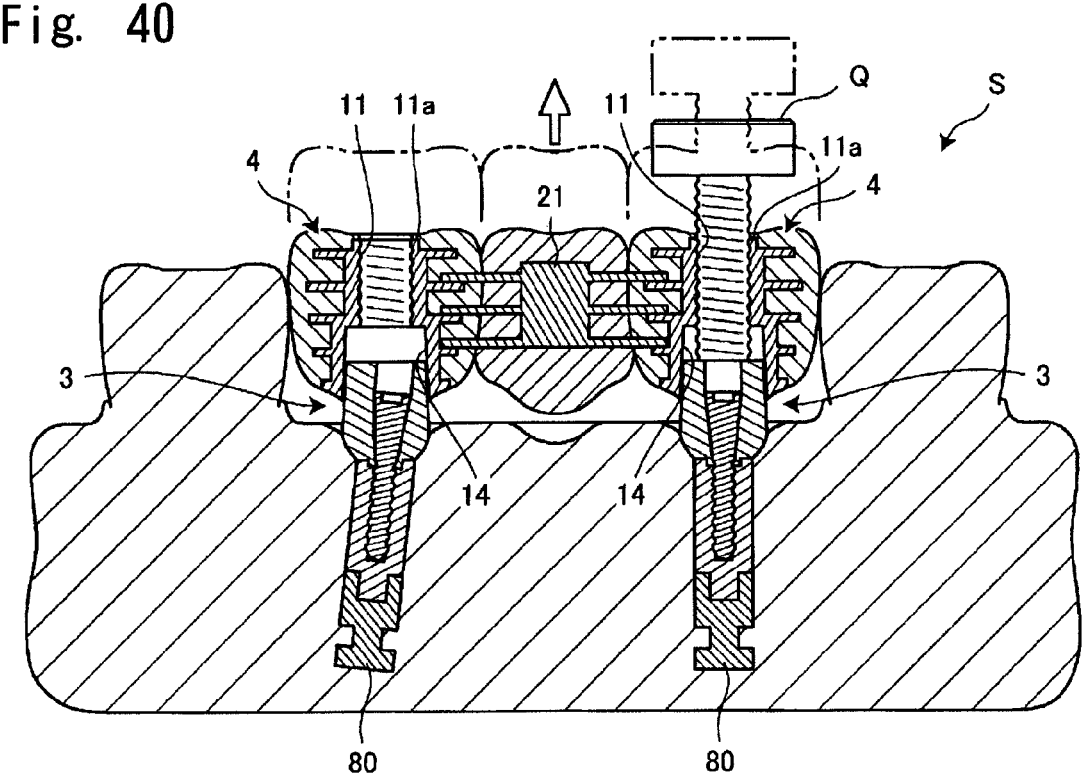
FIG. 40 is a step view showing the assembling method of the dental implant structure of the embodiment.

In step xi) which is an artificial tooth base takeout step, as shown in FIG. 40, a separation male screw jig Q which is prepared separately is threadedly engaged with the female threaded hole 11 formed in the artificial tooth base 4 through a start end of the female threaded hole 11 thus bringing a distal end surface of the separation male screw jig Q into pressure contact with the upper end surface of the temporarily holding anchor 80 thus separating and taking out the artificial tooth base 4 from the temporarily holding anchor 80 by making use of a pressure contact reaction force.

Figure 41:
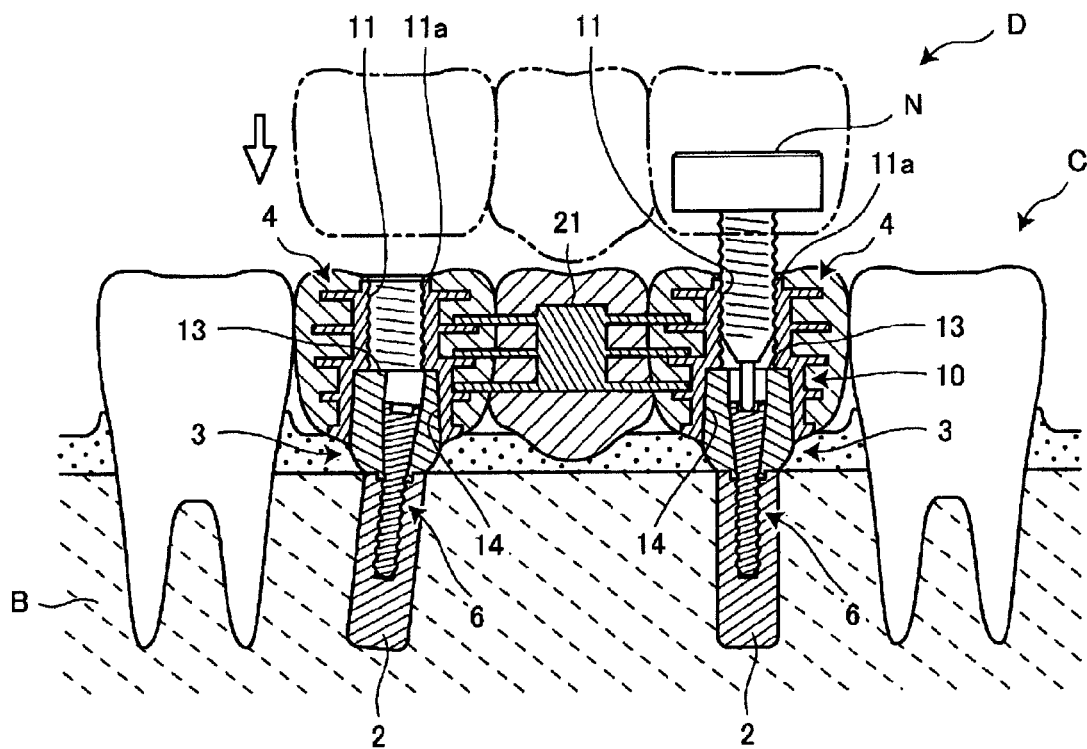
FIG. 41 is a step view showing the assembling method of the dental implant structure of the embodiment.

In step xii) which is a final artificial tooth base fitting step, as shown in FIG. 41, the removed artificial tooth base 4 is fitted onto the abutment 3 which is installed in the inside of the oral cavity D of a patient by way of the taper fitting structure 10. Next, an artificial tooth base fastening screw jig N which is prepared separately is threadedly engaged with the female threaded hole 11 and is threadedly advanced while bringing a distal end thereof into contact with an upper end surface 6c of the male screw rod 6 so that the peripheral surface of the abutment 3 is fitted into the fitting hole 14 formed in the artificial tooth base 4 in a close contact manner.

Figure 42:
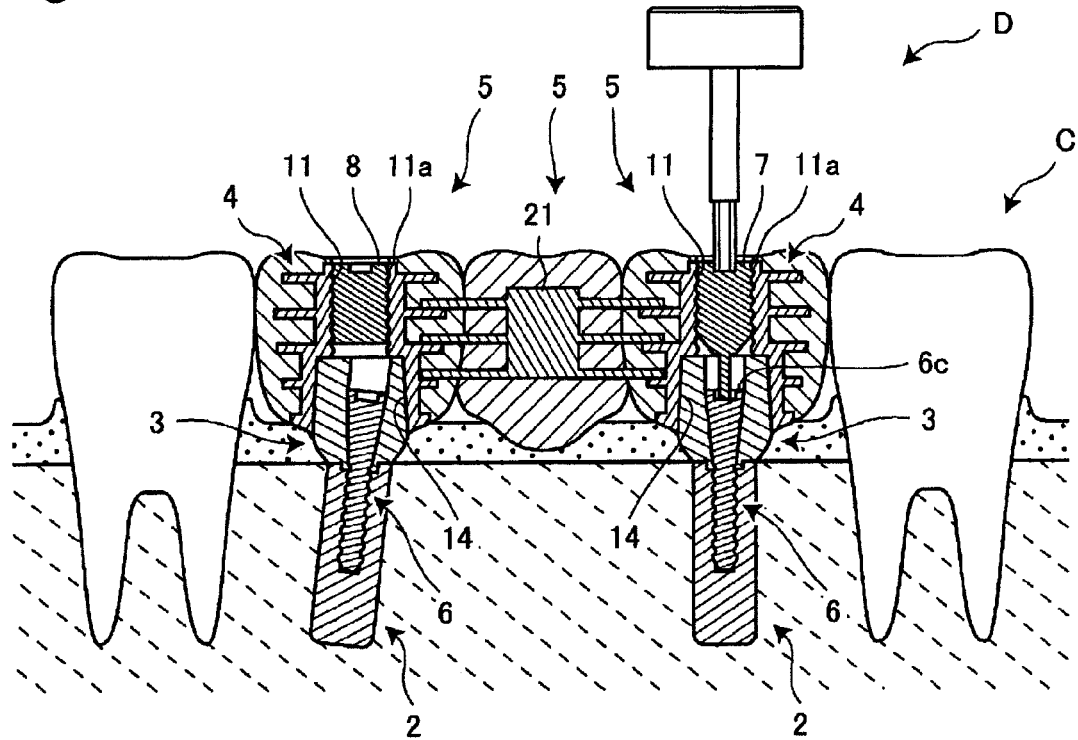
FIG. 42 is a step view showing the assembling method of the dental implant structure of the embodiment.

In step xiii) which is a female threaded hole closing step, as shown in FIG. 42, a closing screw 7 which has a lower end thereof formed into a tapered shape is threadedly engaged with the female threaded hole 11 formed in a center portion of the artificial tooth base 4 so as to close the female threaded hole 11, and a distal end of the closing screw 7 is brought into contact with the upper end surface 6c of the male screw rod 6. Although the closing screw 7 is used for closing the female threaded hole 11, a dental cement may be used for closing the female threaded hole 11.

Figure 43:
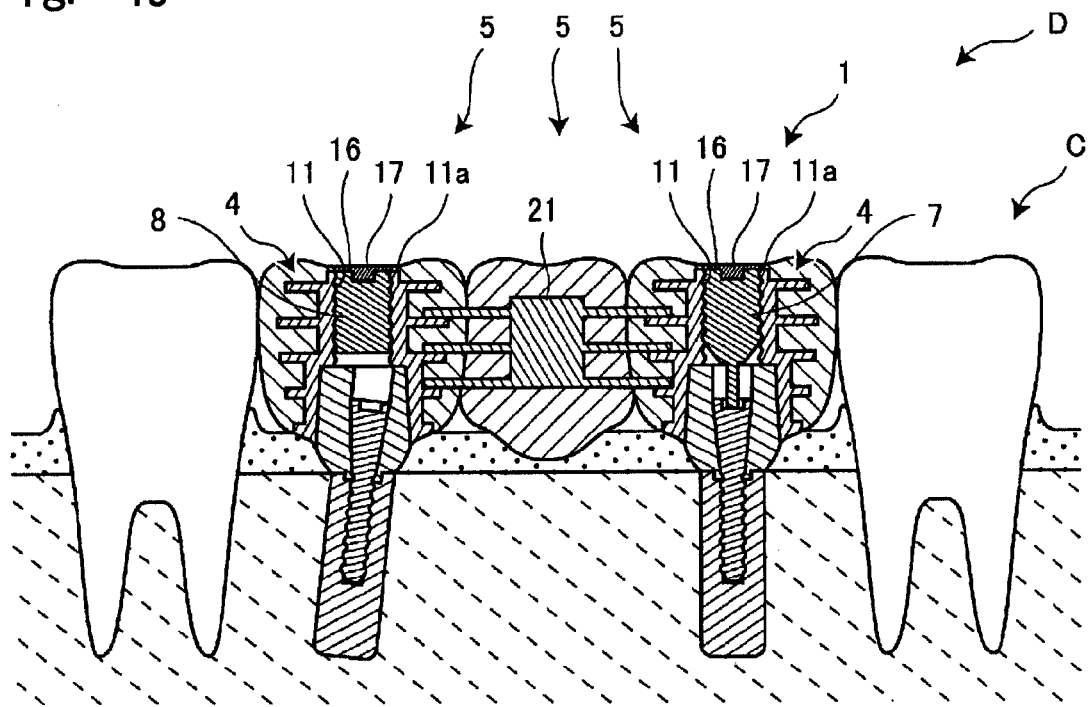
FIG. 43 is a step view showing the assembling method of the dental implant structure of the embodiment.

As shown in FIG. 43, after the step xiii) is finished, a work hole 16 corresponding to the female threaded hole 11 formed in the upper end surface of the artificial tooth 5 is closed by a plug 17.

In this manner, by threadedly engaging the closing screw 7 having the lower end thereof formed into a tapered shape with the female threaded hole 11 formed in a center portion of the artificial tooth base 4 and by bringing the distal end of the closing screw 7 into contact with the upper end surface 6c of the male screw rod 6, slackening of the male screw rod 6 can be prevented thus preventing the formation of a gap caused by the separation of the abutment 3 from the fixture 2.

Conventionally, the artificial tooth base produced by casting is used to prepare the mold. According to this embodiment, an existing artificial tooth base can be used as such an artificial tooth base and hence, the dental implant structure can be made light-weighted. Further, since a casting step is no more necessary, it is unnecessary for a patient to be afraid of allergy caused by material dissolved from a cast product.

In a conventional method, when the fixture 2 is embedded in the jaw bone B, a dedicated cuff is mounted on an upper portion of the fixture 2 as a lid during a period until a gingiva A is cured. However, the abutment 3 used in this embodiment can be also used as a dedicated cuff in a state where the abutment 3 is mounted on the fixture 2.

Further, in mounting the artificial tooth base 4 on the abutment 3, the above-mentioned step xii) includes the final artificial tooth base fitting step where the tooth base fastening screw jig N is threadedly engaged with the female threaded hole 11, and the distal end of the screw jig N is threadedly advanced while keeping contact with the upper end surface 6c of the male screw rod 6 disposed below the screw jig N so that the peripheral surface of the abutment 3 is fitted into the fitting hole 14 formed in the artificial tooth base 4 in a close contact manner. However, in the final artificial tooth base fitting step, it is not always necessary to fit the peripheral surface of the abutment 3 into the fitting hole 14 formed in the artificial tooth base 4 by threadedly engaging the artificial tooth base fastening screw jig N with the female threaded hole 11. That is, the peripheral surface of the abutment 3 may be fitted into the fitting hole 14 formed in the artificial tooth base 4 in a close contact manner by simply making use of taper fitting.

III [Bridging Implant Structure and Method of Assembling Bridging Implant Structure]

The above-mentioned method of assembling the dental implant structure is an implant assembling method applicable to the case where a single tooth per se is lost. However, there may be a case where it is necessary to assemble the implant structure on a plurality of artificial teeth and to bridge these implant structures or a case where it is necessary to connect a plurality of artificial teeth.

Further, in forming the other implant assembling structure, the fixture 2 is embedded in the jaw bone in an inclined state corresponding to conditions on the jaw bone and the teeth arrangement, the abutment 3 is placed on the fixture 2 perpendicularly, and the abutment 3 maintains the parallelism with the other abutment 3, and the artificial tooth bases 4 are bridged for crowning the artificial teeth 20 as shown in FIG. 32.

Hereinafter, the explanation is made with respect to a case where the implant assembling structure is assembled at two places, and the artificial teeth are bridged between two implant assembling structures.

Firstly, the implant structure at one implant position is assembled by the method already explained heretofore.

Next, the new implant structure is assembled at the other implant position disposed adjacent to the tooth to be bridged between two implant assembling structures.

That is, as shown in FIG. 30, the fixture 2 is embedded in the jaw bone B in an inclined state, and the abutment 3 is placed on and fixed to an upper portion of the fixture 2 in a slightly inclined state. Then, the artificial tooth base 4 is placed on and fixed to an upper portion of the abutment 3, and the artificial tooth 5 is mounted on the artificial tooth base 4.

The abutment 3 and the artificial tooth base 4 are configured to be detachably fitted to each other in a close contact manner by way of the taper fitting structure 10. Further, a female threaded hole 11 which is vertically formed in the artificial tooth base 4 has a larger diameter than a male screw penetration hole 12 which is vertically formed in the abutment 3 thus forming a stepped portion 13 constituted of an upper end surface of the abutment 3 on a boundary between the female threaded hole 11 and the male screw penetration hole 12 which are communicated with each other.

Here, to allow the artificial tooth base 4 which is fitted on the abutment 3 to maintain parallelism with the neighboring artificial tooth base 4 which is already assembled, (that is, to prevent the abutment 3 from taking an undercut state where the abutment 3 cannot maintain the parallelism so that bridging of the bridging artificial tooth base 21 (see FIG. 32) described later cannot be performed), the degree of parallelism is adjusted by rotating the inclined abutment 3 about an imaginary axis thereof while measuring the parallelism using a paralleling jig T which is prepared separately (see FIG. 45).

In this manner, the above-mentioned steps i), ii), iii) are carried out (see FIG. 30 to FIG. 32).

In such a state, two artificial tooth bases 4, 4 (one and the other artificial tooth bases 4, 4) stand upright and parallel to each other. Next, for connecting two artificial tooth bases 4, 4, the bridging artificial tooth base 21 is interposed and connected between these artificial tooth bases 4, 4 by making use of engagement projections 4a, . . . , 4a of the artificial tooth bases 4, 4.

In such a state, the above-mentioned step iv), that is, the molding covering step is carried out for covering two artificial tooth bases 4, 4 which stand upright, the bridging artificial tooth base 21 interposed between the artificial tooth bases 4, 4 and teeth arranged portion C with the molding resin L (see FIG. 33).

Next, to artificial tooth bases 4, 4 which stand upright and the bridging artificial tooth base 21 interposed between the artificial tooth bases 4, 4 are integrally separated from the respective abutments 3 by carrying out the above-mentioned step v). Two artificial tooth bases 4, 4 and the bridging artificial tooth base 21 interposed between the artificial tooth bases 4, 4 which are integrally formed with the molding resin L are taken out from the inside of the oral cavity D by carrying out the above-mentioned step vi), and the dummy temporarily holding anchors 80 are respectively temporarily mounted on two artificial tooth bases 4, 4 which are held integral with the molding resin L (see FIG. 34 and FIG. 35).

Next, the molding material R is made to flow over two artificial tooth bases 4, 4 which stand upright and the bridging artificial tooth base 21 interposed between the artificial tooth bases 4, 4 in an integral state by carrying out the above-mentioned step vii). Thereafter, the hardened molding material R is removed thus preparing the model made of the molding material R by carrying out the steps viii), ix). Further, two artificial tooth bases 4, 4 to which the bridging artificial tooth base 21 is engaged and connected are prepared separately, and these two artificial tooth bases 4, 4 are fitted on two dummy temporarily holding anchors 80, 80 which stand upright on the model (see FIG. 36 to FIG. 38).

Further, in the above-mentioned step x), three artificial teeth 5, 5, 5 are respectively mounted on the artificial tooth bases 4, 4 on the dummy temporarily holding anchors 80, 80 which stand upright and the bridging artificial tooth base 21 interposed between the artificial tooth bases 4, 4. Next, in the above-mentioned step xi), two artificial tooth bases 4, 4 on which the artificial teeth 5, 5, 5 are mounted are separated and removed from the temporarily holding anchors 80, 80 as an integral body. In the above-mentioned step xii), two artificial tooth bases 4, 4 on which the artificial teeth 5, 5, 5 and the bridging artificial tooth base 21 interposed between the artificial tooth bases 4, 4 are mounted are fitted on two abutments 3, 3 which are installed in the inside of the oral cavity D of the patient by way of the taper fitting structures 10, 10. Finally, in the above-mentioned step xiii), closing screws 7, 7 are respectively threadedly engaged with the female threaded holes 11, 11 formed in these two artificial tooth bases 4, 4 thus closing the female threaded holes 11, 11 (see FIG. 39 to FIG. 43).

IV [Method of Disassembling Implant Structure]

The method of removing the artificial tooth bases in the above-mentioned dental implant structure, that is, the method of disassembling the dental implant structure is carried out as follows.

In FIG. 1, the closing screw 7 which is threadedly engaged with the female threaded hole 11 vertically formed in the artificial tooth base 4 is threadedly disengaged from an upper-end opening portion of the female threaded hole 11 and is removed. Thereafter, by a method shown in FIG. 40, a separation male screw jig Q which is constituted of a male screw and is prepared separately is threadedly engaged with the female threaded hole 11 from which the closing screw 7 is removed until a lower end surface of the separation male screw jig Q is brought into contact with a stepped portion 13 positioned at a lowermost end of the female threaded hole 11. Thereafter, the separation male screw jig Q is further threadedly advanced so as to separate and remove the artificial tooth base 4 from the abutment 3 by making use of a reaction force of the artificial tooth base 4 against the abutment 3.

V [Jigs which are Prepared Separately]

The jigs which are prepared separately for use in the method of assembling the dental implant structure and the method of disassembling the implant structure described above are as follows.

Figure 46:
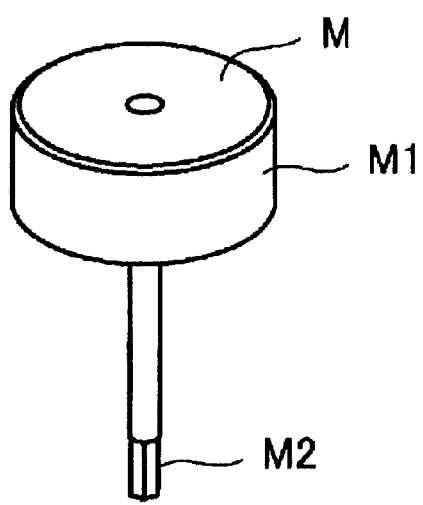
FIG. 46 is a perspective view showing the male screw fastening jig.

(1) The male screw fastening jig M used in step ii) is, as shown in FIG. 46, a driver having a disc-shaped handle portion M1 on an upper end thereof, and a lower end M2 of the male fastening jig M is configured to be engageable with a groove formed on the upper end surface 6*c* of the male screw rod 6. The male screw fastening jig M is used for connecting and fixing the abutment 3 to the fixture 2. The male screw rod 6 is made to pass through the male screw penetration hole 12 formed in the abutment 3, the male screw fastening jig M is made to pass through the male screw penetration hole 12 formed in the abutment 3, and is engaged with the upper end surface 6*c* of the male screw rod 6. Then, the male screw fastening jig M is rotated for fastening the male screw rod 6.

Figure 47:
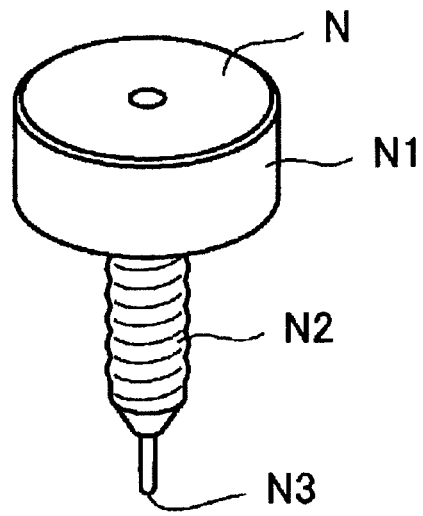
FIG. 47 is a perspective view showing an artificial tooth base fastening screw jig.

(2) The artificial tooth base fastening screw jig N used in steps iii), iv) is, as shown in FIG. 47, constituted of a disc-shaped handle portion N1 which forms an upper end of the jig N, a threaded portion N2 which extends downward from a center portion of the handle portion N1 and is threadedly engageable with the female threaded hole 11 formed in the artificial tooth base 4, and a flat portion N3 which extends downward forms a lower end of the threaded portion N2.

When the artificial tooth base fastening screw jig N is threadedly engaged with the female threaded hole 11 after fitting the artificial tooth base 4 on the abutment 3 by way of the taper fitting structure 10, the flat portion N3 which constitutes a lower end of the artificial tooth base fastening screw jig N is brought into contact with the stepped portion 13 which constitutes an upper end of the abutment 3. When the artificial tooth base fastening screw jig N is further rotated, the fastening is finished in a state where the artificial tooth base fastening screw jig N is threadedly advanced to a limit thus giving rise to a state where the artificial tooth base 4 is fitted on the abutment 3.

Figure 48:
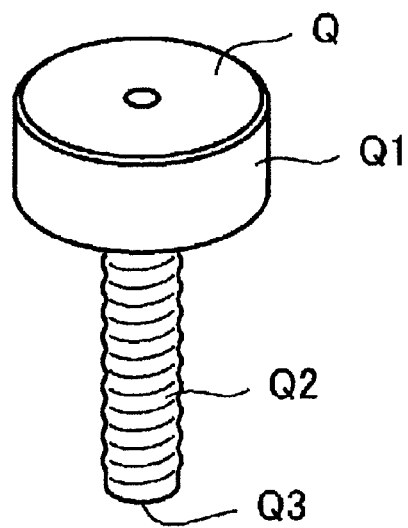
FIG. 48 is a perspective view showing a separation male screw jig.
Figure 49:
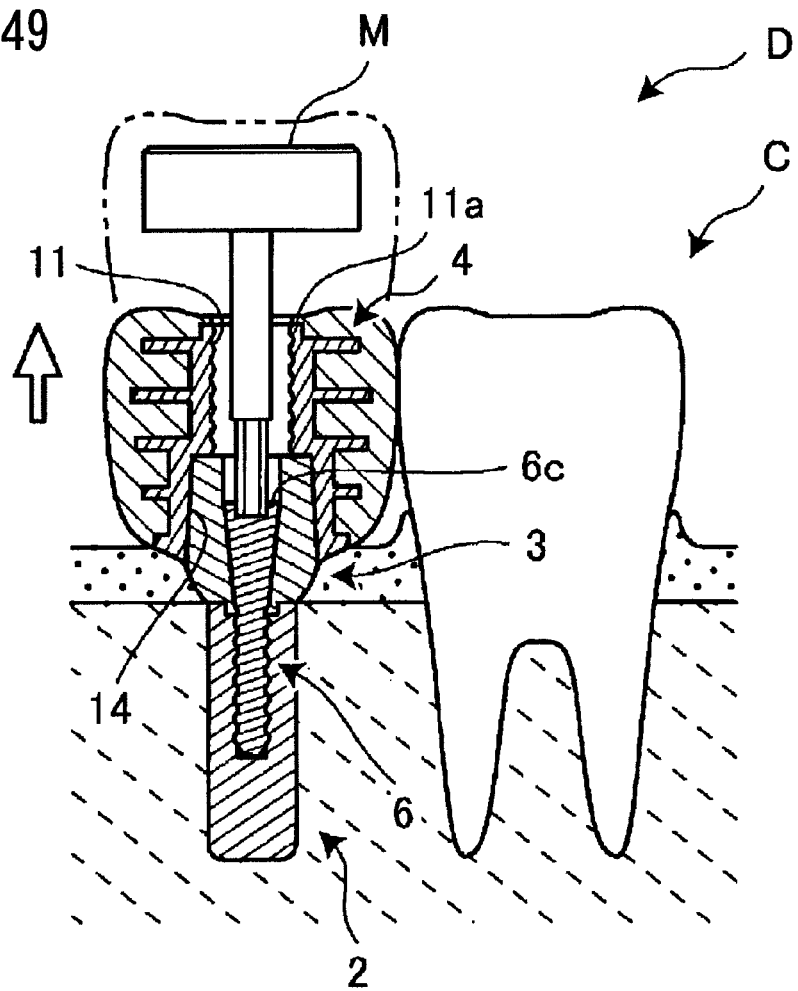
FIG. 49 is an explanatory view showing the steps of the manner of using an artificial tooth base removing jig.
Figure 50:
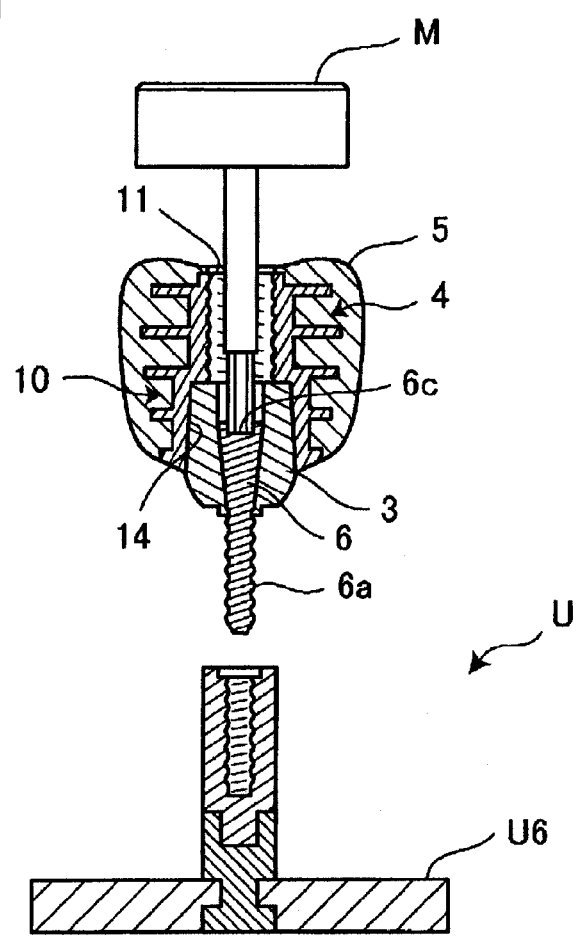
FIG. 50 is an explanatory view showing the steps of the manner of using the artificial tooth base removing jig.
Figure 51:
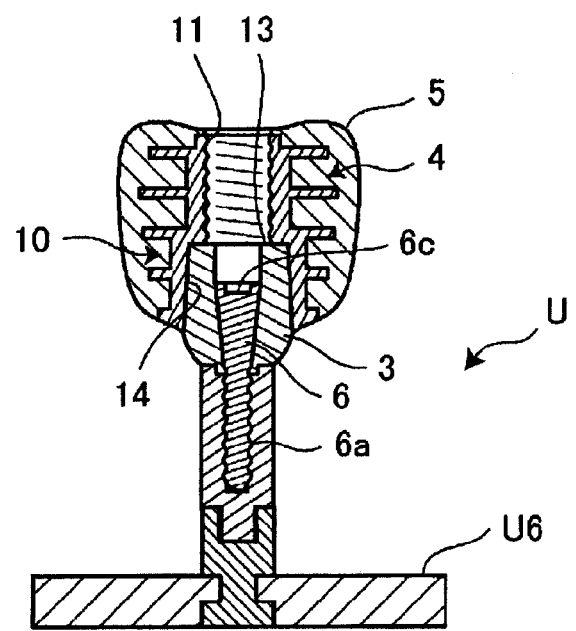
FIG. 51 is an explanatory view showing the steps of the manner of using the artificial tooth base removing jig.

(3) The separation male screw jig Q used in steps v), xi) is, as shown in FIG. 48, in the same manner as the artificial tooth base fastening screw jig N, constituted of a disc-shaped handle portion Q1 which forms an upper end of the jig Q and a threaded portion Q2 which extends downward from a center portion of the handle portion Q1 and is threadedly engageable with the female threaded hole 11 formed in the artificial tooth base 4, and a flat portion Q3 which extend downward forms a lower end of the threaded portion Q2.

In removing the artificial tooth base 4 from the abutment 3, the artificial tooth base fastening screw jig N is threadedly engaged with the female threaded hole 11 formed in the artificial tooth base 4 and, subsequently, when the artificial tooth base fastening screw jig N is further fastened in a state where the artificial tooth base fastening screw jig N is threadedly advanced to a limit, a reaction force is generated at a contact portion between the flat portion and the stepped portion 13 so that it is possible to release and remove the artificial tooth base 4 from the taper fitting structure 10.

(4) Paralleling Jig T

Figure 44:
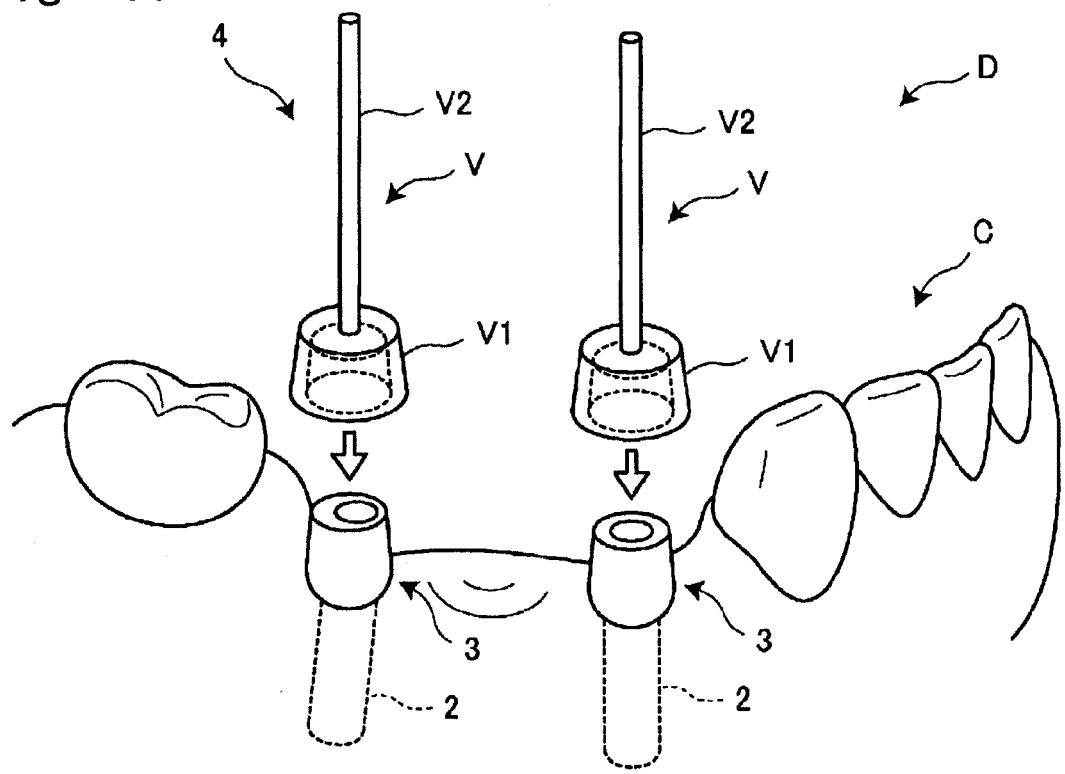
FIG. 44 is an explanatory view showing the steps of the manner of using a paralleling jig.

FIG. 44 shows the case where the implant structure is assembled at two positions and artificial teeth are assembled by bridging between two implant structures. In firstly assembling the implant structure at one implant position and, subsequently, newly assembling the implant structure at the other implant position adjacent to the tooth which constitutes the bridge, the fixture 2 is embedded in the jaw bone B in an inclined state, and the abutment 3 is placed on an upper portion of the fixture 2 also in an inclined state relative to the fixture 2, and artificial tooth base 4 is placed on and fixed to an upper portion of the abutment 3 perpendicularly.

Figure 45:
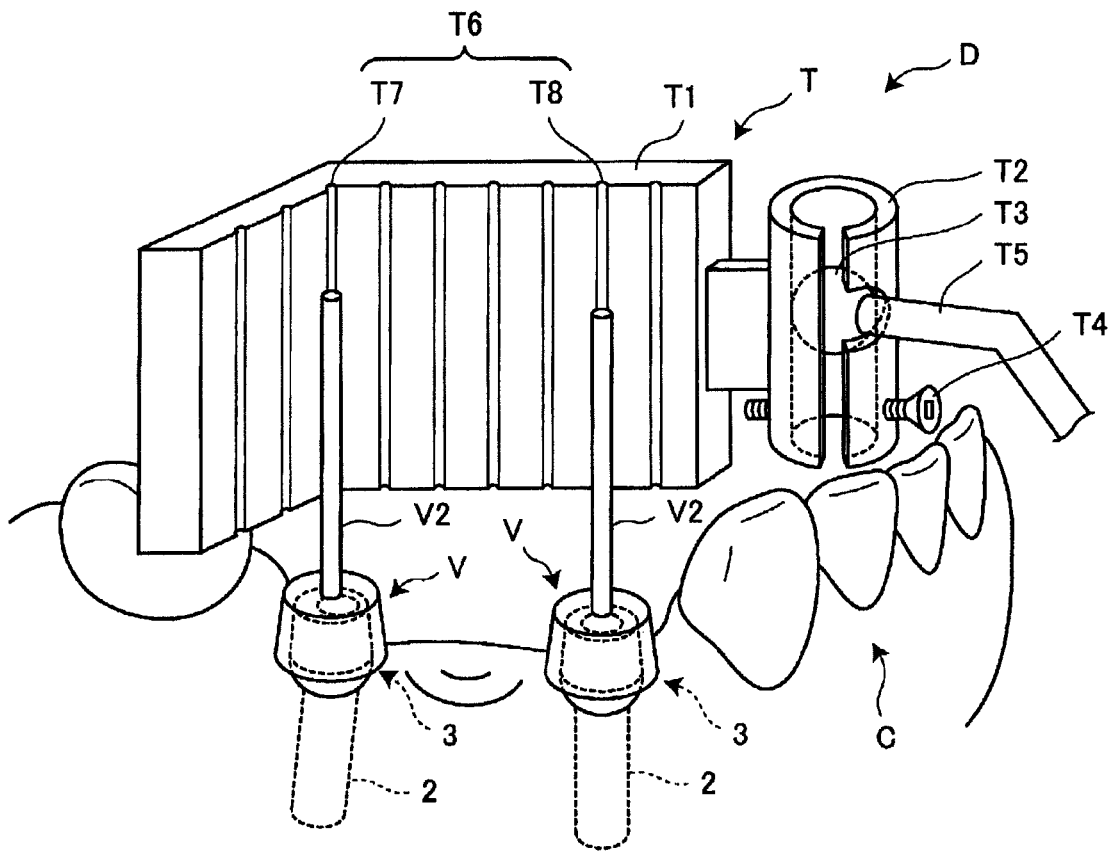
FIG. 45 is an explanatory view showing the steps of the manner of using a paralleling jig.

That is, as shown in FIG. 45, with respect to the artificial tooth base 4 which is fitted on the abutment 3, a shape of an inner surface of the fitting hole at a lower portion of the artificial tooth base 4 is adjusted while measuring the degree of parallelism between the artificial tooth base 4 and the neighboring artificial tooth base 4 which is already assembled using a paralleling jig which is prepared separately.

The paralleling jig T used in this embodiment has the following constitution as shown in FIG. 45.

That is, the paralleling jig T is constituted of a wall body T1 which has an approximately L shape as viewed in a plan view and forms a plurality of longitudinal grooves T6 arranged parallel to each other on a side surface thereof, a cylindrical bracket T2 which is connected to a side portion of the wall body T1 and has a longitudinally slit, a connecting ball T3 having a spherical distal end which is fitted in the inside of the cylindrical bracket T2, and a handle portion T5 which is connected to the connecting ball T3. Further, a fastening screw T4 is mounted on a peripheral surface of the cylindrical bracket T2 in a transverse state. When the fastening screw T4 is slackened, a peripheral surface of the cylindrical bracket T2 having the longitudinally slit is expanded so that a fitting state of the connecting ball T3 is loosened whereby an angle of the L-shaped wall body T1 can be freely displaced in the oral cavity D.

In measuring the degree of parallelism using the paralleling jig T, a measuring jig V is also used. That is, the measuring jig V is constituted of a cup portion V1 which is engaged with the abutment 3 and a pin V2 which stands upright on an upper portion of the cup portion V1.

In use, the cup portions V1, V1 of the measuring jig V are fitted on outer peripheries of the abutments 3 in the oral cavity D, the L-shaped wall body T1 of the paralleling jig T is inserted into the inside of the oral cavity D, and the degree of parallelism of the abutments 3 is measured based on whether or not the pins V2, V2 of the measuring jig V are fitted into the longitudinal grooves T6 formed on the L-shaped wall body T1 in parallel, and an inclination angle of the respective abutments 3 is adjusted to obtain the parallel abutments 3. Here, the parallel adjustment is performed by fitting one pin V2 in the groove T7 formed in a bent corner portion of the wall body T1 of the paralleling jig T and by fitting the other pin V2 in the groove T8 formed in the wall body T1 of the paralleling jig T.

(5) Artificial Tooth Base Removing Jig

Figure 52:
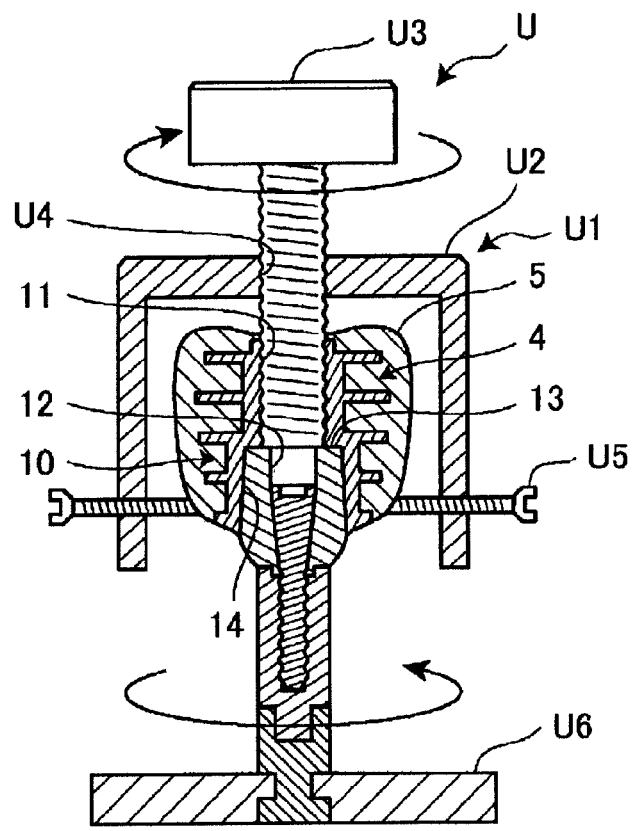
FIG. 52 is an explanatory view showing the steps of the manner of using the artificial tooth base removing jig.

In the above-mentioned steps v), xi), the artificial tooth base removing jig U is used for forcibly removing the artificial tooth base 4 from the abutments 3 or the temporarily holding anchor 80. The artificial tooth base removing jig U is constituted such that a hole U4 which allows the insertion of a separation male screw jig U3 to pass therethrough is formed in a ceiling plate U2 of a downwardly-opened approximately U-shaped jig body U1, and clamping bolts U5 whose distal ends are brought into contact with a peripheral surface of the artificial tooth base 4 are threadedly engaged with left and right side plates of the jig body U1 (see FIG. 52).

In use, the abutment 3 which constitutes an integral body with the artificial tooth base 4 is removed from the fixture 2 using the male screw fastening jig M in the inside of the oral cavity D, the abutment 3 is threadedly engaged with a jig receiving base U6 of the artificial tooth base removing jig U, the artificial tooth base 4 is covered with the jig body U1 from above and the jig body U1 is fixed to a peripheral surface of the artificial tooth base 4 by way of the clamping bolt U5, and the separation male screw jig U3 is threadedly engaged with the female threaded hole 11 from above thus fastening the separation male screw jig U3 to a limit. Accordingly, the artificial tooth base 4 is rotated in the opposite direction so that the artificial tooth base 4 can be forcibly removed from the taper fitting structure 10 (see FIG. 50 to FIG. 53).

The above-mentioned paragraphs I to V describe the embodiments relating to the dental implant structure.

However, these embodiments merely constitute some embodiments relating to the human body implant structure, and the gist of the present invention lies in the human body implant technique for various lost-part compensation parts including the implant technique for artificial teeth.

That is, as the lost-part compensation part, for example, an artificial eye, an artificial ear, an artificial nose and the like are named. In mounting such a lost-part compensation part, a support anchor is embedded in a bone body in the vicinity of a human body lost part, a support base is placed on and fixed to an upper portion of the support anchor, and various lost-part compensation part is mounted and fixed to the support base.

The lost-part compensation part is an artificial eye H, an artificial ear I, an artificial nose J or the like which is provided for compensating for a part of a human body which is lost due to an accident or the like. That is, the lost-part compensation part is an artificially manufactured part which resembles a lost part as much as possible.

The structure for mounting such a lost-part compensation part is substantially equal to the part mounting structure described heretofore and hence, the assembling method and the disassembling method used for the structure are applicable to the structure for mounting such a lost-part compensation part.

Hereinafter, the explanation is made with respect to embodiments relating to the artificial ear implant structure which implants an artificial ear as a lost-part compensation part, wherein the support anchor is embedded in a bone body in the vicinity of porus acusticus, and a support base is placed on and fixed to an upper portion of the support anchor. The artificial ear implant structure described hereinafter uses the same constitution as the dental implant structure described above and hence, the respective constitutions of the artificial ear implant structure are explained using the same symbols used for indicating the respective constitutions of the above-mentioned dental implant structure.

As shown in FIG. 54, support anchors 8, 8 are embedded in a bone body G in the vicinity of a porus acusticus. The support anchor 8 is constituted of an artificial ear abutment 3 and an artificial ear fixture 2. These members may be formed as an integral body when necessary. An artificial ear base 4 is placed on and fixed to an upper portion of the artificial ear abutment 3, and an artificial ear H is mounted on the artificial ear base 4 so as to compensate for a lost ear. The artificial ear H is made of silicon or the like.

Figure 55:
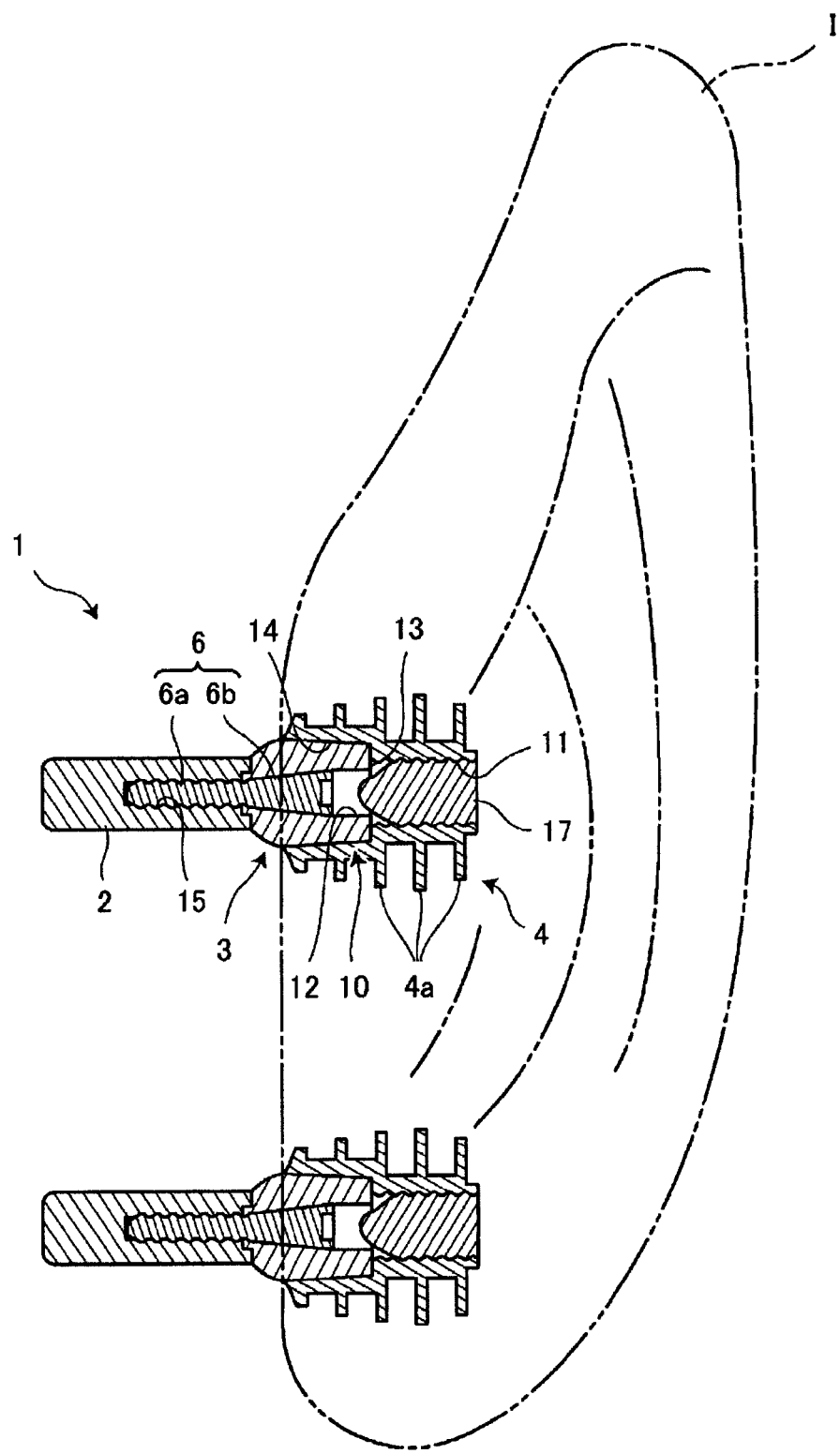
FIG. 55 is an explanatory view showing the artificial ear implant structure.
Figure 56:
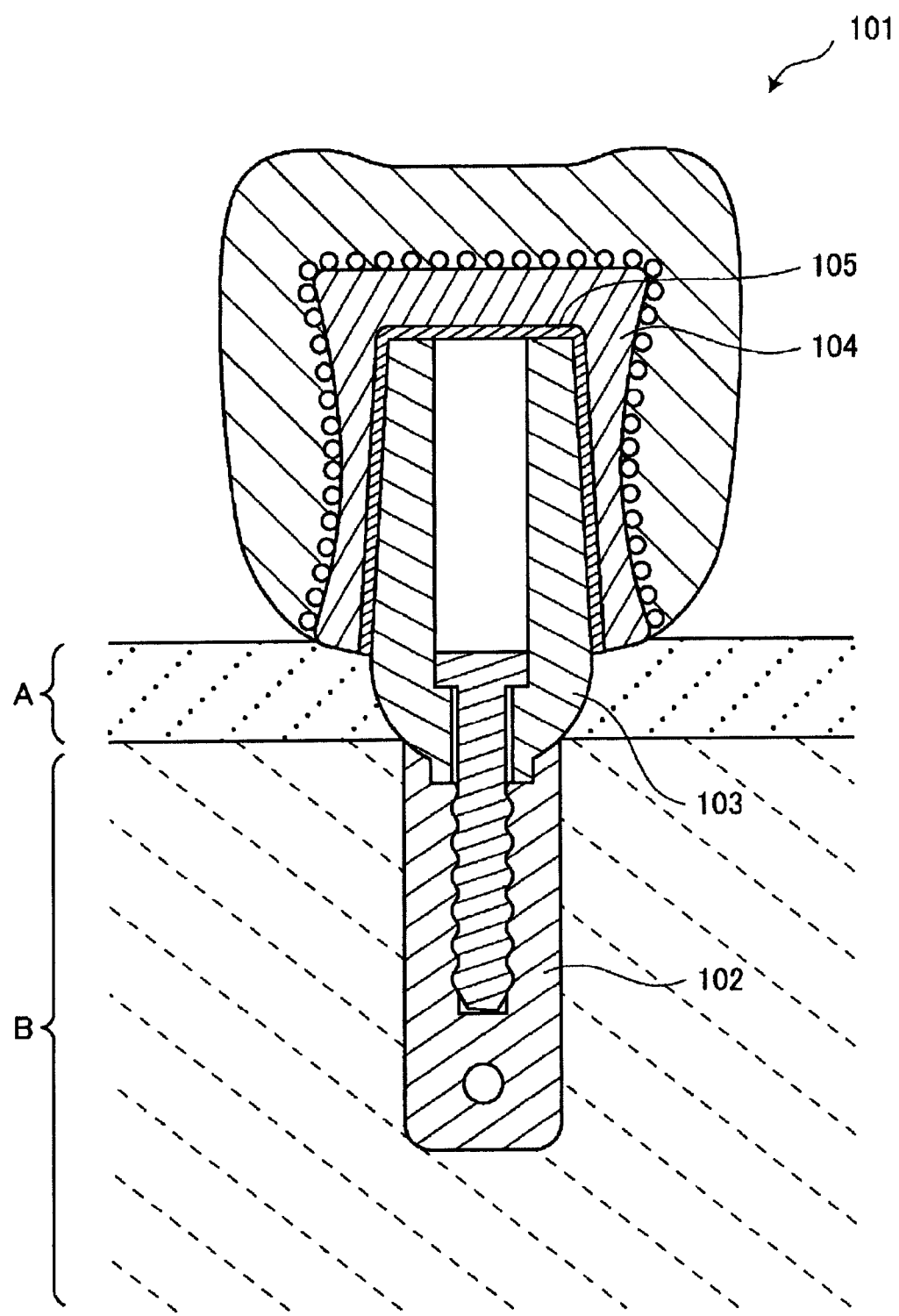
FIG. 56 is an explanatory view showing a conventional dental implant structure.
Figure 57:
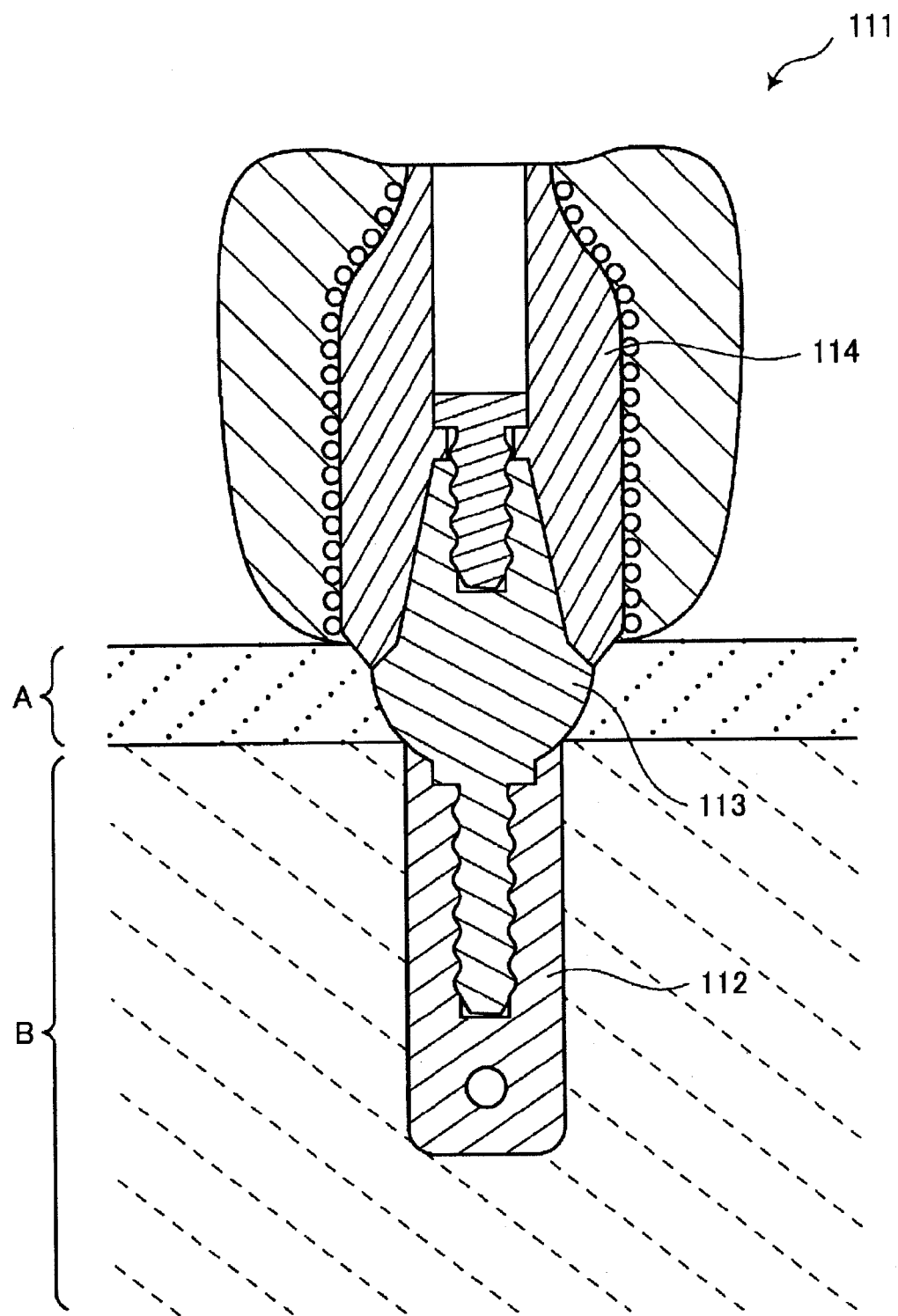
FIG. 57 is an explanatory view showing a conventional dental implant structure.

In addition, as shown in FIG. 55 and FIG. 56, an outer peripheral surface of the artificial ear abutment 3 and an inner peripheral surface of a fitting hole 14 formed in the artificial ear base 4 are respectively formed into tapered surfaces which correspond to each other so that the artificial ear abutment 3 and the artificial ear base 4 are brought into close contact with each other. In this manner, both the artificial ear abutment 3 and the artificial ear base 4 are configured to be detachably fitted to each other by way of the taper fitting structure 10. Further, a female threaded hole 11 which is vertically formed in the artificial ear base 4 has a larger diameter than a male screw penetration hole 12 which is vertically formed in the artificial ear abutment 3 thus forming a stepped portion 13 constituted of an upper surface of the artificial ear abutment 3 on a boundary between the female threaded hole 11 and the male screw penetration hole 12 which are communicated with each other.

Further, the male screw penetration hole 12 formed in the artificial ear abutment 3 in a penetrating manner is tapered such that a diameter of the hole 12 is gradually increased upwardly.

Further, the artificial ear fixture 2 which is embedded in the bone body B in the vicinity of porus acusticus and the artificial ear abutment 3 which is configured to place and fix the artificial ear 5 onto the upper portion thereof are contiguously connected to each other as an integral body by way of a male screw rod 6. An upper half portion of the male screw rod 6 has an upwardly enlarged tapered shape which conforms with a shape of the tapered male screw penetration hole 12 formed in the artificial ear abutment 3 in a penetrating manner. Here, a hexagonal recessed portion 2a is formed on an upper portion of the artificial ear fixture 2 which constitutes one part of the integral body, and a hexagonal projecting portion 3a is formed on a lower portion of the artificial ear abutment 3 which constitutes the other part of the integral body. The projecting portion 3a of the artificial ear abutment 3 is detachably fitted into the recessed portion 2a of the artificial ear fixture 2.

The artificial ear abutment 3 is formed into a substantially bowl shape, and the male screw penetration hole 12 is formed in an upper surface which constitutes the stepped portion 13.

In this embodiment, the stepped portion 13 is constituted such that the female threaded hole 11 formed in the artificial ear base 4 has the larger diameter than the male screw penetration hole 12 formed in the artificial ear abutment 3. However, the stepped portion 13 may be formed such that both the female threaded hole 11 and the male screw penetration hole 12 have the substantially same diameter. For example, the male screw penetration hole 12 having a perfect circular shape as viewed in a plan view and having a straight shape in cross section is slightly formed into an approximately elliptical shape as viewed in a plan view by caulking an upper-surface opening portion of the abutment 3. Further, a diameter of the female threaded hole 11 formed in the artificial ear base 4 is set substantially equal to a diameter of a long-axis corresponding portion of the upper-surface opening portion having a substantially elliptical opening in the male screw penetration hole 12. Due to such a constitution, it is possible to form a stepped portion 13 constituted of an upper surface of the artificial ear abutment 3 on a boundary between the female threaded hole 11 and the male screw penetration hole 12 which are communicated with each other. Accordingly, also in this case, in removing the artificial ear base 4 from the artificial ear abutment 3, the artificial ear base 4 can be removed from the artificial ear abutment 3 by bringing a flat portion Q3 of a separation male screw jig Q into contact with the stepped portion of the artificial ear abutment 3.

Here, a length of the male screw rod 6 may be set shorter than the length of the male screw rod 6 described in the above-mentioned example so as to allow the removal of the male screw rod 6 from the artificial ear fixture 2 by making use of a stroke between an upper end of the male screw rod 6 and the upper surface opening portion having a substantially elliptical opening in a threadedly engaged state.

The method of assembling the above-mentioned artificial ear implant structure, the method of disassembling the above-mentioned artificial ear implant structure, jigs which are separately used for these methods and the like are substantially equal to those for the digital implant structure and hence, their explanation is omitted.

Threaded grooves may be formed on an outer periphery of the fixture.

Although the present invention has been explained heretofore in conjunction with respective embodiments, the present invention is not limited to these embodiments, and shapes of the respective constitutional elements, a layout of the device and the like can be suitably changed without departing from the gist of the present invention.

What is claimed is:

1. A human body implant structure adapted for adjustment with a separation jig having a threaded length portion, the implant structure comprising:
    a support anchor which is configured to be embedded into a bone body;
    a support base which is placed on and fixed to an upper portion of the support anchor; and
    a lost-part compensation part which is mounted on an upper portion of the support base,
    wherein the support anchor and the support base are configured to provide a tapered fit structure comprising contacting tapered surfaces of the support anchor and support base, the tapered fit structure configured to detachably hold the support anchor and support base together, during use of the human body implant structure, without using either one of cement adhesion or screw thread engagement, and
    wherein a stepped portion which is formed of an upper surface of the support anchor is formed on a boundary between a female threaded hole which is vertically formed in the support base and a vertical hole formed in the upper surface of the support anchor, and
    wherein the support anchor and the support base are further configured so that when the human body implant structure is positioned relative to the separation jig, the separation jig threadingly engages the female threaded hole of the support base so that when the separation jig is turned in a given direction, the separation jig threaded length portion advances along said female threaded hole of the support base while an end portion of the separation jig abuts an end portion of a screw rod of said support anchor, whereby the support base is pushed out of a tapered fit with said support anchor separating the support base from the support anchor so as to enable said adjustment of the human body implant structure.

2. The human body implant structure according to claim 1, wherein
    the bone body is a jaw bone,
    the support anchor is constituted of the combination of a fixture, and an abutment which is configured to be placed on and fixed to an upper portion of the fixture and to place and fix an artificial tooth which constitutes the lost-part compensation part onto an upper portion thereof,
    the support base is constituted of an artificial tooth base, and
    the lost-part compensation part is constituted of the artificial tooth, the human body implant structure is constituted of a dental implant structure, and the abutment and the artificial tooth base are configured to be detachably fitted to each other by way of the taper fitting structure where the abutment and the artificial tooth base are brought into close contact with each other without using cement adhesion and screw thread engagement.

3. The human body implant structure according to claim 2, wherein the fixture which is configured to be embedded into the jaw bone and the abutment which is configured to place and fix the artificial tooth onto the upper portion thereof are integrally connected to each other by way of said screw rod whose upper half portion has a non-threaded upwardly enlarged tapered shape which conforms with a shape of a male screw penetration hole which is formed in the abutment in a penetrating manner, the shape of the male screw penetration hole being formed in an expanded manner with a diameter thereof increasing upwardly.

4. The human body implant structure according to claim 2, wherein an engaging portion with which a wire used in orthodontic is engaged is provided to the artificial tooth base instead of the artificial tooth which constitutes a lost-part compensation part.

5. The human body implant structure according to claim 1, wherein the fixture and the abutment are formed into an integral structure.

6. The human body implant structure according to claim 1, wherein the lost-part compensation part is one selected from a group consisting of an artificial eye, an artificial ear and an artificial nose.

7. The human body implant structure according to claim 1, wherein the taper structure is configured and sized with an upwardly decreasing taper having a diameter that decreases upwardly so as to be capable of fitting engagement of the support anchor and the support base.

8. A human body implant structure adapted for adjustment with a separation jig having a threaded length portion, the implant structure comprising:

a support anchor which is configured to be embedded into a bone body;

a lost-part compensation part; and a support base having an external surface to which the lost-part compensation part is directly affixed, and having an inner surface in contact with an external surface of the support anchor at a portion of the support anchor external to the bone body;

wherein the support base has a through channel comprising a first portion which is threaded, a second portion which is unthreaded, tapered, and of a wider diameter than the first portion, and a step portion located between said first portion and said second portion so that the through channel has a narrowest opening at an end of the support base at said first portion and has a widest opening at an opposite end of the support base at said second portion;

wherein said support base is held to said support anchor only by surface tension between said tapered second portion of the support base through channel and said external surface of the support anchor, said external surface of the support anchor having a taper corresponding to said tapered second portion, said surface tension excluding cement adhesion and excluding screw thread engagement;

wherein the support anchor comprises a fixture embedded into the bone body, an abutment having an unthreaded through opening, and a screw rod which secures the abutment to the fixture, the screw rod having a first end portion that is threaded and mates into a female threaded opening of the fixture, and having a second end portion that is contained within the unthreaded through opening of the abutment; and wherein when the separation jig threadingly engages with said first portion of the through channel of the support base and is turned, the human body implant structure is adjusted for removal of the abutment from the support base.

9. The human body implant structure of claim 8, wherein the abutment and the support base are configured to matingly engage to a tapered fit that provides said surface tension that holds said support base to said support anchor at said abutment without using cement adhesion and without screw thread engagement; and wherein the abutment and the support base are further configured with the screw rod, so that when the separation jig is turned in a given direction, the separation jig first length portion advances along said first portion of the through channel of the support base causing the support base to separate from the abutment as a force is applied by the separation jig at said end portion of the separation jig against the second end portion of the screw rod that is contained within the unthreaded through opening of the abutment, so as to achieve said adjustment.

* * * * *